(12) United States Patent
Sancho-Madrid et al.

(10) Patent No.: US 9,205,153 B2
(45) Date of Patent: *Dec. 8, 2015

(54) IMMUNE MODULATION VIA C-TYPE LECTIN

(71) Applicant: Cancer Research Technology Limited, London (GB)

(72) Inventors: David Sancho-Madrid, London (GB); Oliver Schulz, London (GB); Neil Charles Rogers, London (GB); Caetano Reis e Sousa, London (GB); Olivier Pierre Joffre, London (GB); Daniel Pennington, London (GB)

(73) Assignee: Cancer Research Technology Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/049,563

(22) Filed: Oct. 9, 2013

(65) Prior Publication Data

US 2014/0328865 A1    Nov. 6, 2014

Related U.S. Application Data

(63) Continuation of application No. 12/669,940, filed as application No. PCT/GB2008/002504 on Jul. 21, 2008, now Pat. No. 8,580,266.

(60) Provisional application No. 60/929,999, filed on Jul. 20, 2007.

(30) Foreign Application Priority Data

Mar. 19, 2008   (GB) .................................. 0805159.1

(51) Int. Cl.
| | |
|---|---|
| *C07K 16/00* | (2006.01) |
| *C12P 21/08* | (2006.01) |
| *A61K 47/48* | (2006.01) |
| *A61K 39/00* | (2006.01) |
| *C07K 16/28* | (2006.01) |

(52) U.S. Cl.
CPC ....... *A61K 47/48415* (2013.01); *A61K 39/0005* (2013.01); *A61K 39/0011* (2013.01); *C07K 16/2851* (2013.01); *C07K 16/2878* (2013.01); *A61K 2039/507* (2013.01); *A61K 2039/57* (2013.01); *A61K 2039/6056* (2013.01); *C07K 2316/96* (2013.01); *C07K 2317/55* (2013.01); *C07K 2317/75* (2013.01); *C07K 2319/33* (2013.01)

(58) Field of Classification Search
None
See application file for complete search history.

(56) References Cited

U.S. PATENT DOCUMENTS

2003/0042386 A1    3/2003   Krebs et al.

FOREIGN PATENT DOCUMENTS

| WO | 01/55163 | 8/2001 |
| WO | 03/054152 | 7/2003 |

OTHER PUBLICATIONS

Gollnick, S.O., et al. "Generation of effective antitumor vaccines using photodynamic therapy." Cancer Res. Mar. 15, 2002;62(6):1604-8.
Sancho, D., et al. "Identification of a dendritic cell receptor that couples sensing of necrosis to immunity." Nature. Apr. 16, 2009;458(7240):899-903.
Nakazaki, Y., et al. "Vaccine effect of granulocyte-macrophage colony-stimulating factor or CD80 gene-transduced murine hematopoietic tumor cells and their cooperative enhancement of antitumor immunity." Gene Ther. Oct. 1998;5(10):1355-62.
Caminschi, I., et al. "The dendritic cell subtype-restricted C-type lectin Clec9A is a target for vaccine enhancement." Blood. Oct. 15, 2008;112(8):3264-73. Epub Jul. 30, 2008.
Huysamen, C., et al. "CLEC9A is a novel activation C-type lectin-like receptor expressed on BDCA3+ dendritic cells and a subset of monocytes." J Biol Chem. Jun. 13, 2008;283(24):16693-701. Epub Apr. 11, 2008.
Clark, H.F., et al. "The secreted protein discovery initiative (SPDI), a large-scale effort to identify novel human secreted and transmembrane proteins: a bioinformatics assessment." Genome Res. Oct. 2003;13(10):2265-70. Epub Sep. 15, 2003.
Weis, W.I., et al. "The C-type lectin superfamily in the immune system." Immunol Rev. Jun. 1998;163:19-34.
Sobanov, Y., et al. "A novel cluster of lectin-like receptor genes expressed in monocytic, dendritic and endothelial cells maps close to the NK receptor genes in the human NK gene complex." Eur J Immunol. Dec. 2001;31 (12):3493-503.
Carter, R.W., et al. "Preferential induction of CD4+ T cell responses through in vivo targeting of antigen to dendritic cell-associated C-type lectin-1." J Immunol. Aug. 15, 2006;177(4):2276-84.
Kanazawa, N., et al. "Dendritic cell immunoreceptors: C-type lectin receptors for pattern-recognition and signaling on antigen-presenting cells." Journal of Dermotological Science. 2007;45:77-86.

*Primary Examiner* — Amy Juedes
(74) *Attorney, Agent, or Firm* — Kathleen D. Rigaut; Dann, Dorfman, Herrell and Skillman, P.C.

(57) ABSTRACT

The invention relates to the regulation of the immune system, and in particular to the finding that the CLEC9a molecule is a marker for dendritic cells which are capable of cross-presenting extracellular antigens via the MHC class I pathway. This makes them particularly suitable for generation of cytotoxic T lymphocyte responses. Materials and methods are provided both for the induction of immune responses against target antigens, and for the inhibition or suppression of undesirable immune responses in which these cells are involved.

9 Claims, 28 Drawing Sheets

Fig.1

Human CLEC9A cDNA sequence

ATGCACGAGGAAGAAATATACACCTCTCTTCAGTGGGATAGCCCAGCACCAGAGACACTTACCAGAAATGTCT
GTCTTCCAACAAATGTTCAGGAGCATGTCTTGTGATGGTCTTCATGTGTTTCTGCATGGGATTATTA
ACAGCATCCATTTCTTGGGCGTCAAGTTGTTGCAGTGTCCACCATTGCGATGCAGCAGCAGAGAAAACT
CATCCAACAGAGAGGCACTGCTAAACTTACAGAATGGAAGAGAAGCTGTGCCCTTCAGATGAAATATT
GCCAAGCCTTCATGCAAAACTCATTAAGTTCAGCCCATAACAGCAGTCCTTGTCCAAACAATTGGATTCAGA
ACAGAAAGTTGTTACTATGTCTCTGAAATTTGGAGCATTTGGAGAAGAGAATCAAGAGAATTGTTTAAAGG
AAGGTTCCACGCTGCTACAAATAGGGTGGGGTTGTCTCAGGATGGACACAGCCAGTCAGCTAACAAGTCT
AAGGAAGCTATGATTACTCCTGGCCTGTGCCAGAGATCCCAGTCAGCTAACAAGTCTGTGGATACGTGA
CTCCTCTCCTCTCCTGGCCTGTGCCAGAGATCCCAGTCAGCTAACAAGTCTGTGGATACGTGA
AAGCAATTCCCTTCGTCTAACTGCAGCACGTGAAGTATTTATCTGTGAGAAGTATGCGTTGAGAT
CCTCTGTCTGA

Human CLEC9A protein sequence  Cytoplasmic tail/*transmembrane/neck*/<u>CTLD</u>

MHEEEIYTSLQWDSPAPDTYQKCLSSNKCSGA*CCLVMVISCVFCMGLLTASIFLGVKLLQVSTIAMQQQEKLIQQERALLN*
*FTEWKRSCALQMKYCQAFMQNSLSSAHNSSPCPNNWIQNRESCYYVSE*<u>IWSIWHTSQENCLKEGSTLLQIESKEEMDFIT</u>
<u>GSLRKIKGSYDYWVGLSQDGHSGRWLWQDGSSPSPGLLPAERSQSANQVCGYVKSNSLLSSNCSTWKYFICEKYALRS</u>
<u>SV</u>

Fig. 2.

Mouse CLEC9a cDNA sequence

ATGCATGCGGAAGAAATATACCTCTCTCTTCAGTGGGACATTCCTGAGAGGCCTCTCAGAAGTGCCAATC
CCTAGCAAATGTTCAGGAGCATGGTGTTGTTGACGATGATTTCCTGTGTGTTGGCTTGTTAGCAA
CGTCCATTTCTTGGGCATCAAGTTCTTCCAGGTATCCTCTCTGTCTTGGAGCAGGAAAGACTCATCCAAC
AGGACACAGCATTGGTGAACCTTACACAGTGGCAGAGGAAATACACACTGGAATGCCAAGCCTTACTGCAG
AGATCTCTCCATTCAGGCAAGGAAACAGGTAGTGACTGCAGCCCTTGTCCACACAGTCTTCTGACCTCTCCACAGAC
CCTGGACAGCAAGGAAACAGGTAGTGACTGCAGCCCTTGTCCACACAGAGCTCAGAATGGAAAAGTTGT
ACTATGTCTTTGAACGCTGGGAAATGTGGAACATCAGCAGTCAGTGAACATCAAGAAAATAAATATTGGGT
CAAATAGACAGCAAAGAAGAAATGGAGTTCATCAGTCAGTGAACTCAAAGGAAGAAAATAAATATTGGGT
GGGAGTGTTTCAAGATCAGTGGAATCAGTGGATCTTGGTTCTGGAAGATGGCTCTCCTCTCTGACTGTTGC
CTGCAGAAAGACAGCGATCAGCCGGCCAGATGTTGTGTGAGAAGGCAGTTTGGATCCTGCATCTGA
GATAGCTGGAAATATTTATCTGTGTGAGAAGGCAGTTTGGATCCTGCATCTGA

Mouse CLEC9a protein sequence Cytoplasmic tail/*transmembrane/neck*/<u>CTLD</u>

MHAEEIYTSLQWDIPTSEASQKCQSPSKCCSGA*WCVVTMISCVVVCMGLLATSIFLGIKFFQVSSLVLEQQERLIQQDTALVN
LTQWQRKYTLEYCQALLQRSLHSGTDASTGPVLLTSPQMVPQTLDSKETGSDCSPCPHNWIQNGKSCYYVFERWEMWN
ISKKSCLKEGASLFQ*IDSKEEMEFISSIGKLKGGNKYWVGVFQDGISGSWFWEDGSSPLSDLLPAERQRSAGQICGYLKD
STLISDKCDSWKYFICEKKA*FGSCI

Fig. 5

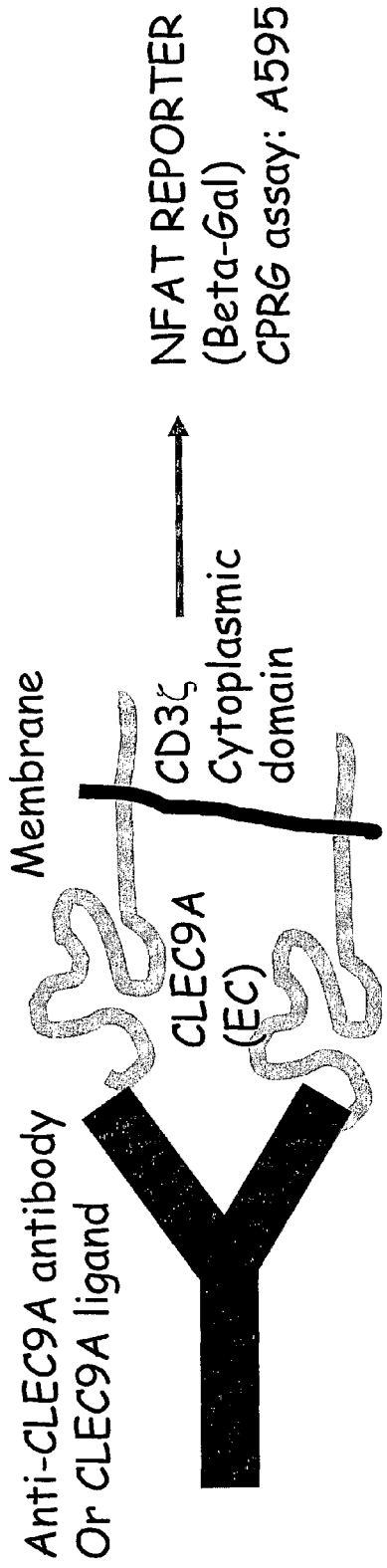

Anti-CLEC9A antibody
Or CLEC9A ligand

Membrane

CLEC9A (EC)

CD3ζ Cytoplasmic domain

→ NFAT REPORTER (Beta-Gal)
CPRG assay: A595 cDNA sequence of chimera: Cytoplasmic CD3ζ - transmembrane NKRP1B - extracellular CLEC9a)

ATGAGAGCAAAATTCAGCAGGAGTGCAGAGACTGCTGCCAACCTGCAGGACCCCAACCAGCTCTACA
ATGAGCTCAATCTAGGGCGAAGAGAGAGGAGGAGGAGAATATGACGTCTTGGAGAAGAAGCGGGCTCGGATCCAGA
GATGGGAGGCAAACAGCAGCCTACACAGTGGAACCCCCAGGAAGGCGTATACAATGCACTGCAGAAAGA
CAAGATTGCAGAGAAGCCTCAGCCACTGCCAAAGGGGCACACAAGGACACCTATGATGCCCTGCAGACCCTGG
TGGCCTTTACCAGGTCTCAGCACTGCCACCAAGGACACCTATGATGCCCTGCAGACCCTGG
CCCCTCGCTGTCGGTGCCCTCGCTGCCCTCGTGCTGGTTGGCTGTCTGTATCAGTCAGAAATTTGGCTGTGCTGGCCTCATCCTTC
TTGTGCTGGTGTCGTGATTGGACTCTCTGTCTGTCTTGTCGATTCAGAATGGAAAAGTTGTTACTGTCTTTCAAATGACAGCAAA
ACTGCAGCCCTTGTCCACACAACTGTAAGAGAGCCAGTAGGAGAAACTCAAAGGGGTGGGAGTGTT
AAATGTGGAACATCAGTAGAGTTCATCAGCAGATCTGTTAAAGGAAGAGAATAAATATTGGGTGGGAGTGTT
GAAGAAATGGAGTTCATCAGCAGATCGTGGTTCTGGGAAGATGGCTCTCTCGACTTGTGCCTGC
TCAAGATGATGAATCAGTGAGTCCGGCCAGATCTGTGATACCCTGTGGATACCTGTGATCTCTCATCTCAGATAAGT
AGAAAGACAGGCGATCAGCGCGGCCAGATCTGTGAGAAGAAGGCATTTGGATCCTGATCTGA
GCGATAGCTGTGAAATATTTTATCTGTGAGAAGAAGGCATTTGGATCCTGATCTGA

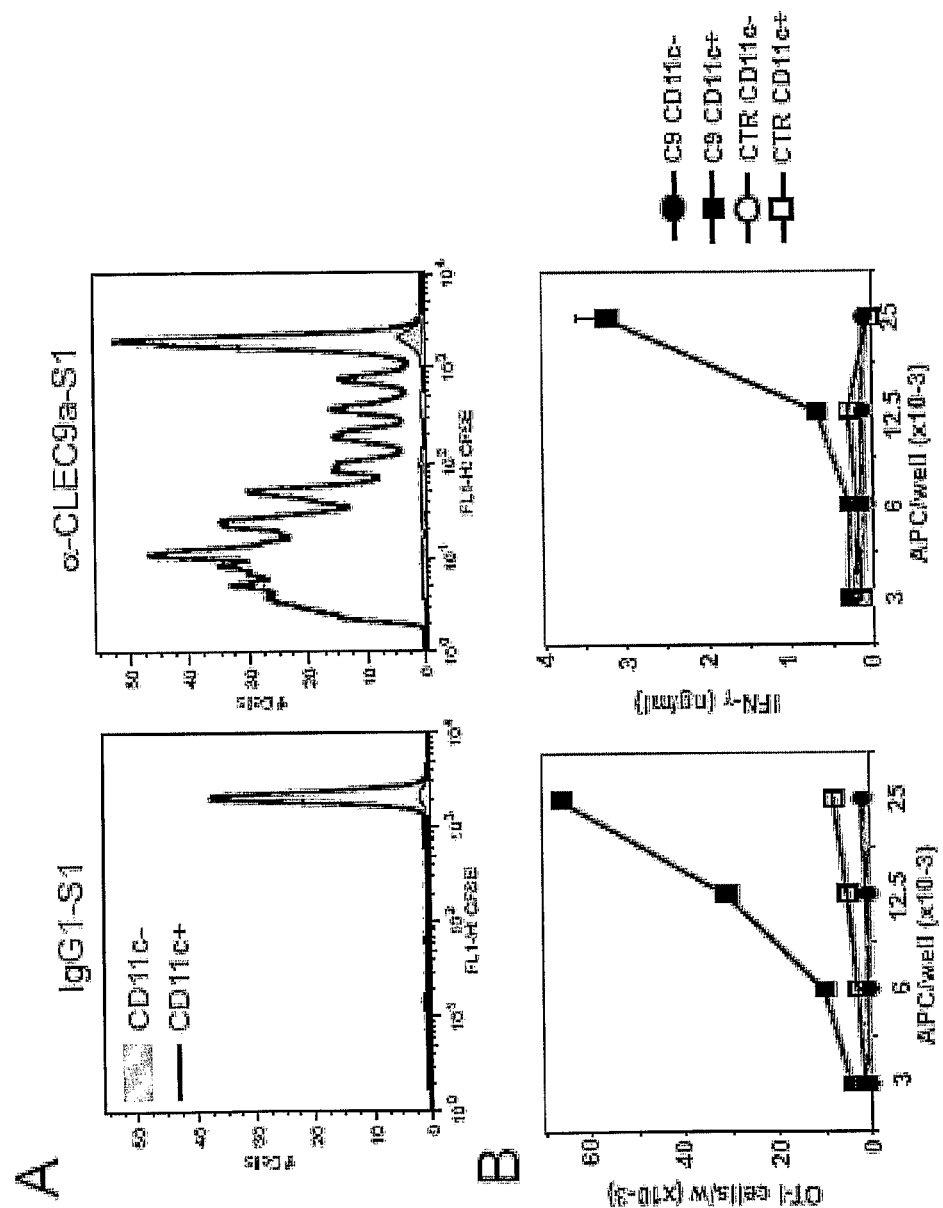
Fig. 12A-B.

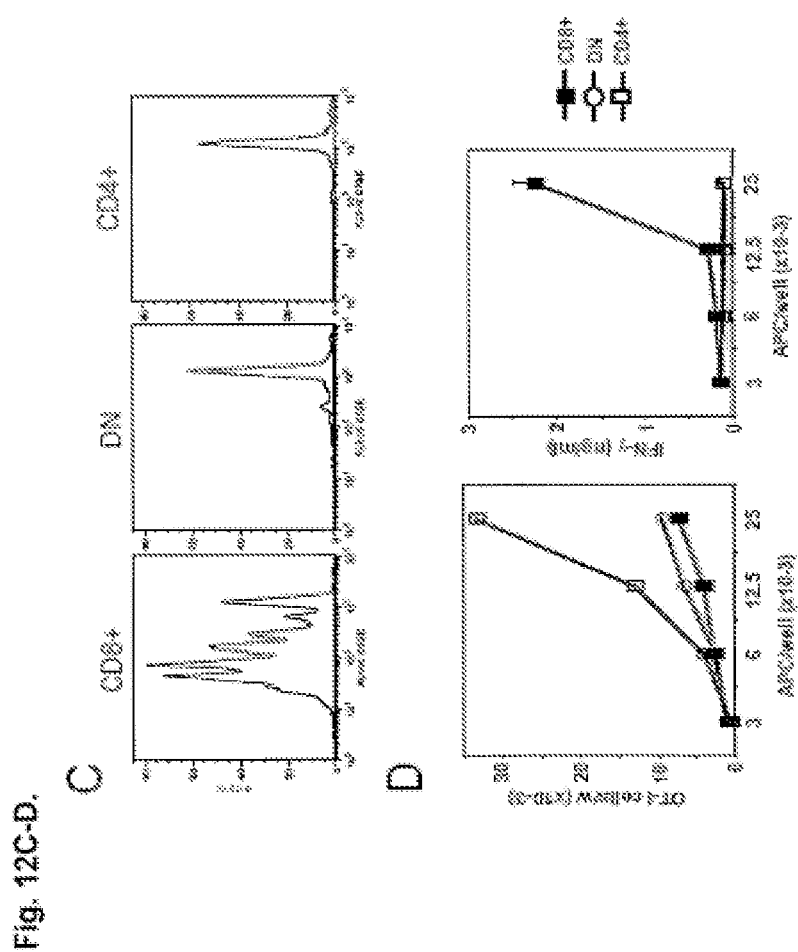
Fig. 12C-D.

IMMUNE MODULATION VIA C-TYPE LECTIN

The present application is a continuation of U.S. patent application Ser. No. 12/669,940, filed May 10, 2010, which is a §371 application of PCT/GB2008/002504 filed Jul. 21, 2008 which claims priority to U.S. Provisional Application 60/929,999 filed Jul. 20, 2007 and GB Application No. 0805159.1 filed Mar. 19, 2008, the entire disclosure of each being incorporated by reference herein.

The invention relates to the regulation of the immune system, and in particular to the use of molecules having affinity for the CLEC9a molecule to prime and inhibit immune responses to target antigens.

BACKGROUND TO THE INVENTION

The immune system is able to detect the presence of infectious agents, and trigger a response against them, without destroying self tissues. This phenomenon is not trivial, given the enormous molecular diversity of pathogens, and their high replication and mutation rates. Multi-cellular organisms have been challenged over the course of evolution to develop several distinct immune-recognition systems, namely the 'innate' and 'adaptive' immune systems.

The evolutionarily ancient innate immune system detects the presence and nature of infection, provides the first line of host defence, and controls the initiation and determination of the effector class of the adaptive immune system.

Dendritic cells (DC) play an essential role in linking innate immunity and antigen-specific adaptive responses. To initiate an immune response, DC are primed (inter alia) by pathogen-associated molecular patterns (PAMP) expressed by pathogens. Then DC orchestrate development of the adaptive immune response, much more specialized and driven by antigen-specific T- and B-cells.

The antigen recognition and uptake functions of DC against pathogens are mediated by pattern recognition receptors (PRR) that discriminate among the PAMPs. These PRR expressed by DC include the Toll-like receptors (TLR)[1]. In addition, DC express another class of receptors, the C-type lectins, some of which may function as PRRs[2-4], and/or mediate intercellular communication[5-8]. Within the C-type lectins, there is a group of type II proteins with a single extracellular C-type lectin domain (CTLD) that are structurally and evolutionary closely related, and clustered in the NK gene complex (NKC). Although these receptors lack a calcium binding site and a typical carbohydrate recognition domain, they may still be able to bind carbohydrates, as shown for Dectin-1[9]. Some of these receptors (CD94/NKG2, NKG2D) interact with MHC-I or related molecules and either inhibit or activate NK and T cell cytotoxicity as a result of the balance between inhibitory and activating signals. However, for most of NK lectin receptors their binding specificity and relevance in NK or DC function is not known. Thus, C type lectins expressed on DC may act to recognise microbes, but may also regulate the communication of DC with other cells by recognizing specific cellular counterstructures.

The ontogeny and/or microenvironment in which DC are positioned may result in the expression of distinct combinations of surface receptors by DC. For example, phenotypic criteria alone allow the classification of mouse lymph node DCs into six main subpopulations[10]. Of these, conventional non-plasmacytoid DC in lymphoid tissues are traditionally sub-divided into $CD8\alpha^-$ and $CD8\alpha^+$ subpopulations. It has been argued that different DC subsets may be involved in specific recognition of certain pathogens and/or regulate different immune responses, e.g. Th1 or Th2 (immunity) or regulatory T cells (tolerance)[11]. However, the phenotype and functional behavior of DCs is also significantly conditioned by external activating stimuli, denoting significant plasticity. As a first approach to understanding the differences between DC subsets, DC subpopulations were isolated and their properties in vitro were assessed: in mouse, $CD8\alpha^+$ and $CD8\alpha^-$ subsets of spleen DC differ in their ability to make IL-12 in vitro[12,13]. However, the differential IL-12 production in vitro was also determined by the pattern recognition, demonstrating functional flexibility of different DC subsets[14]. As a second approach, DC subsets were isolated, antigen-pulsed, and then re-infused in vivo. $CD8\alpha^+$ and $CD8\alpha^-$ subsets differentially primed Th1 and Th2 responses in vivo[15,16]. Immune therapy is feasible if we can determine molecules that are selectively expressed in a particular DC subset. These molecules can then be targeted to alter the function of this subset of DCs.

SUMMARY OF THE INVENTION

The inventors have found that CLEC9a is preferentially expressed on the subset of dendritic cells that express CD8 in mice, and so are designated $CD8^+$ dendritic cells. This is an important cell type because it is believed to be capable of processing antigens derived from outside the cell and presenting them to T cells via MHC class I molecules. This is in contrast to most antigen presenting cells, which present extracellularly-derived antigens via MHC class II molecules. Consequently, this mechanism of antigen presentation is sometimes referred to as "cross-presentation". These cells therefore play an important role in the generation and stimulation of cytotoxic T cell (CTL) responses, which are an essential part of the immune response against intracellular pathogens (e.g. viruses) and cancers.

This finding opens up a number of applications. For example, it enables antigens to be specifically targeted to dendritic cells capable of cross-presentation.

Thus, in a first aspect, the invention provides a method for targeting an antigen to an antigen presenting cell, comprising contacting the antigen presenting cell with a composition comprising the antigen, wherein the antigen is associated with a binding agent having affinity for CLEC9a, and wherein the antigen presenting cell expresses CLEC9a.

The method may be applied in vitro or in vivo. The antigen presenting cell will typically be a dendritic cell, and preferably is capable of cross-presenting extracellular antigen via MHC class I molecules. By "extracellular" is meant that the antigen has been taken up by the cell from its extracellular environment, typically by endocytosis or phagocytosis.

The invention further provides a method for stimulating an immune response against an antigen in a subject, comprising administering to the subject a composition comprising the antigen, wherein the antigen is associated with a binding agent having affinity for CLEC9a.

The method may comprise a single administration, or a sequence of two or more-administrations separated by suitably determined intervals of time. For example, the method may comprise a priming step (i.e. a first administration) followed by one or more boosting steps (a subsequent administration or administrations). For example, a first administration and second administration may be separated by one or more days, one or more weeks, or one or more months, preferably between two weeks and one month. Subsequent administrations may be provided after one or more weeks or months.

Immune responses stimulated via CLEC9a targeting involve proliferation of T cells, which may be CTL or helper T cells. Antigen presenting cells (and in particular dendritic cells) expressing CLEC9a can induce proliferation of both CD8+ T cells and CD4+ T cells, and may stimulate proliferation of both types of T cell in any given immune response.

Under certain conditions, it is believed that they are capable of stimulating regulatory T cell (Treg) proliferation. Treg cells are characterised by the expression of the Foxp3 (Forkhead box p3) transcription factor. Most Treg cells are CD4+ and CD25+, and can be regarded as a subset of helper T cells, although a small population may be CD8+. Thus the immune response which is to be stimulated by a method of the invention may comprise inducing proliferation of Treg cells in response to an antigen. Thus the method may comprise administering to the subject a composition comprising the antigen, wherein the antigen is associated with a binding agent having affinity for CLEC9a. The antigen may be administered with an adjuvant which promotes proliferation of Treg cells.

Insofar as this method involves stimulating proliferation and differentiation of Treg cells in response to a specific antigen, it can be considered to be a method of stimulating an immune response. However, given that Treg cells may be capable of modulating the response of other cells of the immune system against an antigen in other ways, e.g. inhibiting or suppressing their activity, the effect on the immune system as a whole may be to modulate (e.g. suppress or inhibit) the response against that antigen. Thus the methods of this aspect of the invention can equally be referred to as methods of modulating (e.g. inhibiting or suppressing) an immune response against an antigen.

In practice, then, these methods of the invention may be used therapeutically or prophylactically to inhibit or suppress an undesirable immune response against a particular antigen, even in a subject with pre-existing immunity or an on-going immune response to that antigen. This may be particularly useful (for example) in the treatment of autoimmune disease.

Under certain conditions, it may also be possible to tolerise a subject against a particular antigen by targeting the antigen to an antigen presenting cell expressing CLEC9a. The invention thus provides a method for inducing tolerance in a subject towards an antigen, comprising administering to the subject a composition comprising the antigen, wherein the antigen is associated with a binding agent having affinity for CLEC9a, and wherein the antigen is administered in the absence of an adjuvant.

Tolerance in this context typically involves depletion of immune cells which would otherwise be capable of responding to that antigen, or inducing a lasting reduction in responsiveness to an antigen in such immune cells.

Typically the subject is vertebrate, preferably a mammal. The subject may be a human, other primate, or a domestic, laboratory or livestock animal, such as a mouse, rat, guinea pig, lagomorph (e.g. rabbit), cat, dog, pig, cow, horse, sheep or goat.

The invention further provides a composition comprising an antigen, wherein the antigen is associated with a binding agent having affinity for CLEC9a. The composition may be a pharmaceutical composition, e.g. a vaccine, containing the antigen and its associated binding agent in combination with a pharmaceutically acceptable carrier. It may be formulated for any suitable route of administration, including but not limited to intravenous, intramuscular, intraperitoneal, nasal, subcutaneous, intradermal, etc.

The invention further provides a composition comprising an antigen for use in a method of medical treatment, wherein the antigen is associated with a binding agent having affinity for CLEC9a.

Also provided is a composition comprising an antigen, for use in stimulating an immune response against the antigen, wherein the antigen is associated with a binding agent having affinity for CLEC9a.

Also provided is the use of a composition comprising an antigen in the preparation of a medicament for stimulating an immune response against the antigen, wherein the antigen is associated with a binding agent having affinity for CLEC9a. $CD8\alpha^+$ dendritic cells may be implicated in at least Th1, Th2, and Th17-type immune responses. Thus the methods of the invention may be applied to stimulation of various types of immune response against any antigen. However these cells are believed to be particularly important in the generation of CTL responses, so the immune response to be stimulated is preferably a CTL response. The method may comprise determining production and/or proliferation of CTLs, which are typically T cells expressing CD8 and are capable of cytotoxic activity against cells displaying their cognate antigen in the context of MHC class I molecules.

Nevertheless, targeting of antigen to CLEC9a+ dendritic cells can result in proliferation of helper T cells as well as, or instead of, CTLs. Thus the method may additionally or alternatively comprise determining production and/or proliferation of helper T cells. The helper T cells may be CD4+ T cells, and may be of Th1, Th2, Th17 or Treg type. They may also include other types of Treg cells which do not express CD4, e.g. CD8+ Treg cells.

It will therefore be understood that the methods and compositions described above may be used for the prophylaxis and/or treatment of any condition in which it is desirable to induce a CTL response, such as cancer, or infection by an intracellular parasite or pathogen, such as a viral infection.

It may be desirable also to administer further immunostimulatory agents in order to achieve maximal CTL stimulation and proliferation, and/or stimulation and proliferation of other T cell types. These may include agents capable of activating dendritic cells and stimulating their ability to promote T cell activation. Such an agent may be referred to as an adjuvant. The adjuvant may comprise an agonist for CD40 (such as soluble CD40 ligand, or an agonist antibody specific for CD40), an agonist of CD28, CD27 or OX40 (e.g. an agonist antibody specific for one of those molecules), a CTLA-4 antagonist (e.g. a blocking antibody specific for CTlA-4), and/or a Toll-like receptor (TLR) agonist, and/or any other agent capable of inducing dendritic cell activation. A TLR agonist is a substance which activates a Toll-like receptor. Preferably, the TLR agonist is an activator of TLR3, TLR4, TLR5, TLR7 or TLR9. A suitable TLR agonist is MPL (monophosphoryl lipid A), which binds TLR4. Other TLR agonists which may be used are LTA (lipoteichoic acid, which binds TLR2; Poly I:C (polyinosine-polycytidylic acid), which binds TLR3; flagellin, which binds TLR5; imiquimod or polyU RNA (1-(2-methylpropyl)-1H-imidazo(4,5-c) quinolin-4-amine), which binds TLR7 and CpG (DNA CpG motifs), which binds TLR9; or any other component which binds to and activates a TLR. For more details, see Reis e Sousa, Toll-like receptors and dendritic cells. Seminars in Immunology 16:27, 2004. Adjuvants which may not work via TLRs include 5' triphosphate RNA, poly I:C, and β-glucans such as curdlan (β-1,3-glucan). Pro-inflammatory cytokines such as TNF-α or IL-1 may also be used as adjuvants.

Binding agents which have CLEC9a agonist activity (e.g. are capable of cross-linking CLEC9a on the surface of dendritic cells, discussed in more detail below) may also be capable of activating dendritic cells. Such agonist binding agents may therefore be considered adjuvants in their own right. Thus, when such a binding agent is used, it may not be necessary to administer a further adjuvant such as those described above (although it may still be desirable to do so). Binding agents capable of acting as CLEC9a agonists are discussed in more detail below.

Without wishing to be bound by theory, it is believed that the nature of the adjuvant used may affect the type of response obtained. Antigen presenting cells expressing CLEC9a can stimulate both CD4+ T cells and CD8+ T cells, and the nature of the CD4+ response in particular may be affected by the adjuvant used. For example, use of poly I:C appears to favour generation of a Th1-type CD4+ response. Curdlan appears to stimulate a Th17-type CD4+ response Certain adjuvants promote stimulation of Treg cells. These include retinoic acid, and in particular all-trans retinoic acid (ATRA), also known as trenitoin. Thus, when the immune response to be stimulated is a Treg response (which may in practice suppress responses of other components of the immune system against a particular antigen) it may be appropriate to use a Treg-promoting adjuvant. It may also be possible to stimulate Treg cell stimulation without administration of an adjuvant.

The compositions of the invention may be administered with or formulated for administration with the adjuvant, either sequentially or simultaneously, in the same or separate compositions. Thus the compositions of the invention may, but need not, comprise an adjuvant.

Without wishing to be bound by theory, and as explained above, it is believed that administration of the antigen in the absence of an adjuvant may result in the development of tolerance to the antigen. That is to say, the immune system is induced not to respond to future administrations of the same antigen. This may (but need not) involve the generation of Treg cells which are capable of active suppression of the response. Thus further administrations of an antigen to a subject who has been tolerised to that antigen should result in a lesser immune response than in a subject who is naïve for that antigen (i.e. whose immune system has not previously been exposed to the antigen). The magnitude of the immune response may be assessed by any appropriate criteria, such as appearance of inflammation, swelling, cell proliferation (e.g. of Th1, Th2 or Th17 CD4+ T cells, or CTLs) or inflammatory cytokine production (e.g. IL-1, IL-4, IL-12, IFN-gamma, TNF-alpha). In certain embodiments, the tolerised individual will display substantially no immune response to that antigen.

In the above-described compositions and methods, the antigen is physically associated with the binding agent, which may be via covalent or non-covalent (e.g. electrostatic or van der Waals) interactions. Preferably the antigen is covalently coupled to the binding agent. For example, the binding agent may be coupled to the antigen via a suitable coupling reagent. The skilled person is well aware of suitable methods and reagents which may be used for such coupling reactions.

Alternatively, the antigen and binding agent may be part of the same peptide chain, i.e. they may be expressed as a fusion protein. The fusion protein may contain a linker sequence between the antigen and binding agent. Alternatively, the antigen and binding agent may be in physical proximity, e.g., a liposome, without chemical linkage.

The binding agent may be any suitable molecule having a sufficiently specific affinity for CLEC9a. Wherever such a binding agent is referred to throughout this specification, it may be a protein, nucleic acid (e.g. an aptamer), carbohydrate, or a small molecule. It may be a physiological ligand for CLEC9a or a variant or analogue thereof. However, antibodies against CLEC9a and functional fragments thereof are particularly preferred. Thus the binding agent may comprise an antibody binding site specific for CLEC9a. The binding agent may be polyvalent as described in more detail below.

The antigen is a peptide antigen. The term "peptide" refers to the nature of the antigen, i.e. that it is formed from amino acids linked by peptide bonds, and should not be taken to imply any particular size or length. Typically the peptide antigen will be at least 8 amino acids in length, and may be up to 30 amino acids in length, up to 50 amino acids in length, up to 100 amino acids, up to 200 amino acids, or even longer and may have residues coupled to the amino acids, such as glycon chains. For example, it may be 25 to 35 amino acids in length.

Without wishing to be bound by any particular theory, the peptide antigen should be capable of binding to a MHC class II or MHC Class I molecule, or should be capable of being processed within an antigen-presenting cell (such as a dendritic cell) to give rise to one or more peptides capable of binding to a MHC class II molecule or MHC Class I. It has recently been suggested that short epitope peptides of around 8 amino acids in length may induce less sustained CTL reactivity than longer peptides (e.g. around 30 amino acids in length) (21). MHC class I molecules typically bind peptides of 8 or 9 amino acids in length, while MHC class II molecules can bind peptides from 8 amino acids up to 20 amino acids, up 30 amino acids, or even longer.

The antigen may be any protein or fragment thereof against which it is desirable to raise an immune response, in particular a CTL response, but also a Th17 response or a Treg response. These may include antigens associated with, expressed by, displayed on, or secreted by cells against which it is desirable to stimulate a CTL response, including cancer cells and cells containing intracellular pathogens or parasites. For example, the antigen may be, or may comprise, an epitope peptide from a protein expressed by an intracellular pathogen or parasite (such as a viral protein) or from a protein expressed by a cancer or tumour cell. Thus the antigen may be a tumour-specific antigen. The term "tumour-specific" antigen should not be interpreted as being restricted to antigens from solid tumours, but to encompass antigens expressed specifically by any cancerous, transformed or malignant cell.

It may be particularly desirable to raise a Treg response against an antigen to which the subject exhibits, or is at risk of developing, an undesirable immune response. For example, it may be a self antigen against which an immune response occurs in an autoimmune disease. Examples of autoimmune diseases in which specific antigens have been identified as potentially pathogenically significant include multiple sclerosis (myelin basic protein), insulin-dependent diabetes mellitus (glutamic acid decarboxylase), insulin-resistant diabetes mellitus (insulin receptor), coeliac disease (gliadin), bullous pemphigoid (collagen type XVII), auto-immune haemolytic anaemia (Rh protein), auto-immune thrombocytopenia (GpIIb/IIIa), myaesthenia gravis (acetylcholine receptor), Graves' disease (thyroid-stimulating hormone receptor), glomerulonephritis, such as Goodpasture's disease (alpha3 (IV)NC1 collagen), and pernicious anaemia (intrinsic factor). Alternatively the target antigen may be an exogenous antigen which stimulates a response which also causes damage to host tissues. For example, acute rheumatic fever is caused by an antibody response to a Streptococcal antigen which cross-reacts with a cardiac muscle cell antigen. Thus these antigens, or particular fragments or epitopes thereof may be suitable antigens for use in the present invention.

Depletion of Treg cells or impairment of Treg cell function has been shown to result in autoimmune disease in murine models. Disease caused in test animals include arthritis (e.g. rheumatoid arthritis), inflammatory bowel disease, gastritis, pernicious anaemia, thyroiditis, insulitis, diabetes, sialoadenitis, adrenalitis, autoimmune orchitis/oophoritis, glomerulonephritis, chronic obstructive pulmonary disease and experimental autoimmune encephalitis and multiple sclerosis.

Induction of a regulatory T cell type 1 response has also been shown to reduce the development of atherosclerosis in murine models (Mallat Z. et al. Circulation 108:1232-7, 2003). Treg activity has also been shown to be significant in the rate at which allografts are rejected. Depletion of Treg cells or impairment of function accelerates the rate of rejection, while infusion of test animals with syngeneic lymphocytes enriched in Treg cells has been shown to prolong graft survival.

The methods of the present invention may therefore find use in the treatment of any of these conditions.

It may also be possible to stimulate an immune response (whether a CTL response or any other kind of T cell response, including a Treg response) against an antigen which is present within the subject's body without directly administering the antigen itself to the subject.

This may be achieved using a binding agent having affinity for the antigen and also having affinity for CLEC9a, such that the binding agent is capable of forming a complex with the antigen within the subject's body and targeting the antigen to an antigen presenting cell expressing CLEC9a.

The invention therefore provides a binding agent having a first binding site having affinity for CLEC9 and a second binding site having affinity for the antigen. Such binding agents will be referred to in this specification as "bispecific" binding agents. However it will be understood that the binding agents may have further binding sites with alternative binding affinities, e.g. for other antigens, and the term "bispecific" should be construed accordingly.

The invention further provides a bispecific binding agent as described above for use in a method of medical treatment, for example, in the stimulation of an immune response against a target cell. The target cell may be a cancer cell or a parasitised cell.

Further provided is use of a bispecific binding agent as described above in the manufacture of a medicament for the stimulation of an immune response against a target cell. The target cell may be a cancer cell or a parasitised cell.

Further provided is a method of stimulating an immune response against a target cell in a subject, comprising administering a bispecific binding agent to said subject. The subject may (for example) be suffering from cancer or from an intracellular parasitic infection.

The bispecific binding agent may be formulated for administration in conjunction with an adjuvant as described elsewhere in this specification, or may be formulated in the same composition as an adjuvant. The nature of the adjuvant may be selected depending on the nature of the desired response. Thus, for example, ATRA may be used where it is desirable to induce a Treg response against the antigen, curdlan may be used where a Th17 response is desired, and any other suitable adjuvant (e.g. anti-CD40, poly I:C, etc.) may be used where more conventional CTL responses are required. Where no adjuvant is administered, it may be possible to induce stimulation of Treg cells and/or tolerance to the antigen.

The invention further provides a pharmaceutical composition comprising a bispecific binding agent as described above, in admixture with a pharmaceutically acceptable carrier. The composition may further comprise an adjuvant, or may be for administration in conjunction with an adjuvant, as described elsewhere in this specification.

In some embodiments either or both binding sites may be antibody binding sites specific for CLEC9a or the antigen respectively. Thus the binding agent may be a bispecific antibody comprising at least a first antibody binding site specific for CLEC9a and at least a second antibody binding site having affinity for the antigen. The term "bispecific antibody" should be interpreted to encompass any molecule or molecular complex having such two binding sites, such as bispecific single chain Fv dimers and "diabodies" (see below).

The finding that the CLEC9a molecule is a marker for a specific subset of dendritic cells also makes it a suitable therapeutic target for downregulation of undesirable immune responses.

Thus in a further aspect, the invention provides a method of inhibiting an immune response in a subject comprising administering a binding agent having affinity for CLEC9a.

In this aspect of the invention, the binding agent is capable of directly or indirectly inhibiting dendritic cell function in a dendritic cell to which it is bound. The binding agent may inhibit CLEC9a from binding to its cognate ligand, or may inhibit an aspect of cell function such as maturation in response to adjuvant, or antigen presentation. Alternatively, the binding agent may be directly or indirectly capable of killing the cell, which may be regarded as a "depleting" activity. Typically the binding agent comprises an "effector" moiety responsible for directly or indirectly killing the cell or otherwise affecting antigen presentation.

For example, the binding agent may be capable of recruiting components of the subject's immune system, thus stimulating an immune attack on the cell. For example, an antibody Fc region may be used to recruit components of the complement system, which may lead to lysis of the cell via the lytic pathway of complement, or opsonisation of the cell and subsequent phagocytosis by phagocytic cells of the immune system such as neutrophils or macrophages. Phagocytes also possess Fc receptors which enable them to phagocytose cells bound by antibodies; thus antibodies can themselves mark cells for phagocytosis without activation of complement. Thus the effector moiety may comprise an antibody Fc region, for example of IgG or IgM.

The binding agent may comprise other types of effector moiety which act to kill targeted cells. For example, it may comprise a toxin molecule capable of killing the cell. This mechanism may be particularly effective, as the inventors have shown that antibodies binding CLEC9a can be endocytosed by dendritic cells, so a conjugated toxin molecule would have a high probability of being taken up into the cell.

Alternatively the effector moiety may be an enzyme capable of activating a prodrug in the vicinity of the cell, for example converting a non-toxic molecule into a toxic molecule.

As already described, the binding agent may comprise an antibody binding site specific for CLEC9a.

Useful binding agents therefore include molecules comprising an antibody binding site specific for CLEC9a, and one or more of an antibody Fc region, a toxin molecule, or an enzyme capable of activating a prodrug.

The binding agent may itself be a functional antagonist of CLEC9a. Thus, it may simply be sufficient for the binding agent to bind to CLEC9a in order to exert its inhibitory function, by preventing CLEC9a from binding to its cognate ligand, or from exerting its normal signalling role, e.g. in dendritic cell maturation and/or antigen presentation. In such embodiments, it may be desirable that the binding agent comprises only one or two binding sites (e.g. antibody binding sites) specific for CLEC9a. For example, the binding agent may be (or comprise) an antibody or an antibody fragment, such as a Fab or scFv fragment.

Antagonists which prevent binding of CLEC9a to its ligand may be particularly useful in the treatment of autoimmune diseases. Some autoimmune diseases are characterised by unusually high levels of cell death and it is believed that immune responses against self antigens associated with these cells may contribute to the pathogenesis of these conditions. CLEC9a antagonists may therefore be used to prevent CLEC9a from binding to the ligand exposed in dead and dying cells (especially those undergoing immunogenic cell death) and may thus inhibit or prevent stimulation of immune responses against these antigens.

Other functional antagonists of CLEC9a may also be useful in the methods described. Such antagonists include nucleic acids or analogues thereof capable of hybridising to mRNA or DNA encoding CLEC9a (for example, ribozymes, antisense RNA or DNA molecules, siRNA, etc.), small molecule antagonists of CLEC9a, etc.

Yet further CLEC9a antagonists are competitors for the CLEC9a ligand, which can block binding sites on the ligand for dendritic cell-associated CLEC9a and so prevent the ligand from being recognised or bound by the dendritic cell. Suitable competitors include soluble molecules comprising the extracellular domain of CLEC9a or a portion thereof sufficient to bind to the CLEC9a ligand.

The CLEC9a extracellular domain (or portion thereof) may be associated with a heterologous moiety which may modulate some property of the antagonist, such as its pharmacokinetic properties in vivo. The extracellular domain may be covalently or non-covalently bound to the heterologous moiety, or may be expressed as a fusion protein with the heterologous moiety. For example, the heterologous moiety may be an antibody Fc domain, in order to provide increased serum half life and allow efficient clearance of complexes between the antagonist and the CLEC9a ligand.

Other possible functions of the heterologous moiety include mediating oligomerisation of the CLEC9a extracellular domain, and facilitation purification of the antagonist or isolation from a sample. For example, a suitable antagonist may be a soluble molecule comprising or consisting of the CLEC9a extracellular domain (or a fragment thereof sufficient to bind CLEC9a ligand) associated with an avidin monomer. The avidin monomers will tend to associate into tetramers, providing a complex comprising four CLEC9a domains and four avidin subunits. This construct can readily be isolated by contact with biotin, which may be provided on a solid support such as a bead.

Where the binding agent or antagonist is a protein, it may be possible to administer a nucleic acid (e.g. DNA) encoding the antagonist. Typically the nucleic acid will be taken up by cells within the body (e.g. muscle cells), expressed, and secreted from those cells. This approach is often referred to as DNA vaccination.

Antibodies are particularly suitable as binding agents and antagonists, and can conveniently be expressed in scFv form. If necessary, an antibody can be encoded as a fusion protein with the antigen, or with an effector moiety as described above. An example of a DNA vaccination approach is described in Nchinda et al., J. Clin. Invest. 118(4), 1427-36, 2008.

The nucleic acid typically comprises a coding region encoding the binding agent or antagonist, optionally in conjunction with any desired fusion partner, in operable linkage with transcriptional and translational regulatory sequences to ensure appropriate expression and secretion of the protein from cells which take up the nucleic acid. Such sequences include (but need not be limited to) transcriptional initiation sequences (e.g. promoter and enhancer), transcriptional termination sequences, appropriate splicing signals, translational initiation and termination sequences, and a signal peptide to enable secretion.

Thus the invention further provides a nucleic acid (e.g. a DNA) encoding a CLEC9a antagonist or binding agent, for use in a method of medical treatment. Also provided is a nucleic acid encoding a CLEC9a antagonist or binding agent for use in a method of and therapeutic uses thereof.

The subject to whom the binding agent or antagonist is administered may be suffering from an inflammatory or autoimmune condition, especially a condition characterised by undesirable CTL activity, and/or a condition characterised by high levels of cell death. Such conditions include:

autoimmune diseases, including rheumatoid arthritis and other types of chronic or acute arthritis or arthropathies with an immune component, systemic lupus erythematosus (which is known to involve particularly high levels of cell death), scleroderma, Sjögren syndrome, autoimmune (particularly Type I) diabetes, thyroiditis, and other organ-specific immune diseases, including psoriasis;

neurologic diseases, including multiple sclerosis, myasthenia gravis, and other neurologic immune-mediated diseases. Also included are gastrointestinal diseases, including Crohn's disease, colitis, celiac disease and hepatitis;

cardiovascular diseases, which are now recognised to have a significant immune-mediated component, including atherosclerosis, cardiomyopathy, rheumatic fever, endocarditis, vasculitis, and other immune-mediated cardiovascular diseases;

immune-mediated respiratory diseases, including emphysema, respiratory airways infections, and other immune-mediated respiratory diseases;

allergic processes and hypersensitivity reactions (type I, II, III, and IV), including asthma, rhinitis, and other immune-mediated hypersensitivity reactions;

transplant or graft rejection and graft versus host disease, as occurs during or subsequent to, for example, organ transplant, tissue graft, blood transfusion, bone marrow transplant;

immunopathological responses to infectious agents, including septic shock syndromes;

degenerative processes, such as neurodegenerative processes, that implicate immune competent cells such as microglia.

The invention further provides a binding agent having affinity for CLEC9a, or a CLEC9a antagonist, for use in a method of medical treatment.

Also provided is a binding agent having affinity for CLEC9a, or a CLEC9a antagonist, for use in the inhibition of an immune response.

Also provided is the use of a binding agent having affinity for CLEC9a, or a CLEC9a antagonist, in the preparation of a medicament for the inhibition of an immune response.

The inventors have also found that CLEC9a agonists are capable of activating dendritic cells, and may therefore be useful in stimulating immune function, even when not physically associated with an antigen. Thus the invention provides a method of stimulating an immune response in a subject, comprising administering a binding agent having affinity for CLEC9a.

The CLEC9a agonist may be a binding agent having affinity for CLEC9a, and may comprise an antibody binding site specific for CLEC9a.

Without wishing to be bound by theory, it is believed that binding agents having more than two binding sites (e.g. antibody binding sites) specific for CLEC9a may be particularly effective agonists of CLEC9a activity, probably because they can cross-link or cause association or multimerisation of CLEC9a on a cell surface. Binding agents may be referred to as "bivalent" if they possess two such binding sites or "polyvalent" if they possess more than two such binding sites. Therefore the binding agent is preferably polyvalent, and may comprise at least three, four, five, ten or even more binding sites. Such binding agents may comprise a plurality of binding sites immobilised in or on a particle, such as a bead (e.g. of latex), a liposome or vesicle, or any other suitable particle. Thus the binding sites may be immobilised on or in a particulate solid phase. Alternatively a polyvalent binding agent may simply comprise more than two binding sites covalently linked or otherwise associated with one another. For example, whole antibodies or functional fragments thereof (see below) may be associated as fusion proteins and/or by chemical cross-linking. The skilled person is well aware of suitable techniques for preparing such polyvalent binding agents. When the methods are performed in vitro, binding agents (such as antibodies against Clec9a) immobilised on a surface of the culture vessel can be used as agonists; in this case the coated surface of the culture vessel may itself be considered a polyvalent binding agent.

The agonist may be administered alone, in order to stimulate immune function generally, or in conjunction with a target antigen against which it is desirable to induce an immune response. The agonist and antigen can be administered separately or in the same composition, simultaneously or sequentially, as desired. The agonist may be physically associated with the antigen as described above in relation to the first aspect of the invention, or the two components may be physically separate, distinct entities.

As already described, the methods and compositions described may be particularly useful for the prophylaxis and/or treatment of any condition in which it is desirable to induce a CTL response, such as cancer, or infection by an intracellular parasite or pathogen, such as a viral infection.

The methods and compositions described may also used for the prophylaxis and/or treatment of any condition in which it is desirable to induce a Treg response, e.g. a condition involving an undesirable or inappropriate immune response against a particular condition, such as an autoimmune disease.

A further immunostimulatory agent or adjuvant as described above may also be administered in association with the agonist and optionally the antigen. Thus the adjuvant may comprise, for example, a CD40 agonist or a TLR agonist. The nature of the adjuvant may be selected depending on the nature of the desired immune response. Thus, for example, if a Th17-type CD4 T cell response or a Treg response is desirable, the adjuvant may be selected accordingly.

Identification of CLEC9a as a marker for a subset of dendritic cells provides means for identification and isolation of such cells from biological samples.

Thus, in a further aspect, the invention provides a method of detecting an antigen presenting cell in a sample, comprising contacting the sample with a binding agent having affinity for CLEC9a and determining binding of the binding agent to one or more cells.

The method also provides a method of isolating an antigen presenting cell from a sample, comprising contacting the sample with a binding agent having affinity for CLEC9a and isolating one or more cells to which the binding agent is bound. The binding agent may be immobilised on a solid support (such as a magnetic bead) in order to facilitate isolation.

As will be clear from the discussion above, the antigen presenting cell is typically a dendritic cell, and may be capable of cross-presenting extra-cellular antigen via MHC class I molecules.

In order to confirm that the cells identified by the binding agent for CLEC9a are dendritic cells, or to enrich a sample for dendritic cells before contacting the cells with the binding agent for CLEC9a, the method may comprise the step of contacting the sample with a second binding agent having affinity for a dendritic cell marker and determining binding of the second binding agent to one or more cells. The two binding agents may be contacted with the cells simultaneously or sequentially, and in any order. In some embodiments, only those cells to which both the first and second binding agents bind are identified or isolated.

The dendritic cell marker may be a pan-dendritic cell marker such as CD11, especially CD11c (in mice).

For samples of human dendritic cells, the dendritic cell marker may be HLA-DR. It may be desirable to confirm that the cells are lineage-negative, i.e. they do not express CD3, CD14, CD19 or CD56.

For samples of human cells, it may be desirable to confirm that the cells identified by the binding agent for CLEC9a also express BDCA-3 (also known as CD141 or thrombomodulin). The method may therefore comprise the step of contacting the sample with a further binding agent having affinity for BDCA-3 and determining binding of the further binding agent to one or more cells, and/or isolating cells to which the further binding agent binds. The binding agents for CLEC9a and BDCA-3 may be contacted with the cells simultaneously or sequentially, and in any order. In some embodiments, only those cells to which both binding agents bind are identified or isolated.

Additionally or alternatively, it may be desirable to enrich the sample for the desired cell type by negative selection for one or more unwanted cell types. The unwanted cell types may comprise other subgroups of dendritic cells such as plasmacytoid dendritic cells (pDCs), which may be excluded by negative selection for CD123 or Ly6C. Negative selection may be performed before, simultaneously with, or after selection for cells expressing CLEC9a. Negative selection may be performed for CD3, CD14, CD19, and/or CD56.

It may also be desirable to determine the level of CLEC9a expression on the cells. This may make it possible only to select cells which express a desired level of CLEC9a, e.g. a higher level of CLEC9a than another population of cells which expresses CLEC9a at a detectable level. For example, without wishing to be bound by theory, it is believed that the subset of DCs which expresses CD8 (or is equivalent to that subset in humans) expresses a higher level of CLEC9a than pDCs. It may therefore be possible to select CD8 DCs or their equivalents by only selecting those cells which express CLEC9a above a certain threshold level.

The binding agents may be labelled to facilitate detection and/or isolation of the cells, e.g. with a label capable of emitting a detectable signal (such as a fluorescent or radioactive label) or with an affinity tag capable of being specifically bound by a binding partner. Examples of affinity tags and binding partners include epitopes and cognate antigens, positively charged peptides (e.g. poly-His) and metal (e.g. nickel) ions, avidin/streptavidin and biotin, carbohydrates and lectins, etc. The skilled person will be able to design a suitable system depending on their specific requirements.

Identification or isolation of the cells may involve contacting the sample with one or more detecting agents capable of binding to the first and/or second binding agent. The detecting agent may itself be labelled as described above.

To facilitate isolation or detection, the binding or detecting agent may be immobilised on a solid support.

The invention further provides a population of antigen presenting cells isolated by a method as described above.

The cells isolated by these methods may be used for various purposes, including in vitro study and ex vivo therapy. For example, isolated cells may be pulsed with a desired antigen in vitro. The cells may then be administered to a subject in order to stimulate an immune response against the antigen.

Thus, the invention further provides a method of stimulating an immune response against a peptide antigen comprising providing an antigen presenting cell or population thereof isolated by a method as described above, and contacting said cell or population of cells with said antigen.

Preferably, the antigen presenting cells present said antigen or a fragment thereof in the context of MHC class I molecules.

Following said contacting step, the cell or population of cells may be administered to a subject. Preferably the cells are re-administered to the subject from whom they were derived.

The cell or population of cells may also be contacted with an adjuvant, as described above. Contacting may take place in vitro, for example at or approximately at the same time as contacting with the antigen, or at or after administration to the recipient subject. Contact with the adjuvant may stimulate the capacity of the cell or population of cells to activate or promote proliferation of T cells in response to the antigen. The adjuvant may be administered simultaneously with the cells, or sequentially, in the same or different compositions. The immunostimulatory adjuvant may be, for example, a CD40 agonist or a TLR agonist. The nature of the adjuvant may be selected depending on the nature of the desired immune response. Thus, for example, if a Th17-type CD4 T cell response or a Treg response is desirable, the adjuvant may be selected accordingly.

The invention therefore provides a primed antigen presenting cell or population thereof, obtained by the methods described above. By "primed" is meant that the cell has been contacted with an antigen, is presenting that antigen or an epitope thereof in the context of MHC molecules, preferably MHC I molecules, and is capable of activating or stimulating T cells to proliferate and differentiate into effector cells in response thereto.

Also provided is a primed antigen presenting cell or population thereof, obtained by the methods described above, for use in a method of medical treatment, and especially for use in a method of stimulating the immune response against a target antigen. Also provided is the use of a primed antigen presenting cell or population thereof, obtained by the methods described above, in the preparation of a medicament for the stimulation of an immune response against a target antigen.

Alternatively the primed cells may be contacted with T cells in vitro in order to generate T cells (particularly CTLs, but also CD4+ T cells, including Th17 and Treg cells) specific for the antigen. Thus, following said contacting step, the method may comprise contacting said antigen presenting cells with a population of cells comprising one or more T cells. The T cells in the population may be allowed to expand in culture in order to increase the number or proportion of T cells in the population which are specific for the antigen. The T cells may then be administered to a subject. Optionally the T cells are separated from other cells in the population before administration.

The population of cells may also be contacted with an adjuvant, for example at substantially the same time as they are contacted with the primed antigen presetting cells.

Preferably, the T cells and antigen presenting cells are autologous, i.e. they are derived from the same subject, or from genetically identical subjects.

The T cells may be re-administered to the subject from whom they (or their progenitors) were derived.

Again, an adjuvant may be administered with the T cells, when they are administered to the subject. the adjuvant may be a CD40 agonist (such as an antibody specific for CD40) or a TLR agonist. The adjuvant may be administered simultaneously with the T cells or sequentially, in the same or different compositions.

The invention therefore further provides a T cell or population thereof, obtained by the methods described above. Also provided is a T cell or population thereof, obtained by the methods described above, for use in a method of medical treatment, and especially for use in a method of stimulating an immune response against a target antigen. Also provided is the use of a T cell or population thereof, obtained by the methods described above, in the preparation of a medicament for the stimulation of an immune response against a target antigen.

The invention further provides an isolated population of human dendritic cells expressing CLEC9a. The population may contain at least 5, at least 10, at least 100, at least 1000 or at least 10,000 dendritic cells. Preferably at least 50%, at least 60%, at least 70%, at least 80%, at least 90%, or at least 95% of the dendritic cells within the population express CLEC9a. For this purpose, dendritic cells are considered to be lineage-negative, HLA-DR$^+$ cells. Lineage-negative cells do not express CD3, CD14, CD19 or CD56.

The isolated population may be comprised within a sample comprising other cell types, as long as the required proportion of dendritic cells within the sample expresses CLEC9a. Thus the sample may comprise lymphocytes (for example T cells, and especially CTLs), or other types of antigen presenting cells which are not dendritic cells.

The dendritic cells expressing CLEC9a will typically be BDCA-3+. They may also be CD123$^-$, CD34$^-$, CD16$^-$ and CD11b/c$^-$.

The invention further provides a method of stimulating an immune response against a peptide antigen comprising providing a population of human dendritic cells expressing CLEC9a, and contacting said population with said antigen.

Following said contacting step, the population of human dendritic cells expressing CLEC9a may be administered to an autologous subject; i.e. they are administered to a subject from whom they were originally derived.

The population of human dendritic cells expressing CLEC9a may also be contacted with an adjuvant, as described above. Contacting may take place in vitro, for example at or approximately at the same time as contacting with the antigen, or at or after administration to the recipient subject. Contact with the adjuvant may stimulate the capacity of the population of cells to activate or promote proliferation of T cells in response to the antigen. The adjuvant may be administered simultaneously with the cells, or sequentially, in the same or different compositions. The immunostimulatory adjuvant may be, for example, a CD40 agonist or a TLR agonist. The nature of the adjuvant may be selected depending on the nature of the desired immune response. Thus, for example, if a Th17-type CD4 T cell response or a Treg response is desirable, the adjuvant may be selected accordingly.

The invention therefore provides a population of human dendritic cells expressing CLEC9a, primed with an antigen. By "primed" is meant that the cell has been contacted with an antigen, is presenting that antigen or an epitope thereof in the context of MHC molecules, preferably MHC I molecules, and is capable of activating or stimulating T cells to proliferate and differentiate into effector cells in response thereto.

Also provided is a primed population of human dendritic cells expressing CLEC9a for use in a method of medical treatment, and especially for use in a method of stimulating the immune response against a target antigen. Also provided is the use of a primed population of human dendritic cells expressing CLEC9a in the preparation of a medicament for the stimulation of an immune response against a target antigen.

Alternatively the primed cells may be contacted with T cells in vitro in order to generate T cells (particularly CTLs, but also helper T cells or Tregs) specific for the antigen. Thus, following said contacting step, the method may comprise contacting said population of human dendritic cells expressing CLEC9a with a population of cells comprising one or more T cells. The T cells in the population may be allowed to expand in culture in order to increase the number or proportion of T cells in the population which are specific for the antigen.

The T cells may then be administered to a subject. Optionally the T cells are separated from other cells in the population before administration. As in other aspects of the invention, the dendritic cells and T cells may also be contacted with an adjuvant. The nature of the adjuvant may be selected depending on the nature of the desired immune response. Thus, for example, if a CTL response, Th17-type CD4 T cell response or a Treg response is desirable, the adjuvant may be selected accordingly.

Preferably, the T cells and dendritic cells are autologous, i.e. they are derived from the same subject, or from genetically identical subjects.

The T cells may be re-administered to the subject from whom they (or their progenitors) were derived.

Again, an adjuvant may be administered with the T cells. the adjuvant may be a CD40 agonist (such as an antibody specific for CD40) or a TLR agonist. The adjuvant may be administered simultaneously with the T cells or sequentially, in the same or different compositions.

The invention therefore further provides a T cell or population thereof, obtained by the methods described above. Also provided is a T cell or population thereof, obtained by the methods described above, for use in a method of medical treatment, and especially for use in a method of stimulating an immune response against a target antigen. Also provided is the use of a T cell or population thereof, obtained by the methods described above, in the preparation of a medicament for the stimulation of an immune response against a target antigen.

In all of the above-described aspects, the antigen may be any antigen against which it is desirable to stimulate an immune response, particularly a CTL response, a Th17-type response or a Treg response. For example, the antigen may be an antigen expressed by an intracellular pathogen or parasite, or may be expressed by a cancer cell, as described elsewhere in this specification. Alternatively it may be an antigen against which an undesirable or inappropriate response takes place (e.g. in an autoimmune disease) and against which it is desired to stimulate a Treg response.

The surprising finding that CLEC9a binds to a ligand found on or in mammalian cells, rather than infectious agents, also makes available assays for the identification of the ligand.

Thus the invention provides a method of screening for a physiological ligand for CLEC9a comprising contacting a target substance comprising the extracellular domain of CLEC9a or a portion thereof sufficient to bind CLEC9a ligand with a test substance which is a component of a mammalian cell, and determining binding of the target substance to the test substance.

Binding may indicate that the test substance is a (or the) physiological ligand for CLEC9a.

Where binding occurs, the method may further comprise the step of identifying the test substance.

It is believed that the ligand for CLEC9a is constitutively expressed in some or all healthy mammalian cells but is not accessible for interaction with CLEC9a while the cell remains healthy. Certain types of cell damage or cell death (especially when immunogenic, such as primary or secondary necrosis) cause the ligand to be exposed in such a way that it becomes accessible for interaction with CLEC9a on dendritic cells.

Thus, the test substance may be an intracellular component of a mammalian cell (e.g. a healthy mammalian cell, not infected by an intracellular parasite or pathogen). It may comprise or consist of a protein, carbohydrate, lipid or nucleic acid. It may comprise more than one of these components, for example it may be a glycosylated protein comprising carbohydrate and lipid components, a lipid-anchored protein comprising lipid and protein (and optionally also carbohydrate) components, or a glycolipid comprising lipid and carbohydrate components.

It will be understood that the test substance may not comprise the entire molecule or substance which would be present in the mammalian cell under physiological conditions, but may comprise a portion thereof which is sufficient to interact with CLEC9a. For example the test substance may comprise an isolated domain, or even a peptide (e.g. of 5 to 10 amino acids, up to 20 amino acids, up to 50 amino acids, or up to 100 amino acids) from a cellular protein.

Typically the test substance will be from the same mammalian species as the CLEC9a (or portion thereof) which is present in the target substance.

The method may comprise the step of contacting the target substance with a sample (e.g. a liquid sample, such as an aqueous sample) comprising the test substance.

The target substance may be provided in solution (e.g. in an aqueous solution) or may be immobilised on a solid support.

The sample may comprise permeabilised mammalian cells. By "permeabilised" is meant that the plasma membrane has become permeable by diffusion to entities which would not normally be able to cross the plasma membrane (without being actively taken up by the cell). Dyes such as propidium iodide and TO-PRO3, to which the plasma membrane is not permeable under normal conditions, are conventionally used to test plasma membrane integrity/permeability. Thus the plasma membrane may be permeable to such substances. For example, it may be permeable to substances having a molecular weight of above 500 Da, above 1 kDa, above 10 kD, above 50 kDa, above 100 kDa, or even higher. The term "permeabilised" is used here to refer to cells which substantially retain their cellular architecture (apart from the increased permeability of the plasma membrane, and potentially other membranes within the cell) such that individual cells can still be distinguished (e.g. by microscopy). The terms "lysate", "extract" or "homogenate" may be used for preparations in which the architecture of the cell is disrupted to such an extent that individual cells can no longer be distinguished or are no longer present.

The permeabilised cells may be necrotic. Necrosis may be primary or secondary necrosis. Primary necrosis may be induced experimentally by (for example) irradiation (e.g. with ionising radiation such as UV light), serum deprivation, at least one freeze/thaw cycle, or by treatment with necrosis-inducing chemicals such as anthracyclines (such as doxorubicin and daunorubicin) and anthracenediones (such as mitoxantrone). Secondary necrosis occurs when cells induced to enter apoptosis are not phagocytosed by neighbouring cells and the plasma membrane subsequently becomes disrupted.

Alternatively, healthy cells may be directly permeabilised with an agent which disrupts or forms pores in the plasma membrane. Suitable permeabilising agents include pore-forming agents such as saponins, (e.g. beta-escin), which precipitate cholesterol, thus removing it from the membrane and increasing its permeability, various bacterial toxins such as cytolysins (e.g. streptolysin-O from *Staphylococcus aureus*) and alpha-toxin from *Staphylococcus aureus* and detergents such as Triton X-100, Brij-96, Tween, etc.

Optionally, the cells may be fixed, either before or after permeabilisation. Fixation before permeabilisation may be preferred to reduce the chance that the ligand will be lost from the cell (e.g. by diffusion) following permeabilisation. Fixation can be performed with an organic solvent such as acetone, methanol, ethanol or mixtures thereof (which generally remove lipids and dehydrates the cell, while precipitating the proteins on the cellular architecture) and/or with a cross-linking reagent such as formaldehyde (e.g. as formalin) or paraformaldehyde (which cross-link cellular components such as proteins etc via free reactive groups present on those cellular components, such as amino groups).

Where the sample comprises permeabilised cells, the method may comprise the step of determining the subcellular location at which binding of the target substance takes place, by detection of the target substance.

Detection may be direct or indirect. For example the target substance may comprise a label, and the method may comprise the step of determining the subcellular location of the label. Alternatively the method may comprise the further step of contacting the target substance with a detection agent, which may be a binding agent capable of binding to the target substance. The detection agent may itself comprise a label. Detection may be achieved by any suitable technique, such as microscopy, e.g. confocal microscopy. For example, the label may be fluorescent.

Alternatively, the sample may be, or may comprise, a cell lysate, extract or a subcellular fraction of a mammalian cell. For example, it may comprise a whole cell lysate, or a subcellular fraction which is not exposed to the external environment in an intact healthy cell. For example, the sample may comprise an isolated cytoplasmic fraction, an isolated nuclear fraction, an isolated endoplasmic reticulum fraction, an isolated Golgi fraction, or an isolated mitochondrial fraction. "Isolated" in this context means separated from at least one other normal component of the intact cell (such as the plasma membrane). Subcellular organelles in such fractions, such as nuclei or mitochondria, may be intact or disrupted.

Following a positive binding reaction with a first sample, the first sample may be further fractionated to provide a second sample which lacks one or more components present in the first sample. The method may then be repeated. This may assist in identification of a test substance which binds to the target substance. This process may be repeated as often as desired, using progressively smaller fractions.

Additionally or alternatively the method may comprise the step of isolating a complex comprising the target substance and the test substance. This may be achieved by isolating a solid support (e.g. a bead) to which the target substance is bound. Alternatively a binding agent may be employed which is capable of binding to the target substance. the binding agent may be immobilised on a solid support. The target substance may comprise a member of a specific binding pair and the binding agent may comprise the second member of the specific binding pair. For example, the binding agent may be an antibody specific for the target substance. Alternatively, one of the binding agent and target substance may comprise an avidin/streptavidin moiety while the other comprises a biotin moiety.

The term "specific binding pair" is used to describe a pair of molecules comprising a specific binding member (sbm) and a binding partner (bp) therefor which have particular specificity for each other and which in normal conditions bind to each other in preference to binding to other molecules. Examples of specific binding pairs are antibodies and their cognate epitopes/antigens, ligands (such as hormones, etc.) and receptors, avidin/streptavidin and biotin, lectins and carbohydrates, and complementary nucleotide sequences.

To facilitate isolation, a single binding agent may be polyvalent, i.e. capable of binding simultaneously to more than one target substance. If the target substance is also polyvalent (i.e. capable of binding simultaneously to more than one binding agent of the same type) a cross-linked complex may be formed.

The skilled person will be well aware of suitable techniques, such as immunoprecipitation techniques, which may be employed.

For example, the target substance may be a soluble molecule comprising or consisting of the CLEC9a extracellular domain associated with (e.g. conjugated to or in a fusion protein with) an avidin monomer. The avidin monomers will tend to associate into tetramers, providing a binding agent comprising four CLEC9a domains and four avidin subunits. This construct may thus form a complex with a test substance in an assay as described here, which can then be isolated by contact with biotin, which may be present on a solid support such as a bead.

Alternatively the test substance may be immobilised on a solid support, such as a membrane, microtitre plate, or microarray chip. The support may be contacted with the target substance, and the location of any bound target substance determined.

It may be desirable to test a plurality of samples (e.g. different cellular fractions) suspected of containing a ligand for CLEC9a to see whether any of them do in fact contain a substance capable of binding to the target substance. Additionally or alternatively, it may be desirable to test a plurality of known substances (e.g. proteins) to see whether any of them is capable of binding to the target substance.

Thus a single solid support may comprise only one sample or test substance, or it may carry a plurality of samples or test substances each at a defined location on the support.

Depending on the format of the assay, the method may comprise the step of identification of the particular support on which a positive binding reaction takes place, or of the location on a support at which a positive binding reaction takes place. This may therefore reveal the nature of the sample which contains the test substance responsible for the positive reaction, or it may directly reveal the identity of the test substance.

Alternatively it may be possible to isolate a complex of the test substance and the target substance from the solid support and carry out further analysts to identify the test substance.

Whatever the format of the assay, where the test substance is a protein, it may be possible to use proteomic techniques to identify the test substance. This will typically combine mass spectroscopy and database interrogation. The test substance (or a complex of test and target substances) may be subjected to digestion with one or more proteases with known target cleavage sequences to yield peptides with known N- or C-terminal residues (depending on the particular protease used). The resulting peptides are then subjected to mass spectroscopy (e.g. MALDI-TOF) to determine their molecular weights. Suitable protein sequence databases can then be interrogated to identify proteins capable of giving rise to such peptides.

Alternatively the test substance may be displayed on the surface of a cell or virus. For example, a phage display technique may be used to display test substances or fragments thereof on the surface of a bacteriophage. Alternatively a cell may be engineered to display the test substance on its surface. Alternatively an interaction between the test substance and target substance may take place within a cell or a cell free expression system and may induce a detectable reaction such as expression of a reporter gene. An example of such a system is the yeast two-hybrid system, but the skilled person will be aware of other systems which rely on "bait-prey" interaction between two proteins to drive expression of a reporter gene. Such formats may be used to screen a population of nucleic acid molecules (e.g. a cDNA library) in order to identify a nucleic acid molecule which encodes a substance which can bind the target substance (if present), where a protein encoded by the nucleic acid is expressed in the cell or cell-free expression system. In such formats, the method may comprise the step of isolating (e.g. cloning) a nucleic acid responsible for a positive result, and determining the identity of the protein encoded by the nucleic acid.

Where the test substance is not a protein, other analytical techniques may be employed.

The invention will now be described in more detail, by way of example and not limitation, by reference to the accompanying drawings and examples.

DESCRIPTION OF THE DRAWINGS

FIG. 1 shows cDNA (SEQ ID NO: 1) and amino acid sequences for the human CLEC9a protein (SEQ ID NO: 2).

FIG. 2 shows cDNA (SEQ ID NO: 3) and amino acid (SEQ ID NO: 4) sequences for the mouse CLEC9a protein.

FIG. 5 illustrates the CD3sζNKRPI-CLEC9a chimera generated in this work, showing the domains presents in the chimeric molecule with the extracellular domain of CLEC9a, the transmembrane domain from NKRP I and the cytoplasmic domain from CD3ζ (SEQ ID NO: 5).

FIG. 12 shows targeting of CD11c+CD8+ in vivo using anti-CLEC9a-S1 mAb. S1 conjugated anti-CLEC9a or isotype control mAb (5 μg) were injected i.v. and the splenocytes processed the following day as indicated under Methods. A and B. CD11c positive and negative splenocytes were cultured for four days with CFSE-labelled OT-I cells. A. CFSE profiles of OT-I cells in the presence of $25 \times 10^3$ targeted CD11c− or CD11c+ splenocytes. B. Left panel: absolute number of OT-I cells per well. Right panel: IFN-γ production in the supernatants of expanded OT-I cells.

C and D. CD11c+ splenocytes in S1-anti-CLEC9a targeted mice were sorted as CD11c+B220−CD8+ (CD8+ DC), CD11c+B220−CD4+ (CD4+ DC) and CD11c+B220−CD4−CD8− (DN DC) and cultured three days with CFSE labelled OT-I cells. C. CFSE profiles of OT-I cells in the presence of $25 \times 10^3$ targeted CD8+, DN, CD4+ DC. D. Left panel: absolute number of OT-I cells per well. Right panel: IFN-γ production in supernatants at the end of the culture.

Figure 13A:
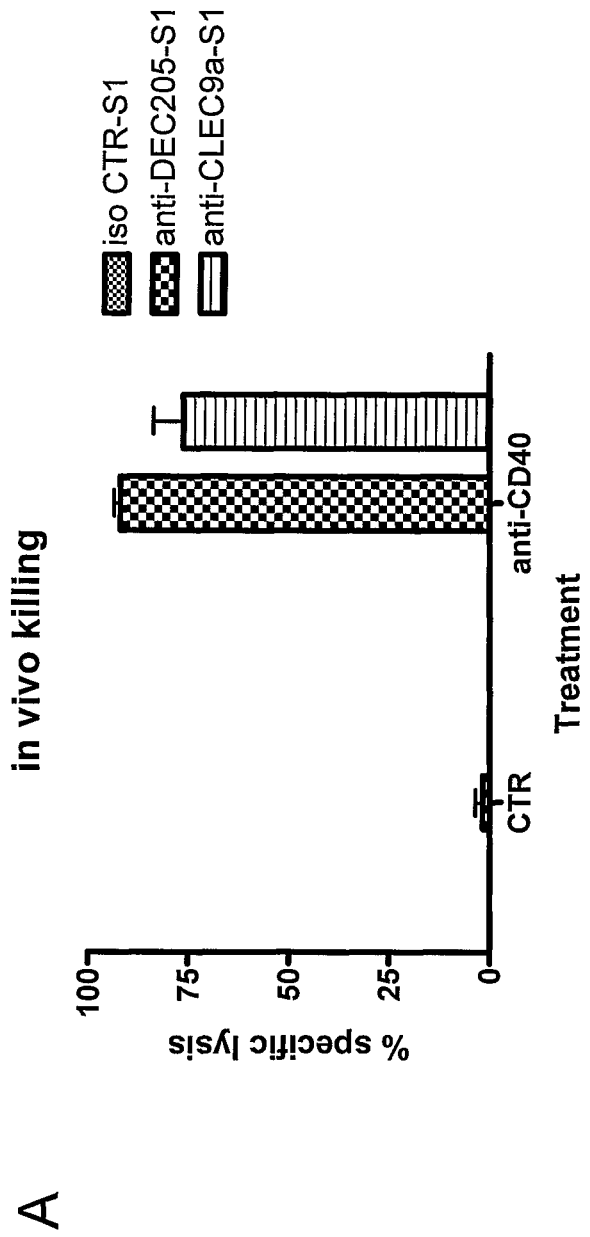
Figure 13B:
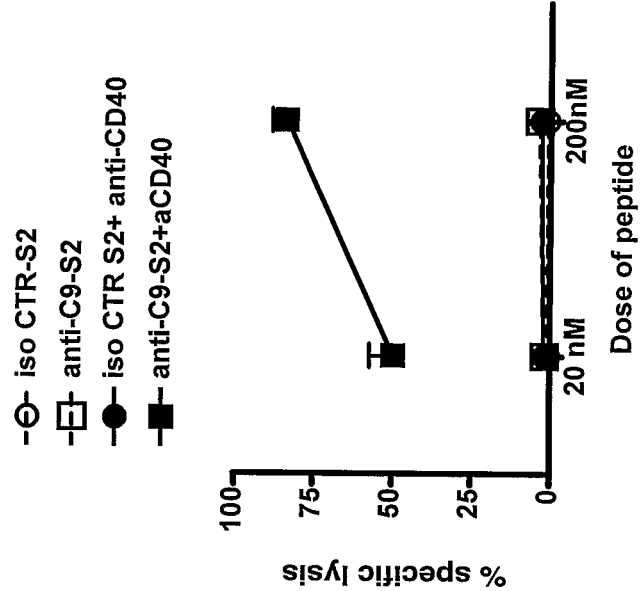

FIG. 13 shows induction of CTL immunity by targeting using anti-CLEC9a mAb. A: S1 conjugated anti-CLEC9a or isotype control mAb were injected s.c. together or not with anti-CD40 as indicated under Methods. Five days later target cells (congenic CD45.1) loaded with 20 nM (0.03 μM CFSE), 200 nM (0.3 μM CFSE) of SIINFEKL or not loaded with peptide (3 μm CFSE) were i.v. injected. Results are expressed as arithmetic mean±SEM of % specific lysis of the high dose of peptide in the in vivo killing assay (n=5, p<0.001 of DEC205 and CLEC9a groups compared to control. One way ANOVA). B: Results of a similar experiment using S2 conjugated to isotype control or anti-CLEC9a, administered with or without anti-CD40.

Figure 14:
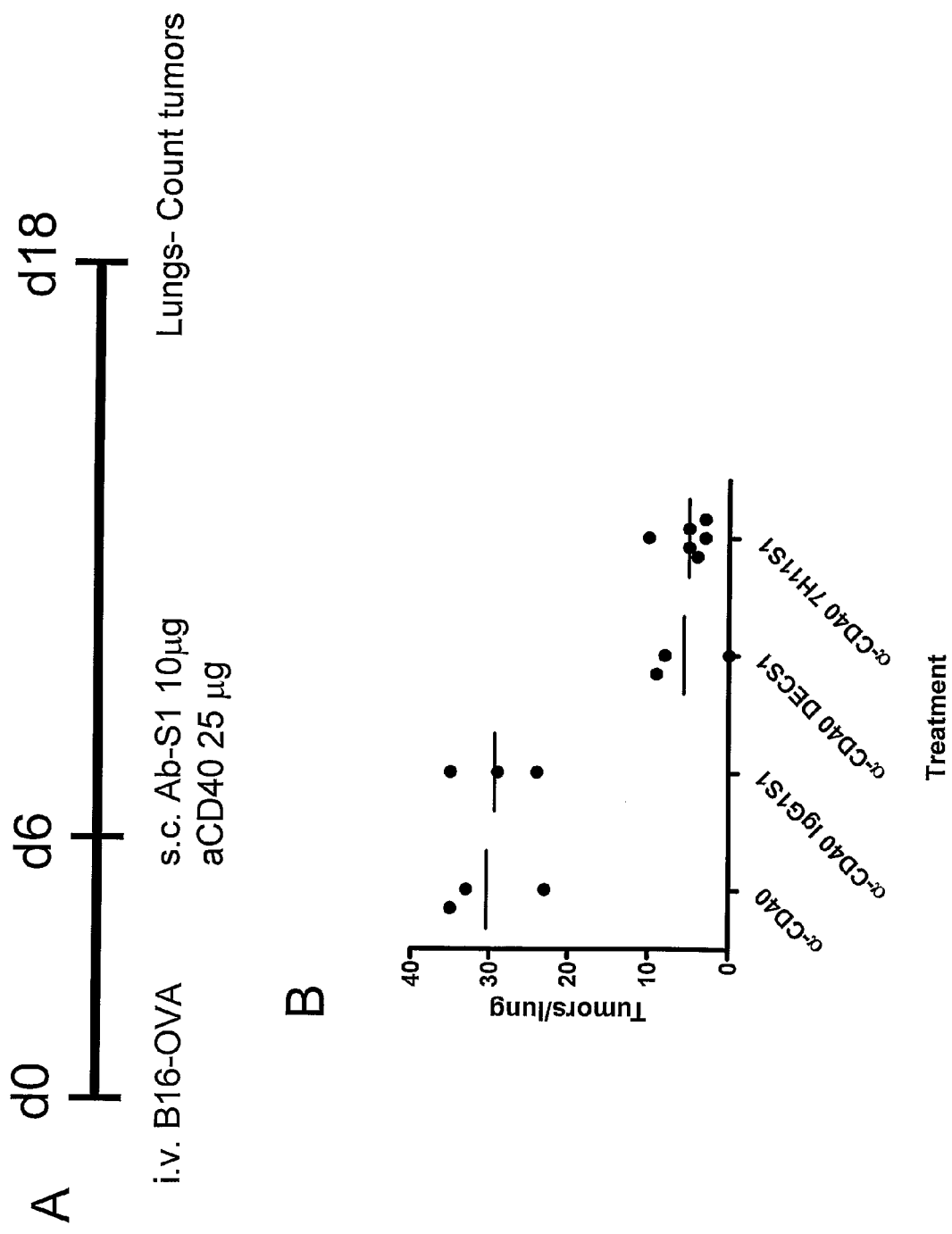

FIG. 14 shows the therapeutic effect of anti-CLEC9a+anti-CD40 in the treatment of B16 melanoma. A. time course of a tumor therapy experiment using B16-OVA-GFP melanoma cells. Tumor cells (2×10⁵) were injected at day 0, treatment of Ab-S1+anti-CD40 performed at day 6, and lungs extracted and tumors counted at day 18. B. Tumor counts in each mouse in one representative experiment are shown. The reduction in tumor burden is significant ($p<0.001$, one way ANOVA) with anti-CLEC9a or anti-DEC205 plus anti-CD40.

Figure 15:
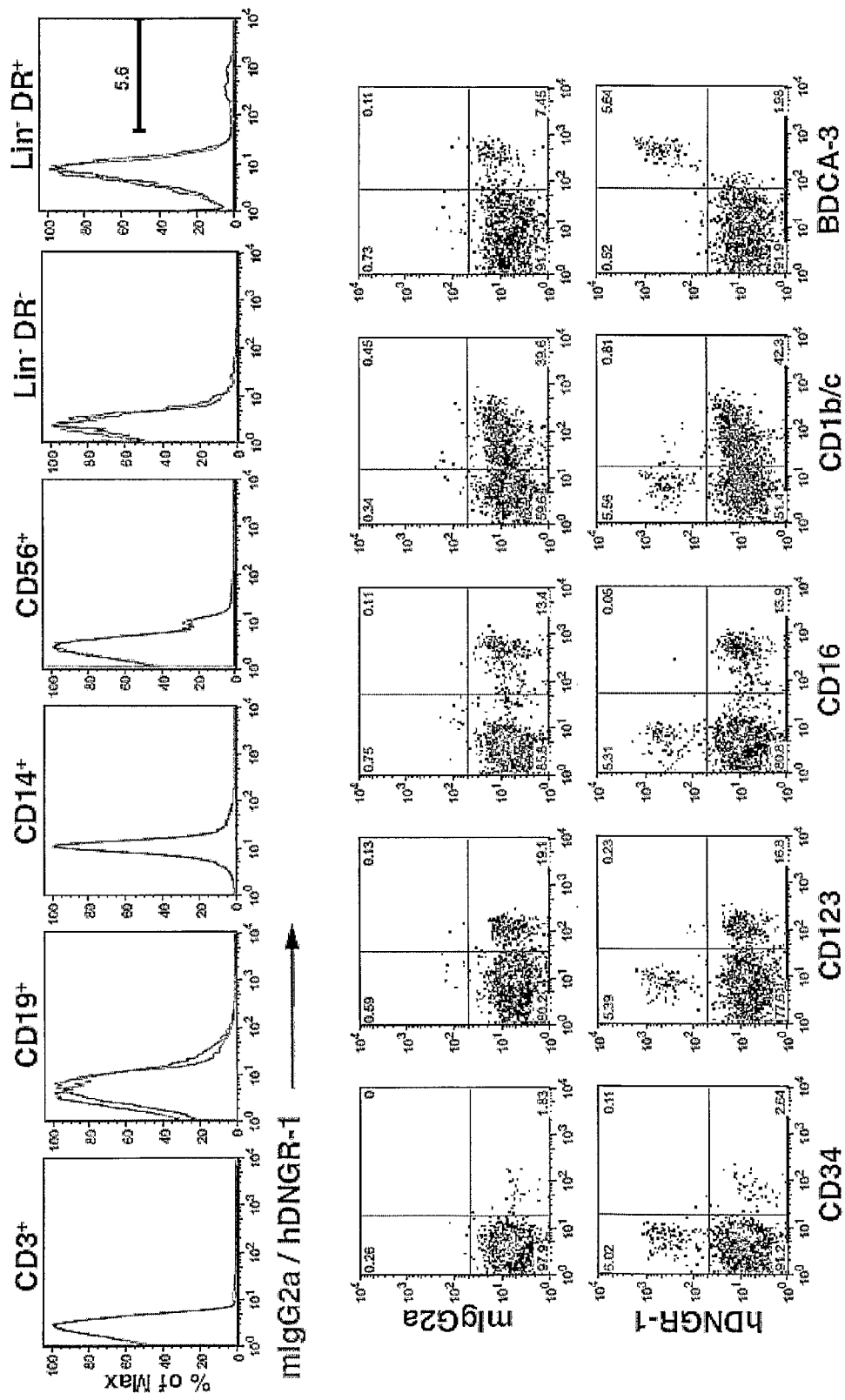

FIG. 15 shows that human CLEC9a expression is restricted to BDCA-3+ blood DC. (A) Human PBMC were stained with anti-hCLEC9a (8F9) or an isotype-matched control antibody (mouse IgG2a) and counterstained for various blood leukocyte markers. Histograms show CLEC9a staining on T cells, B cells, monocytes, NK cells, lineage-negative HLA-DR− cells and lineage-negative HLA-DR+ cells. Number indicates the percentage of hCLEC9a+ cells in the latter fraction. (B) PBMC from (A) were gated on lineage-negative HLA-DR+ cells. Dot plots show staining with anti-CLEC9a or isotype-matched control mAb against various blood DC subset markers. Numbers represent % cells in each quadrant. Specific staining is seen only on BDCA-3+DC. One representative experiment out of four.

Figure 16:
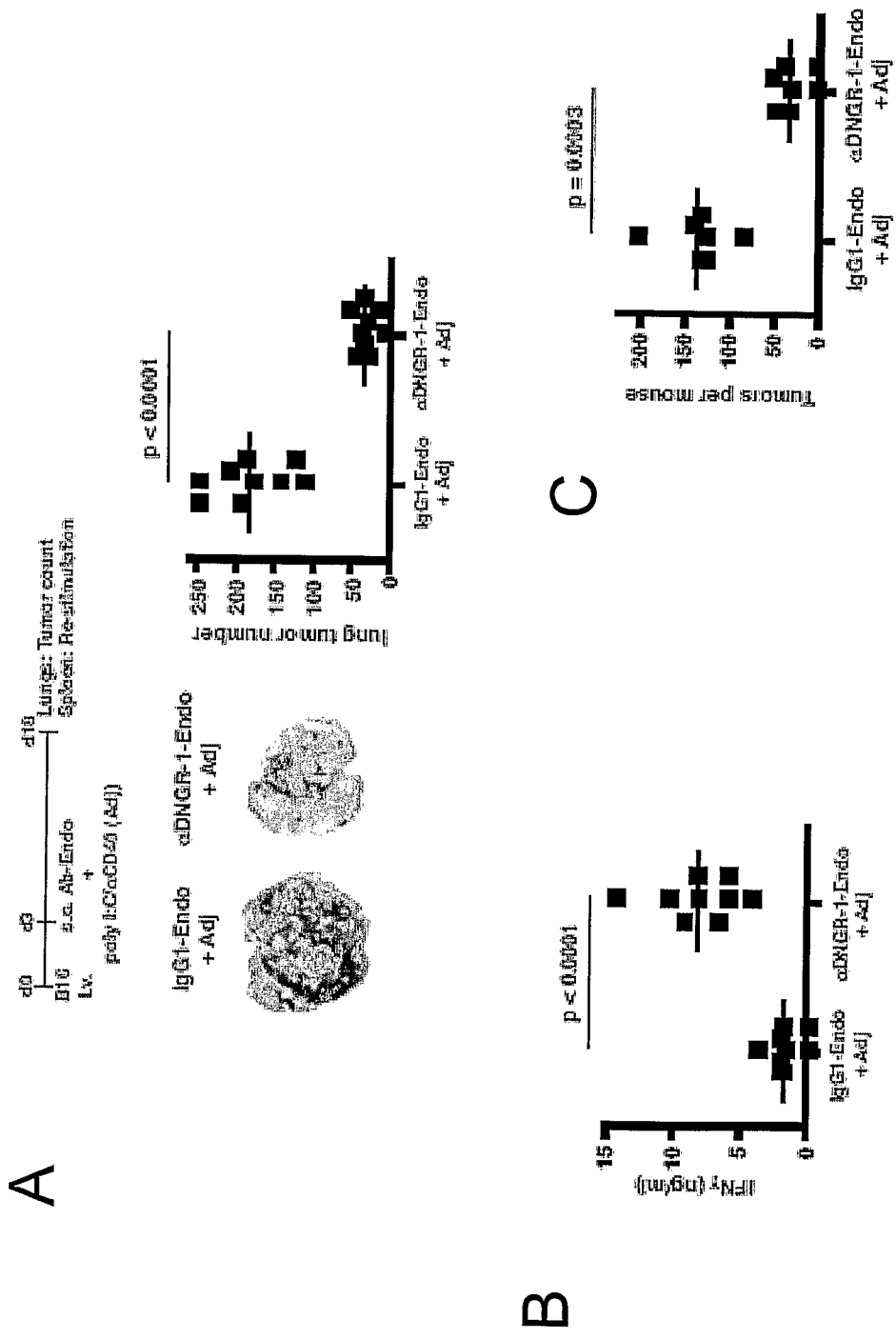

FIG. 16 shows immunotherapy of B16 melanoma via targeting of tumor antigens to CLEC-9a. (A) Tumor therapy experiments were carried out as depicted (upper left) using peptides encompassing known epitopes of melanocyte differentiation endogenous antigens ("Endo": gp100, TRP-1 and TRP-2) covalently coupled to anti-CLEC9a or to an isotype-matched control antibody. Poly I:C+anti-CD40 was used as adjuvant. Left lower panel shows representative pictures of lungs from mice treated as indicated. Right panel shows quantification of lung tumors in each mouse. Data are pooled from two independent experiments (n=9 mice/group) and each point represents one mouse. (B) Splenocytes from individual mice in (A) were restimulated in vitro with the melanocyte differentiation antigen peptides used for immunization (10 μM). IFN-γ levels after 2 d of culture are shown. Data pooled from two independent experiments (n=9 mice/group). p values were calculated using the Mann Whitney U test. (C) Experiments were carried out as in FIG. 16 except that the vaccine was given one day prior to infusion of B16 cells. Data show the number of lung tumors per mouse. Data are pooled from two independent experiments (n=7 mice/group) and each point represents one mouse. p values were calculated using the Mann Whitney U test.

Figure 17:
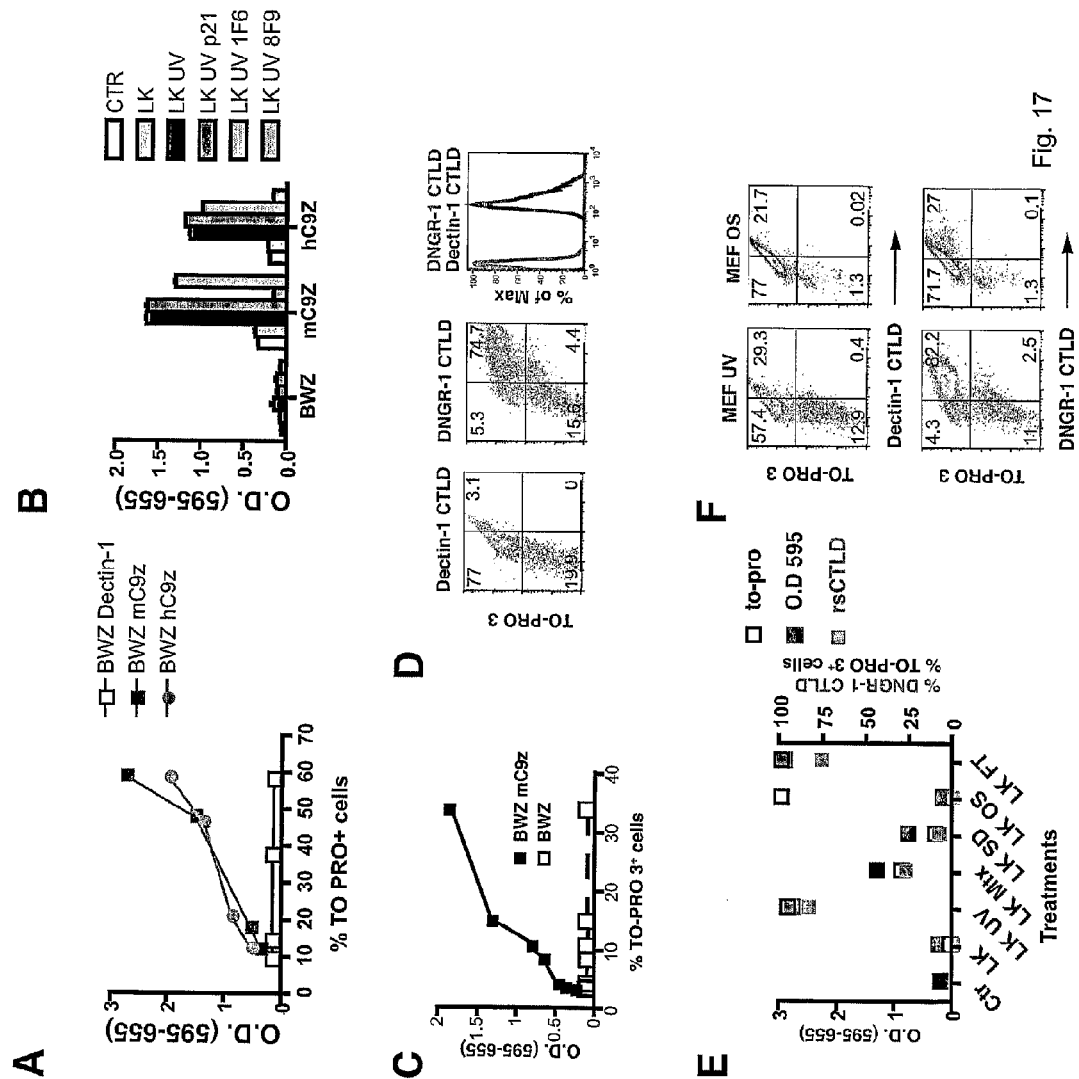

FIG. 17 shows that CLEC9A binds a ligand on dying/dead cells. (A) Basal activation of BWZ-mouse and human CLEC9Aζ reporter correlates with number of dead TO-PRO3⁺ cells. BWZ cells expressing a reporter for NFAT coupled to LacZ and stably expressing a chimeric molecule with the extracellular domain from mouse or human CLEC9A or control Dectin-1 and the intracellular tail from CD3 were generated for screening for natural ligands of CLEC9A. Different cell concentrations were allowed to grow for two days, showing different degrees of overgrowth and increase of dead cells in the culture tracked by TO-PRO 3 staining. The same amount of living BWZ cells was then plated in fresh medium and, after overnight culture, NFAT activity in BWZ cells was measured in a colorimetric assay as indicated in Methods.

(B) UVC-treated dead cells expose a ligand for CLEC9A. Live MEFs (Ctrl) or MEFs treated with UVC and left 24 h to induce cell death were cultured with BWZ NFAT reporter cells expressing the chimeric mouse CLEC9A-ζ, human CLEC9A-ζ, and Dectin-1-ζ. Where indicated, monovalent Fab fragments of control (p21) or anti-mCLEC9A (1F6) or anti-hCLEC9a (8F9) were added to the culture. NFAT activity in BWZ cells was measured as in (A).

(C) Dose response in UV-treated cells. LK cells were exposed to different doses of UVC as indicated in Methods and left 24 h to induce cell death before culturing with BWZ cells expressing mCLEC9A-ζ chimera or control BWZ. NFAT activity in BWZ cells was measured as in (A).

(D) The recombinant soluble C-Type Lectin Domain (rsCTLD) of CLEC9A selectively recognizes a molecule exposed by TO-PRO3⁺ dead cells. PE-tetramers of the rsCTLD of CLEC9A or Dectin-1 (as a control) were used for staining of UV irradiated immortalized MEF (dot plots). Histograms show staining of zymosan, positive for Dectin-1 rsCTLD.

(E) Different death-inducing treatments trigger BWZ-CLEC9Aζ reporter cells. BWZ-CLEC9Aζ cells were cultured overnight alone (Ctrl) or with LK cells untreated (LK) or treated with UVC (UV), mitoxantrone (Mtx), serum deprivation (SD), osmotic shock (OS) or freeze and thaw (FT). BWZ reporter activity (left y axis) and to-pro 3⁺ and CLEC9A rsCTLD⁺ frequency in LK cells when starting the co-culture (right y axis) are depicted.

(F) Staining of dead MEFs using PE-tetramers of CLEC9A rsCTLD. MEFs were treated with UV and left 24 h or treated with osmotic shock (OS) before staining.

(A)-(F) one representative experiment shown of at least three performed.

Figure 18:
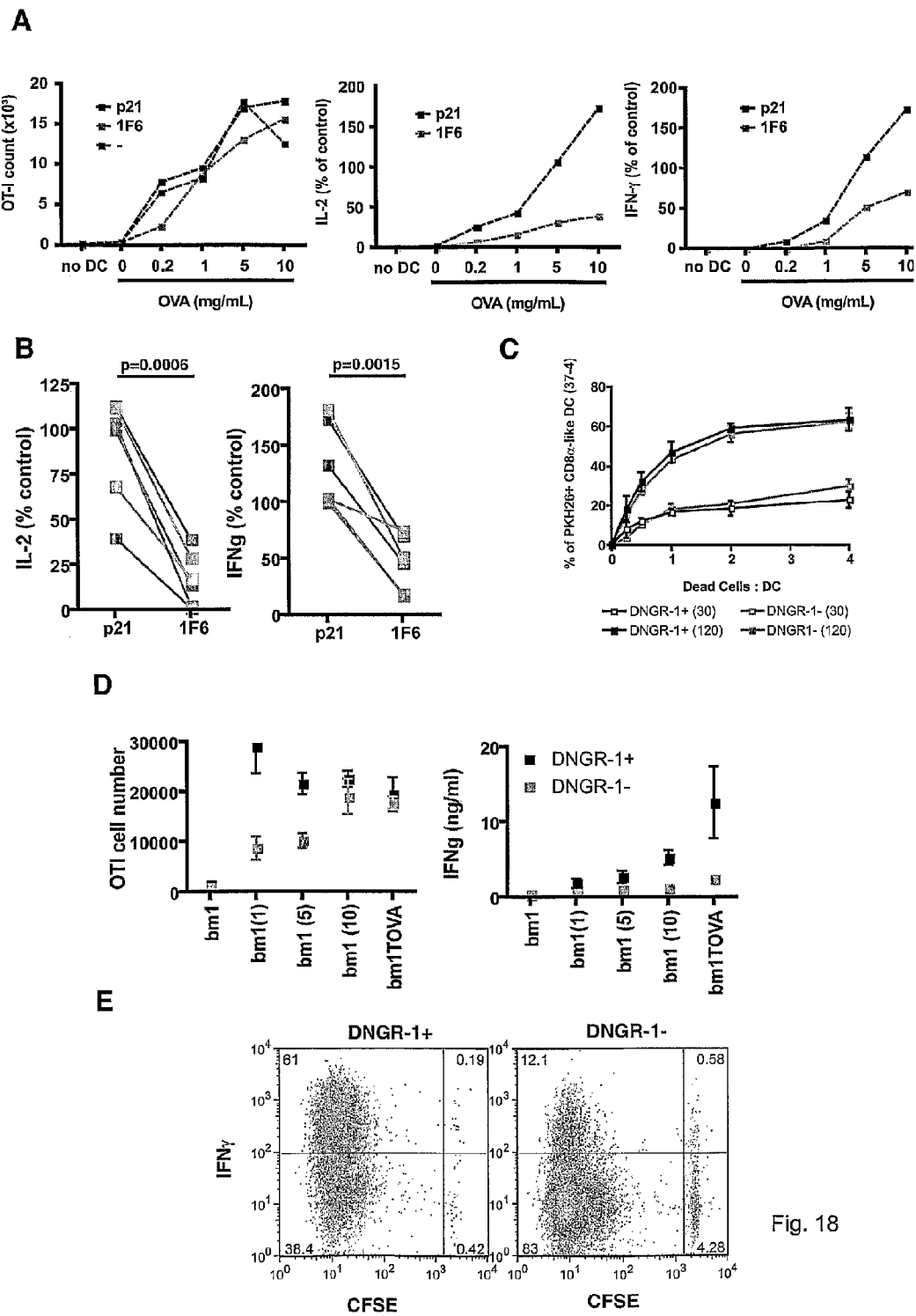

FIG. 18 shows that CLEC9A is involved in cross-priming to dying cells by CD8α⁺ DC in vitro.

(A), (B) Blockade of CLEC9A results in impaired cross-priming of OT-I cells to dead cell associated antigen. (A) OT-I OVA-specific T cells were cultured with CD8α-like Flt3L BMDC stimulated with OVA-loaded dead bm1 splenocytes in the presence or absence of anti-CLEC9A Fab (1F6) or control Fab (p21). Three days later, proliferation (absolute numbers of OT-I cells), IL-2 and IFNγ production (% production relative to untreated control) were measured. One representative experiment out of six is shown. (B) The average IL-2 and IFNγ production for the six independent experiments performed is shown as % production by untreated control for anti-CLEC9A Fab (1F6) or control Fab (p21).

(C) CLEC9A⁻/⁻ and WT CD8α-like Flt3L BMDC have the same ability to capture dying cell material. WT or CLEC9A⁻/⁻ CD8α-like Flt3L BMDC were incubated for 2 h with PKH26-labelled and UVC-treated bm1 splenocytes at different ratios. Binding (4° C.) and binding+uptake (37° C.) were then quantified by flow cytometry for each type of DC.

(D) Impaired expansion and differentiation to effector OT-I cells after incubation with CLEC9A⁻/⁻ Flt3L BMDC stimulated with OVA-expressing or OVA-loaded bm1 dead cells. CLEC9A⁻/⁻ Flt3L BMDC were cultured with UVC-treated OVA-loaded bm1 splenocytes or UVC-treated OVA-expressing bm1 MEFs. OVA-specific OT-I T cells were then added and, after 3 days of co-culture, absolute numbers of OT-I cells (left panel) or IFN-γ (right panel) were measured. Results show the average±SEM of two mice per group. One representative experiment out of three performed is shown.

(E) Impaired differentiation of OT-I cells after incubation with CLEC9A⁻/⁻ Flt3L BMDC stimulated with OVA-expressing UV-dead bm1 MEFs as in (D). One representative mouse per group out of four analyzed using the same assay is shown.

Figure 19:
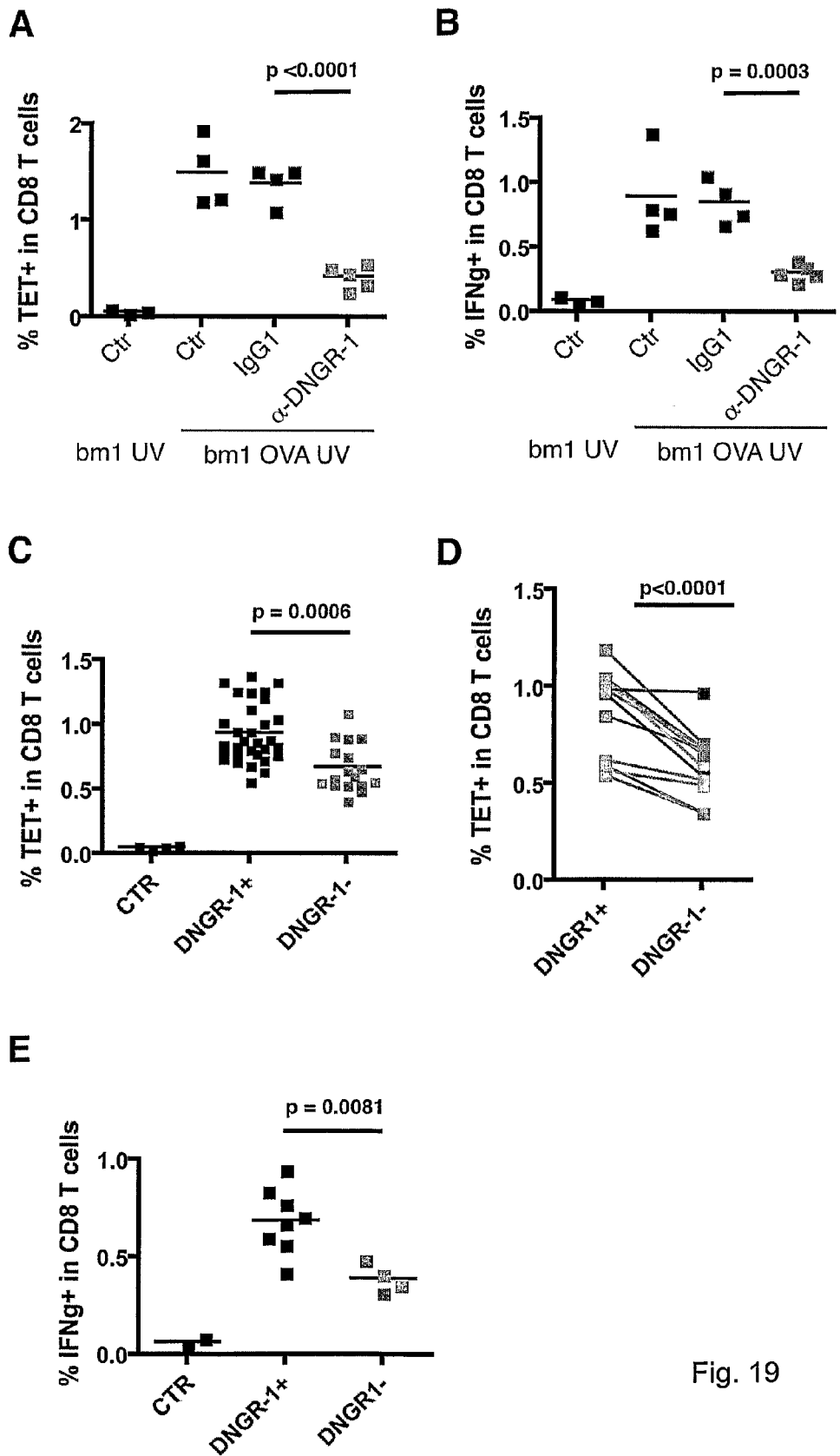

FIG. 19 shows that CLEC9A senses immunogenic cell death to promote crosspriming in vivo.

(A), (B) Blockade of CLEC9A reduces crosspriming to dead cell associated antigen in vivo. Mice untreated or treated with anti-CLEC9A (1F6, 400 μg/mouse) or isotype control (rat IgG1) were immunised with i.v. with 0.75×10⁶ UV-irradiated bm1 MEFs expressing a truncated OVA-GFP fusion protein. Six days later H2K$^b$-OVA peptide tetramer positive cells (A) and IFNγ production in response to SIINFEKL ex vivo (B) were measured as readout for induction of CD8$^+$ T cell effector response arising from the endogenous repertoire. Individual mice and average for one representative experiment (out of three) is shown.

(C)-(E) CLEC9A deficiency reduces crosspriming to dead cell associated antigen in vivo. CLEC9a–/– mice or control littermates were immunised as in (A). The frequency of OVA-specific endogenous CD8+ T cells (C-D) was quantified as in (A). (C) each dot represents an individual mouse pooled from six independent experiments and normalized as indicated under Methods. (D) the average of tetramer-positive cells is represented in each litter for CLEC9a$^{-/-}$ and CLEC9a$^+$ mice. (E) IFNγ production in response to SIINFEKL ex vivo was measured as in (B). Individual mice and average for one representative experiment (out of three) is shown.

Figure 20:
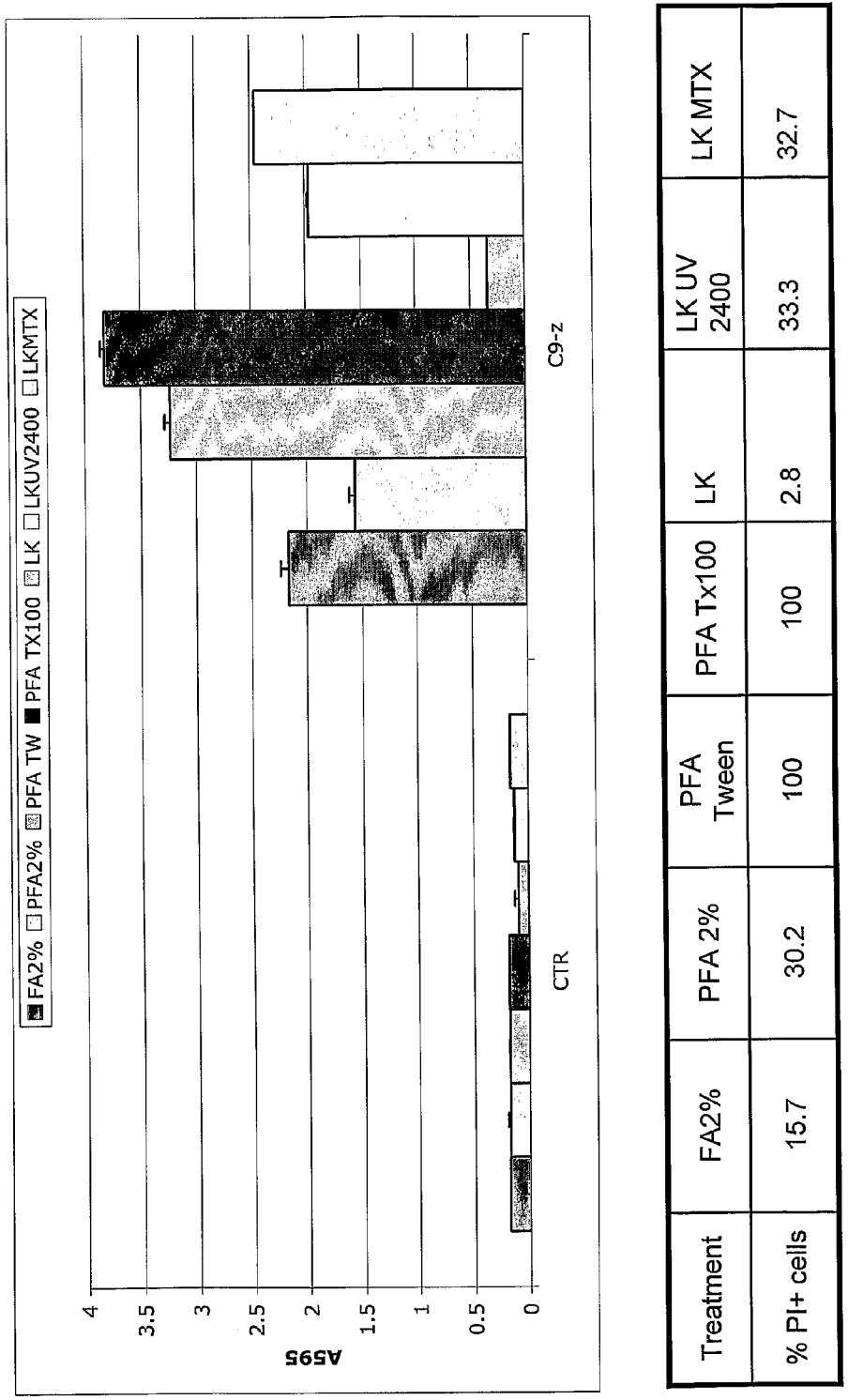

FIG. 20 shows that ligand for CLEC9a is exposed following fixation/permeabilization.

LK cells were fixed with 2% formaldehyde or 2% paraformaldehyde, and permeabilized or not with Tween (0.5%) and Tx-100 (0.5%). Cells were extensively washed and percentage of permeable cells quantified using To-pro 3. Fixed or fixed-permeabilized cells were co-cultured with BWZ NFAT reporter cells expressing the chimeric mouse CLAC9a-CD3ζ or control and NFAT activity measured.

Figure 21:
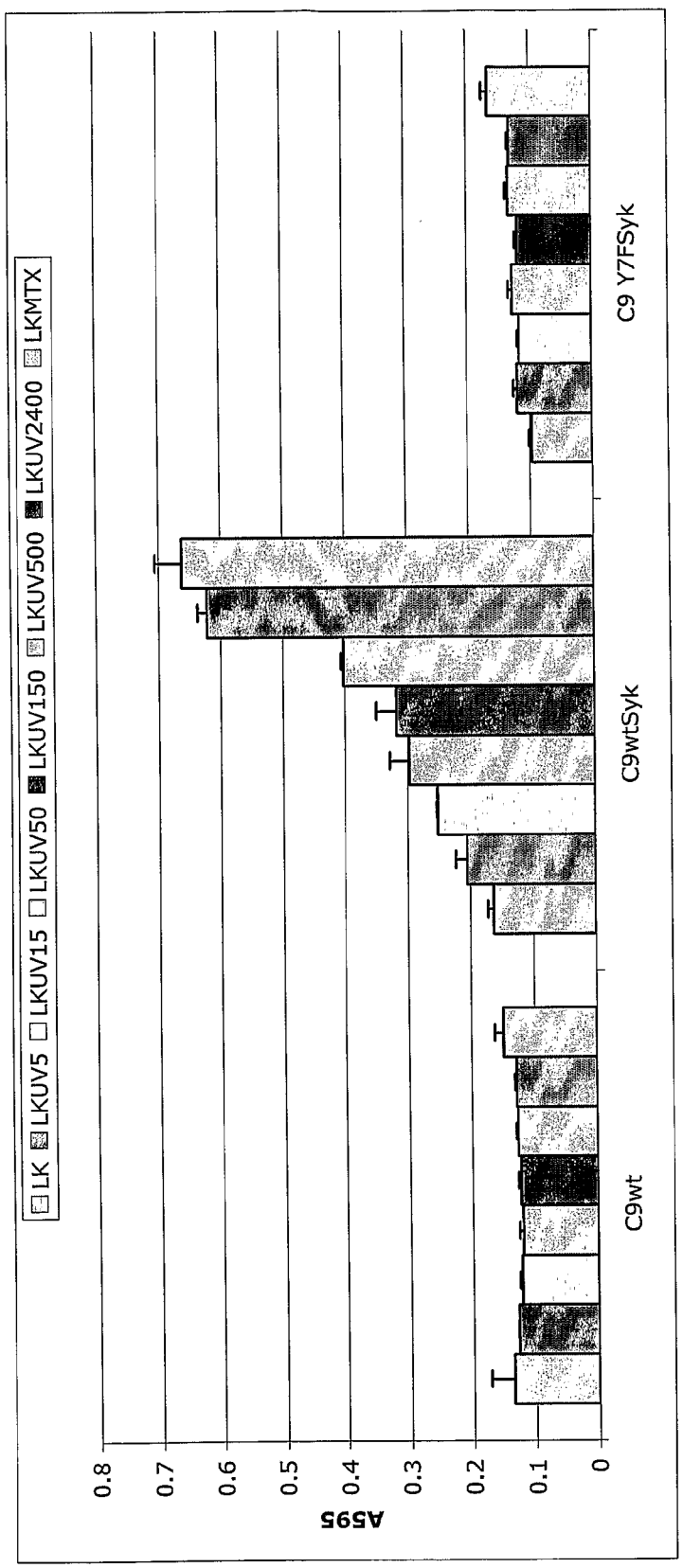

FIG. 21 shows that dead cells signal through CLEC9a wt cytoplasmic tail.

LK cells were exposed to different doses of UVC as indicated in Methods and left 24 h to induce cell death before culturing with B3Z cells stably transfected with CLEC9a wt or CLEC9a with the Tyr7 mutated to Phe (Y7F) and co-expressing or not Syk. NFAT activity in B3Z cells was measured as described under Methods.

Figure 22:

FIG. 22. Both Fab monovalent and full bivalent anti-CLEC9a antibodies block dead cell signals through CLEC9a.

LK cells treated with UVC and left 24 h to induce cell death were cultured with B3Z cells stably transfected with CLEC9a wt or CLEC9a with the Tyr7 mutated to Phe (Y7F) and co-expressing Syk or B3Z-Dectin-1-ζ as control. Where indicated, monovalent Fab fragments of control (p21) or anti-CLEC9a (1F6) or full bivalent antibodies, including isotype controls (rat IgG1, rat IgG2a) and anti-mCLEC9a (1F6, 397, 7H11) were added to the culture. NFAT activity in B3Z cells was measured as described under Methods.

Figure 23:
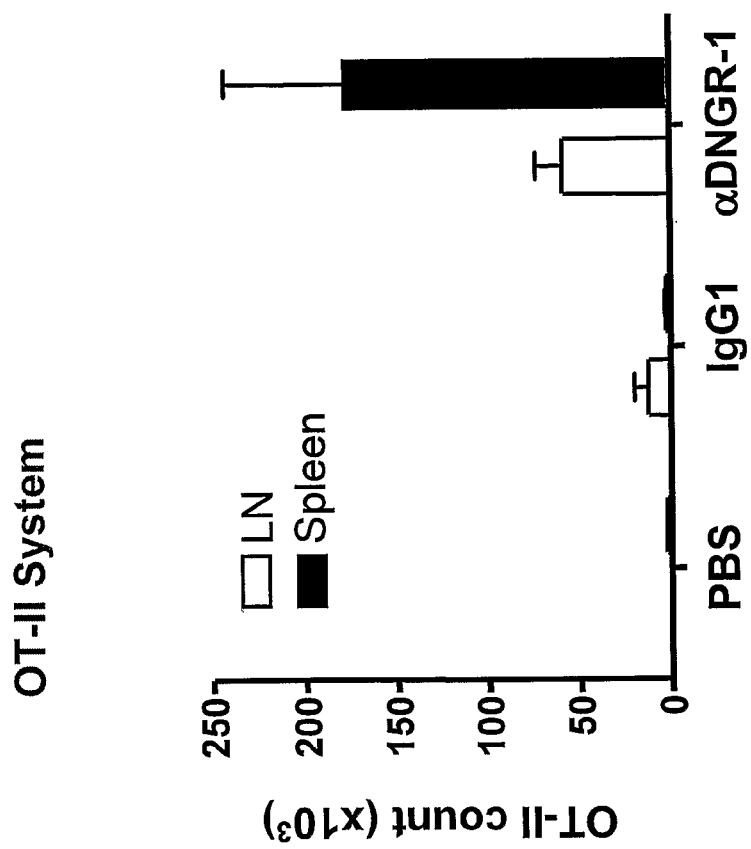

FIG. 23 shows proliferation of OVA-specific OT-II CD4 T cells in response to anti-CLEC9a-OVA323-339. Naive CFSE labelled OT-II CD4 T cells were transferred i.v. into C57BL/6 mice. One day later OVA323-339 peptide was inoculated s.c. in the paw either conjugated to anti-CLEC9a or to isotype control antibody. Spleen and draining lymph nodes were collected three to four days later and in vivo proliferation of OT-II cells was tracked following CFSE dilution. Absolute numbers of OT-II cells are shown, normalized between samples.

Figure 24:
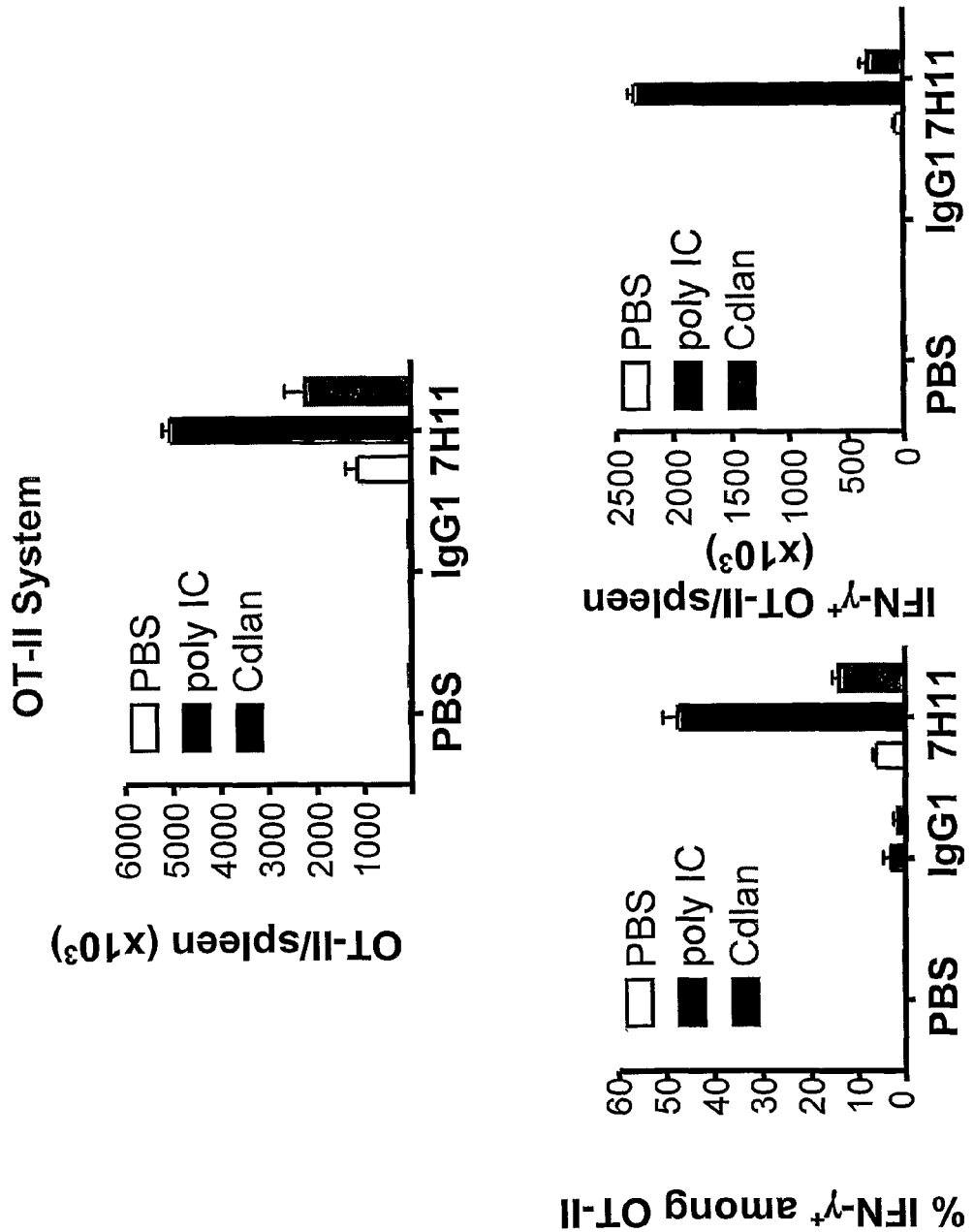

FIG. 24 shows that addition of adjuvant during the targeting in vivo induces a strong Th1 response. Targeting in vivo in the presence or absence of adjuvant (OT-II system). Mice were treated as in FIG. 23. Upper panel: Absolute number of OVA-specific CD4 T cells (after normalization). Lower panels: IFN-γ production in the OT-II CD4 T cells population expressed as percentage (left) or absolute number (right, after normalization). The effects on proliferation and differentiation observed in the presence of poly I:C are not restricted to this adjuvant. Curdlan has a similar effect.

Figure 25:
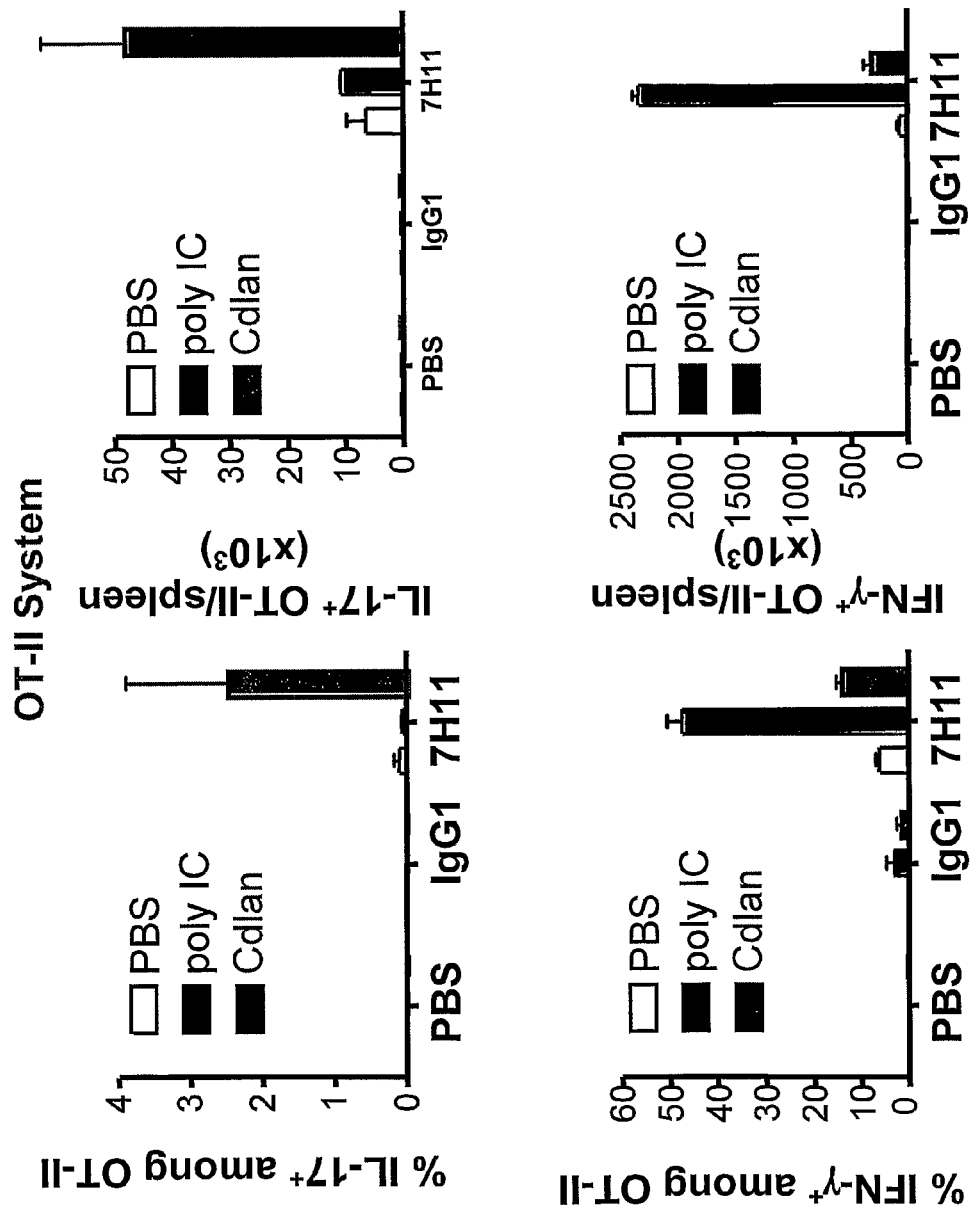

FIG. 25 shows that the CD4 T cell response can be modulated by the type of adjuvant/immunomodulator co-injected with the targeting reagent. Targeting in vivo in the presence or absence of adjuvant. OT-II system was performed as in FIG. 24. Upper panels: IL-17 production in the OT-II CD4 T cells population expressed as percentage (left) or absolute number (right, after normalization). Curdlan, a Dectin-1 agonist, acted as a strong adjuvant for Th17 polarization when administered with the targeted antigen.

Figure 26:
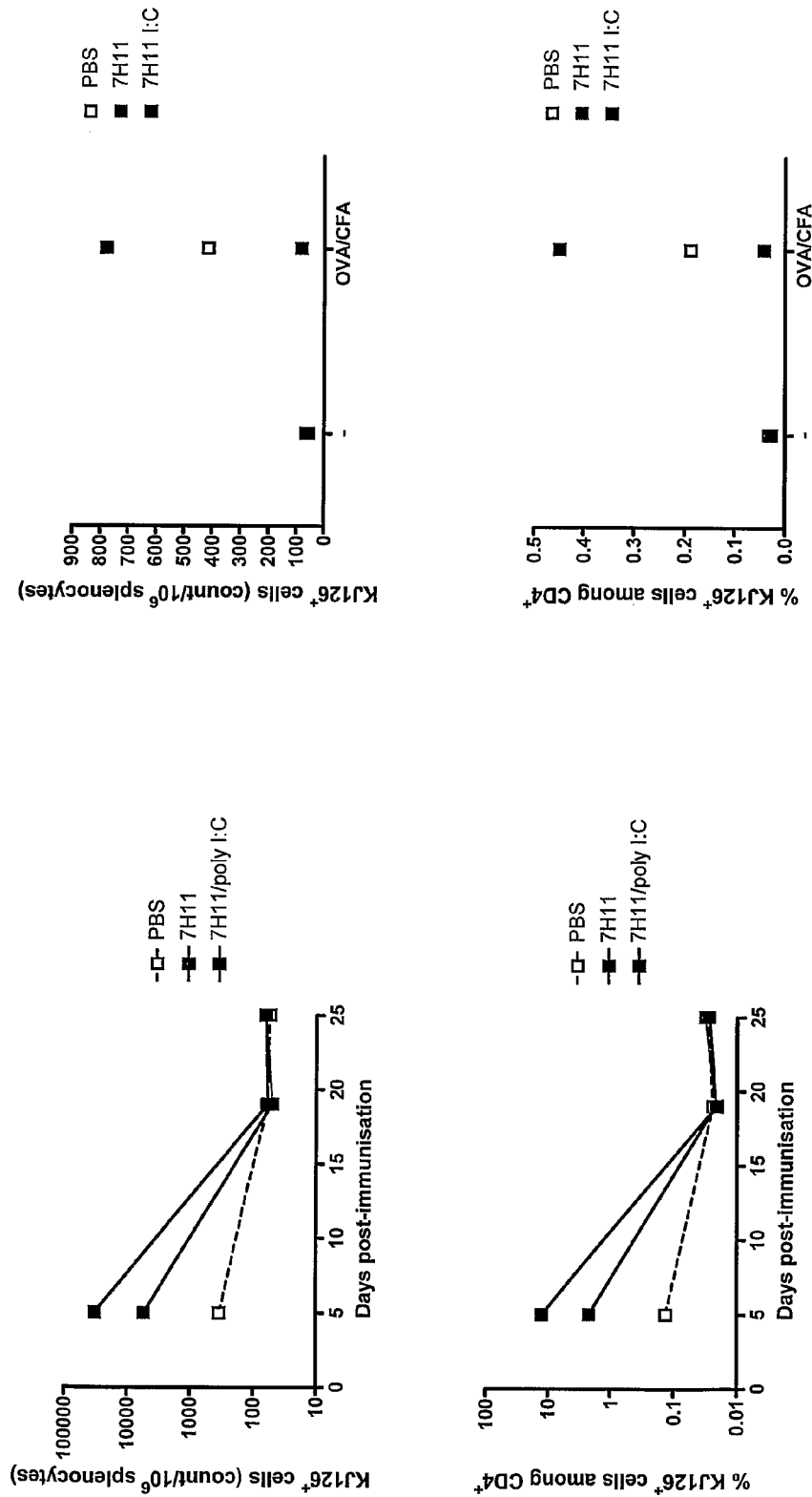

FIG. 26 shows that targeting in the absence of adjuvant leads to antigen-specific tolerance. Naive OVA-specific DO.11.10 CD4 T cells were transferred into BALB/c mice. One day later, anti-CLEC9a-OVA 323-339 was inoculated s.c. in the paw with or without adjuvant (poly I:C). At different time-points after immunisation, the size of the splenic DO.11.10 compartment was determined by flow cytometry using the KJ.126 clonotypic antibody. Results are expressed as absolute number of OVA-specific KJ.126 cells (after normalization) or as percentage of KJ.126$^+$ cells among the CD4 T cell compartment. At day 20, half of the mice were challenged s.c. with OVA in Complete Freund's Adjuvant. 5 days later, the DO.11.10 response was monitored by flow cytometry. In mice injected only with PBS at day 0, the remaining DO.11.10 cells are still responsive as shown by their strong proliferative responses after rechallenge. A stronger response was detected in mice previously injected with anti-CLEC9a+adjuvant, showing that this first immunization probably led to the generation of memory cells. In contrast, no response was detected in mice firstly immunized with anti-CLEC9a alone, showing that the remaining cells were tolerant for the antigen

DETAILED DESCRIPTION OF THE INVENTION

CLEC9a

CLEC9a is a C-type lectin expressed on dendritic cells. As used in this specification, the term CLEC9a is intended to embrace the human protein (nucleic acid and protein sequences as shown in FIG. 1), the murine protein (nucleic acid and protein sequences shown in FIG. 2), their homologues (especially orthologues) in other species, and variants and derivatives thereof which retain CLEC9a activity. Such variants and derivatives preferably have at least about 30% sequence identity, more preferably at least about 35%, 40%, 45%, 50%, 55%, 60%, 65%, 70%, 75%, 80%, 85%, 90% or 95% sequence identity to the human protein sequence shown in FIG. 1, or at least about 35% identity, more preferably at least about 40%, 45%, 50%, 55%, 60%, 65%, 70%, 75%, 80%, 85%, 90% or 95% identity to the extracellular domain of the human protein sequence shown in FIG. 1.

In particular, conservative substitutions in the CLEC9a sequence (as compared to the reference sequences) may be particularly well tolerated, without substantial effect on function.

A conservative substitution may be defined as a substitution within an amino acid class and/or a substitution that scores positive in the BLOSUM62 matrix.

According to one classification, the amino acid classes are acidic, basic, uncharged polar and nonpolar, wherein acidic amino acids are Asp and Glu; basic amino acids are Arg, Lys and His; uncharged polar amino acids are Asn, Gln, Ser, Thr and Tyr; and non-polar amino acids are Ala, Gly, Val, Leu, Ile, Pro, Phe, Met, Trp and Cys.

According to another classification, the amino acid classes are small hydrophilic, acid/acid amide/hydrophilic, basic, small hydrophobic and aromatic, wherein small hydrophilic amino acids are Ser, Thr, Pro, Ala and Gly; acid/acidamide/hydrophilic amino acids are Asn, Asp, Glu and Gln; basic amino acids are His, Arg and Lys; small hydrophobic amino acids are Met, Ile, Leu and Val; and aromatic amino acids are Phe, Tyr and Trp Substitutions which score positive in the BLOSUM62 matrix are as follows:

| | Original Residue | | | | | | | | | | | | | | | | | | | |
|---|---|---|---|---|---|---|---|---|---|---|---|---|---|---|---|---|---|---|---|---|
| | C | S | T | P | A | G | N | D | E | Q | H | R | K | M | I | L | V | F | Y | W |
| Substitution | — | T<br>A<br>N | S | — | S | — | S<br>D<br>H | N<br>E<br>K | D<br>Q<br>K | E<br>R<br>K | N<br>Y | Q<br>Y<br>R | E<br>Q<br>R | I<br>L<br>V | M<br>L<br>V | M<br>I<br>V | M<br>I<br>V<br>L | Y<br>W | H<br>F<br>W | F<br>Y |

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. % identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

A CLEC9a agonist is an agent capable of inducing CLEC9a activity, typically by binding to its extracellular domain (ECD) and inducing intracellular signalling via its intracellular domain. Signalling may involve one or more of binding of Syk to the intracellular domain, phosphorylation (and hence activation) of Syk, and/or phosphorylation of Erk and/or activation of NFAT. An illustrative assay is described in the Examples, using B3Z cells transfected with Clec9a and Syk. The skilled person will understand that a chimeric protein having the extracellular domain of Clec9a and an intracellular domain derived from a different protein may also be used to assay for Clec9a agonist activity. The transmembrane domain may be from Clec9a, the same protein as the intracellular domain, or from another protein. An example is the CD3ζ-NKRP1-CLEC9a illustrated in FIG. 5 and described in more detail in the Examples.

A CLEC9a antagonist is an agent capable of inhibiting or blocking CLEC9a function. For example, it may prevent its normal expression, its ability to bind physiological CLEC9a ligand, its ability to internalise (endocytose) molecules to which it has bound, its ability to signal intracellularly (see above), or the ability of its ECD to interact with binding partners (ligands or receptors), e.g. on other cells. Another possible mechanism of action for an antagonist might be to promote internalisation of Clec9a without inducing significant intracellular signalling, and so reduce the pool of Clec9a available at the cell surface to interact with natural ligands or other agonists. Antagonists include binding agents having affinity for CLEC9a such as anti-Clec9a antibodies which lack significant agonist activity. These may be referred to as "blocking" antibodies. Monovalent or bivalent antibodies without agonist activity may be particularly suitable as blocking antibodies. Other Clec9a antagonists include nucleic acid molecules or analogues thereof capable of hybridising with DNA or RNA encoding CLEC9a. Such agents include ribozymes, RNAi, siRNA, etc.

Further CLEC9a antagonists are competitors for the CLEC9a ligand, which can block binding sites on the ligand for dendritic cell-associated CLEC9a and so prevent the ligand from being recognised or bound by the dendritic cell. Suitable competitors include soluble molecules comprising the extracellular domain of CLEC9a or a portion thereof sufficient to bind to the CLEC9a ligand. Thus the molecule may comprise an amino acid sequence having at least 70% identity, at least 75% identity, at least 80% identity, at least 85% identity, at least 90% identity, or at least 95% identity to the extracellular domain (CTLD) of human CLEC9a as shown in FIG. 1, or murine CLEC9a as shown in FIG. 2, or a fragment thereof having affinity for the CLEC9a ligand. The fragment may comprise at least 20, 30, 40, 50, 60, 70, 80, 90, 100, 110 or at least 120 amino acids of the respective extracellular domain sequence or a sequence having the required level of identity therewith.

The CLEC9a extracellular domain (or portion thereof) may be associated with a heterologous moiety which may modulate some property of the antagonist, such as its pharmacokinetic properties in vivo. The extracellular domain may be covalently or non-covalently bound to the heterologous moiety, or may be expressed as a fusion protein with the heterologous moiety. For example, the heterologous moiety may be an antibody Fc domain, in order to provide increased serum half life and allow efficient clearance of complexes between the antagonist and the CLEC9a ligand.

Other possible functions of the heterologous moiety include mediating oligomerisation of the CLEC9a extracellular domain, and facilitation purification of the antagonist or isolation from a sample. For example, a suitable antagonist may be a soluble molecule comprising or consisting of the CLEC9a extracellular domain (or a fragment thereof sufficient to bind CLEC9a ligand) associated with an avidin monomer. The avidin monomers will tend to associate into tetramers, providing a complex comprising four CLEC9a domains and four avidin subunits. This construct can readily be isolated by contact with biotin, which may be provided on a solid support such as a bead.

Where the binding agent or antagonist is a protein, it may be possible to administer a nucleic acid (e.g. DNA) encoding the antagonist. Typically the nucleic acid will be taken up by cells within the body (e.g. muscle cells), expressed, and secreted from those cells. This approach is often referred to as DNA vaccination.

Antibodies are particularly suitable as binding agents and antagonists, and can conveniently be expressed in scFv form. If necessary, an antibody can be encoded as a fusion protein with the antigen, or with an effector moiety as described above. An example of a DNA vaccination approach is described in Nchinda et al., J. Clin. Invest. 118(4), 1427-36, 2008.

The nucleic acid typically comprises a coding region encoding the binding agent or antagonist, optionally in conjunction with any desired fusion partner, in operable linkage with transcriptional and translational regulatory sequences to ensure appropriate expression and secretion of the protein from cells which take up the nucleic acid. Such sequences include (but need not be limited to) transcriptional initiation sequences (e.g. promoter and enhancer), transcriptional termination sequences, appropriate splicing signals, translational initiation and termination sequences, and a signal peptide to enable secretion.

Thus the invention further provides a nucleic acid (e.g. a DNA) encoding a CLEC9a antagonist or binding agent, for use in a method of medical treatment. Also provided is a nucleic acid encoding a CLEC9a antagonist or binding agent for use in a method of and therapeutic uses thereof.

CLEC9a Ligand

The present inventors have found that CLEC9a recognises a ligand displayed by certain types of dead and dying mammalian cells. In particular, certain types of cell death appear to trigger display of the ligand. This is a surprising finding because many known members of the C-type lectin family (including Dectin-1, which is the most closely related protein to CLEC9a) are receptors for pathogen-associated molecular patterns, and so recognise structures displayed by pathogens, rather than self molecules.

It is well recognised that certain mechanisms of self cell death are capable of triggering an immune response. These may be regarded as immunogenic cell death. It has been proposed that death by apoptosis (which normally does not result in rupture of the plasma membrane and release of the intracellular contents) is non-immunogenic, while death by other mechanisms such as necrosis (which do involve rupture of the plasma membrane and release of the cell contents) is immunogenic. However, the physiological situation appears to be rather more complex than this. For example, apoptotic cells in vivo are normally absorbed (phagocytosed) by neighbouring cells such as macrophages before the process of cell death is complete. However, if the cells are not phagocytosed, so-called secondary necrosis may occur, in which the plasma membrane may be disrupted and cellular contents released. Cell death of this nature may be immunogenic, despite being apoptotic at least in part.

Immunogenic cell death may play a role in the onset, development or persistence of autoimmune disease. This is reviewed, for example, by Vioritto et al (Clin Immunol 122 (2), 125-134 (2007)), Tesniere et al (Curr Op Immunol 21, 1-8 (2008)) and Kim et al (Immunity 27, 321-333 (2007))

Dendritic cells may play a role in induction of any immune response caused by immunogenic cell death, by taking up cellular debris from the dead or dying cells (or even absorbing the entire cell) and presenting processed fragments to T cells.

The present inventors have now found that CLEC9a is capable of binding to a ligand displayed by dead or dying cells, and that CLEC9a signalling may be triggered by this interaction.

It is also believed that the ligand is not synthesised de novo during the process of cell death. Rather, it may be constitutively expressed by some or all mammalian cells but is not accessible for interaction with CLEC9a while the cell remains healthy. Certain types of cell death result in exposure of the ligand and/or release of the ligand from the cell, in a form capable of interacting with CLEC9a. This may involve disruption of the plasma membrane.

Experimentally, exposure of the ligand can be caused by treatments such as irradiation (e.g. with ionising radiation such as UV light), serum deprivation, at least one freeze/thaw cycle, or by treatment with chemotherapeutic agents such as anthracyclines (such as doxorubicin and daunorubicin) and anthracenedione (such as mitoxantrone). However death by osmotic shock appears not to expose the ligand.

Thus, without wishing to be bound by any particular theory, it is believed that CLEC9a may be involved in generation of the immune response caused by immunogenic cell death. The interaction between CLEC9a and its ligand can be inhibited by CLEC9a antagonists. These include binding agents capable of binding to (the extracellular domain of) CLEC9a. Other examples include competitors for CLEC9a binding sites on the ligand, such as soluble agents comprising the extracellular domain of CLEC9a or a portion thereof (e.g. at least 20 amino acids, at least 50 amino acids, at least 100 amino acids, at least 150 amino acids, or at least 200 amino acids of the extracellular domain) which is capable of binding to CLEC9a ligand.

Antagonists capable of inhibiting binding between CLEC9a and its ligand will be capable of inhibiting CLEC9a signalling when contacted with suitable dead or dying cells (e.g. UV-irradiated mammalian cells) or a lysate, extract or fraction thereof capable of inducing CLEC9a signalling. Any suitable test system may be used to assess this capacity. For example, in dendritic cells expressing CLEC9a, CLEC9a signalling may be assessed by determining phosphorylation of Syk kinase. Alternatively an artificial reporter system may be used comprising the CLEC9a extracellular domain functionally linked to a reporter system such as the CD3zeta chimera described in the examples.

Binding Agents

Any suitable molecule having a sufficiently high affinity and specificity for CLEC9a may be used as a binding agent. The molecule may be a protein, nucleic acid (e.g an aptamer), carbohydrate (e.g. oligo- or polysaccharide), small molecule, etc. Particularly preferred binding agents are physiological ligands for CLEC9, and antibodies against CLEC9a and functional fragments thereof.

The binding agent preferably has a binding affinity (affinity constant) for CLEC9a, particularly for the CLEC9a ECD, of at least $10^5$ M$^{-1}$, at least $10^6$ M$^{-1}$, at least $10^7$ M$^{-1}$, preferably at least $10^8$ M$^{-1}$, more preferably at least $10^9$ M$^{-1}$.

The binding agent preferably has an affinity at least 2×, and preferably at least 5×, at least 10×, at least 50× or at least 100× greater than for any non-CLEC9a molecule, including other C-type lectins.

It is well-known that fragments of a whole antibody can perform the function of binding antigens. Examples of functional binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

As antibodies can be modified in a number of ways, the term "antibody" should therefore be construed as covering any specific binding substance having an binding domain with the required specificity. Thus, this term covers the antibody fragments described above, as well as derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It will be appreciated that the binding agents used in the methods described herein are generally required to bind the extracellular domain of CLEC9a in order to exert the required effect. Reference to a binding agent capable of binding CLEC9a should be construed accordingly, unless the context allows otherwise.

In certain aspects of the invention, it is desirable to cross-link an antigen (e.g. a protein or peptide antigen) to a binding agent as described. The skilled person is well aware of suitable methods and reagents. Where the binding agent is a protein, the antigen may be coupled via a sulphydryl group of the binding agent. The sulphydryl group may normally be free, or it may normally be part of a disulphide bond in which case it may be exposed by selective reduction of the binding agent. For example, an antibody can be mildly reduced selectively in the hinge region using the reducing agent mercaptoethanosulfonate. Then, the antigen is activated using sulpho-SMCC, an hetero-bifunctional cross-linking reagent that reacts with the tertiary amines of the protein, generating groups reactive with free sulphydryls. Then, the antibody and the activated antigen are incubated together resulting in the protein being conjugated to the monovalent antibody[18]. Alternatively, if a suitably immunogenic peptide sequence from the antigen is known, such a peptide containing a cysteine with a free sulphydryl can be synthesized and coupled to sulpho-SMCC activated antibody, which will remain bivalent and with several peptides bound per molecule of antibody.

Pharmaceutical Compositions

The polypeptides, antibodies, peptides, nucleic acids and cells described herein can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

A composition may be administered alone or in combination with other treatments, either simultaneously or sequentially dependent upon the condition to be treated.

Examples

CLEC9a Sequences and Structure

A search of the NCBI gene database shows that CLEC9a sequence has been already identified in Mus musculus, Pan troglodytes, Homo sapiens and Macaca mulatta. A blast search using the protein sequence of mouse CLEC9a, also shows predicted CLEC9a proteins in Rattus norvegicus, Canis familiaris and Bos Laurus. The human cDNA sequence and the annotated protein sequence with relevant domains is detailed in FIG. 1. The mouse cDNA sequence which we have cloned from mouse CD8α+ DCs and its annotated protein sequence is detailed in FIG. 2. This sequence differs from the published cDNA sequence, which contains an additional G residue causing a frameshift towards the end of the molecule, leading to a longer protein than that shown in FIG. 2. Our sequence appears to be correct, since it matches the published genomic sequence (NC_000072.4 GI:94471533); as can be seen in this page the position 13480 of the genomic (A<u>T</u>TT) matches our cDNA sequence. The sequences predict a C-type lectin family protein with a C-type lectin-like domain, (CTLD), a stalk region, a transmembrane region and a cytoplasmic domain containing one-species-conserved tyrosine highlighted in FIGS. 1 and 2. We have found transcripts for three isoforms of mouse CLEC9a that we have termed long isoform (exons 1-7), short isoform that lacks exon 4, including a putative cysteine involved in dimerization, and very short isoform, that couples exon 3 to exon 7, yielding a mRNA coding for a transmembrane protein that, if expressed, would share the transmembrane-intracellular domains with CLEC9a but would have a short and different extracellular domain. We only have evidence of protein expression for the long isoform.

Figure 3:
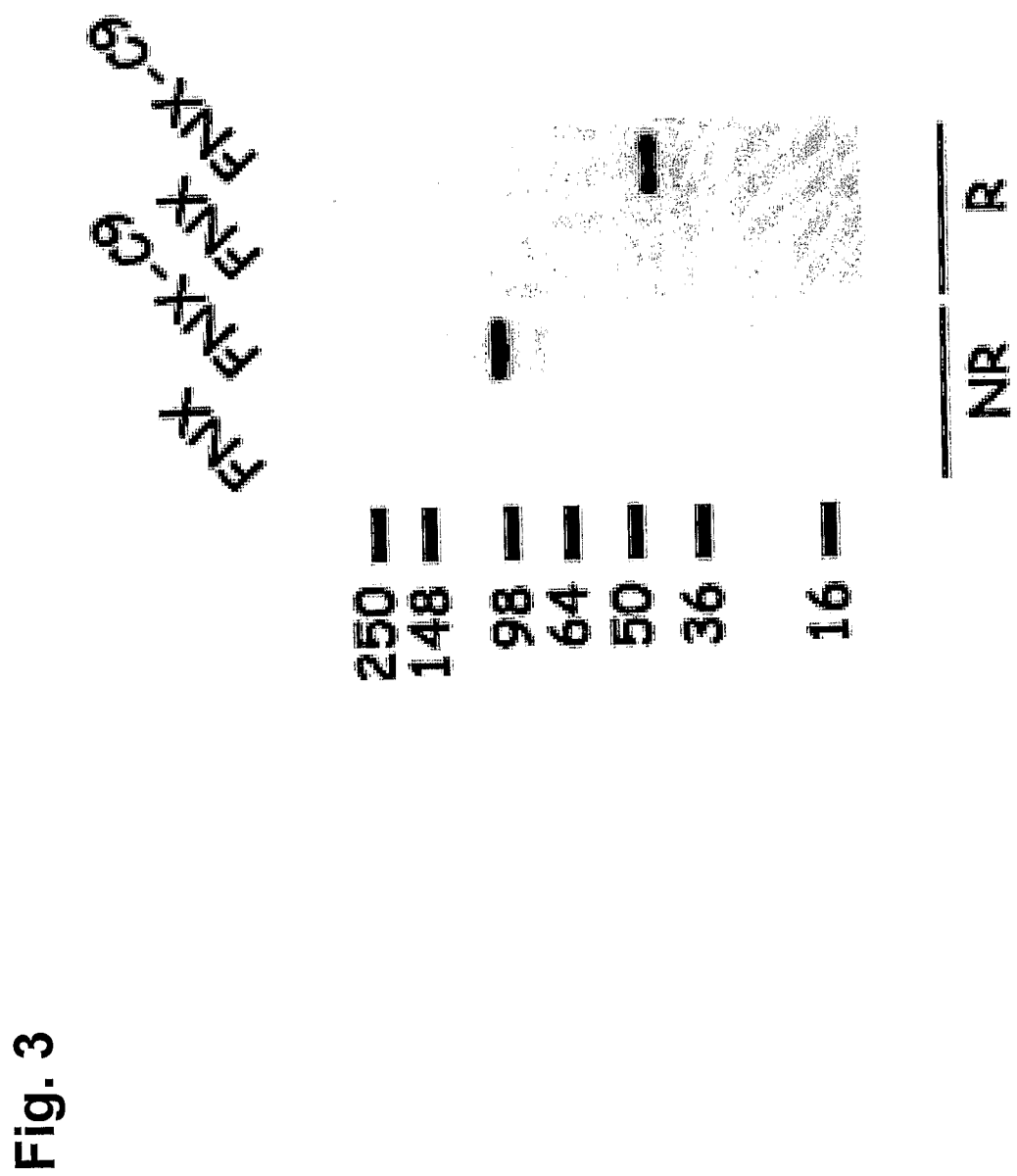
FIG. 3 shows detection of mouse CLEC9a protein expressed in human Phoenix cells. Western blot using anti-CLEC9a on full lysates from Phoenix cells expressing CLEC9a (FNX-C9) or parental cells (FNX) in reducing (R) and non-reducing (NR) conditions.

The structure of mouse CLEC9a was analyzed. The core protein has a predicted molecular weight (Mw) of about 29.67 KDa However, when expressed in the HEK-293 cell line the Mw is about 100 KDa in non-reducing conditions, and a Mw of about 45 KDa in reducing conditions (FIG. 3). These results indicate that the molecule forms dimers through the cysteine in the stalk, like other lectins in the family, and the monomer is strongly glycosylated.

CLEC9a Expression

CLEC9a was first detected in our laboratory as a result of a representational difference analysis between samples of mouse spleen CD11c+CD8+ and CD11c+CD8− cells. The results showed that sequences corresponding to the EST clone AW318446, corresponding to CLEC9a, were selectively found in the CD11c+CD8+ transcripts.

Figure 4:
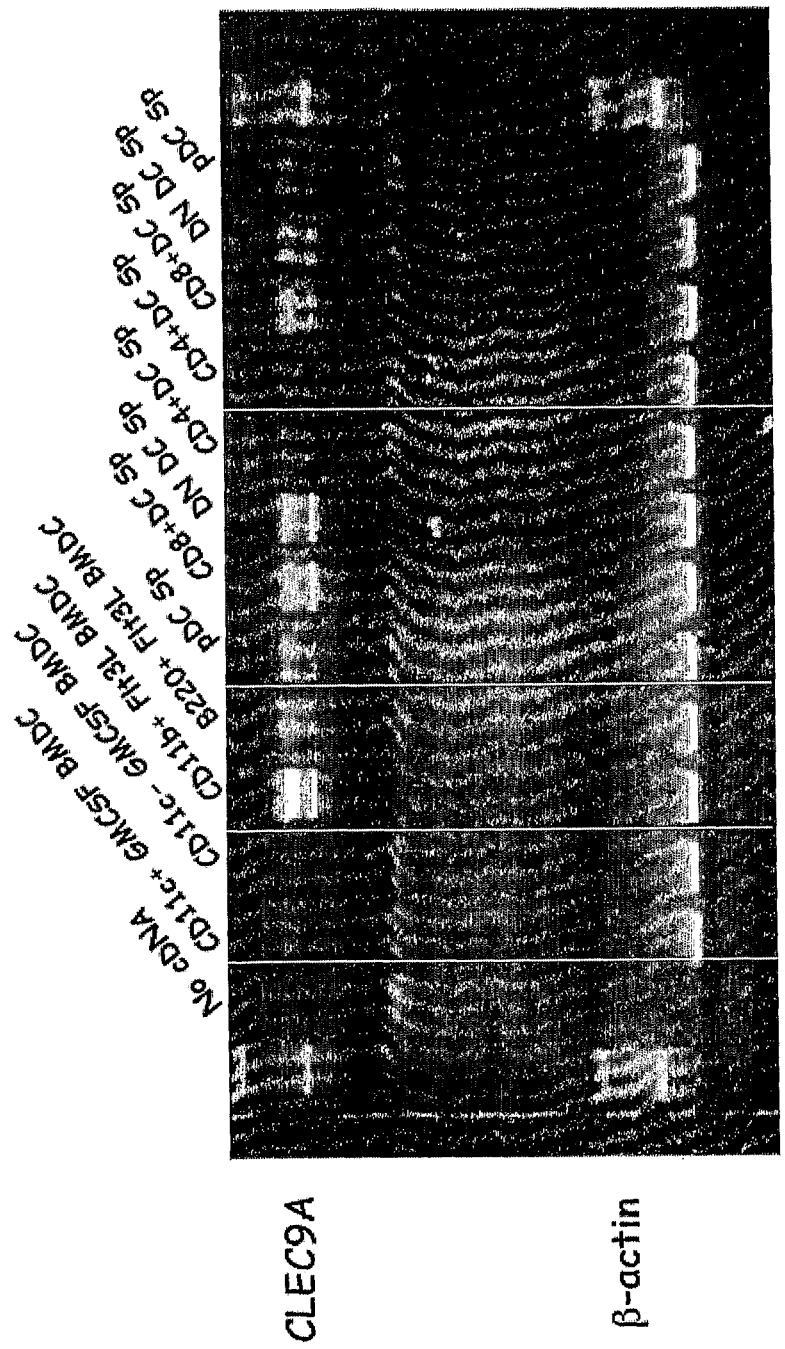
FIG. 4 shows distribution of mouse CLEC9a transcripts in spleen DC and in vitro cultured BMDC. mRNA from subsets of spleen DC or from purified subsets of GMCSF or Flt3L-BMDC were subjected to RT-PCR using CLEC9a specific primers (upper lanes) or β-actin primers (lower lanes) as indicated under Methods.

The analysis of the transcripts in sorted subsets of splenic DCs revealed high expression of CLEC9a in the CD8+ subset, although double negative (CD4−CD8−) and B220+ spleen DC also showed some transcripts for CLEC9a (FIG. 4). No significant expression was found in GMCSF-derived BMDC (FIG. 4). Mouse bone marrow cultured for 10 days in the presence of Flt3L (50 ng/ml) generates CD11c+ cells that are either CD11b+, functionally corresponding to spleen conventional DC and including a CD8-like subset[19], or B220+, which are functional equivalents of plasmacytoid DC (pDC). High expression of CLEC9a was found in the sorted CD11b+ subset, although the pDC subset showed some expression of the molecule (FIG. 4).

Figure 6:
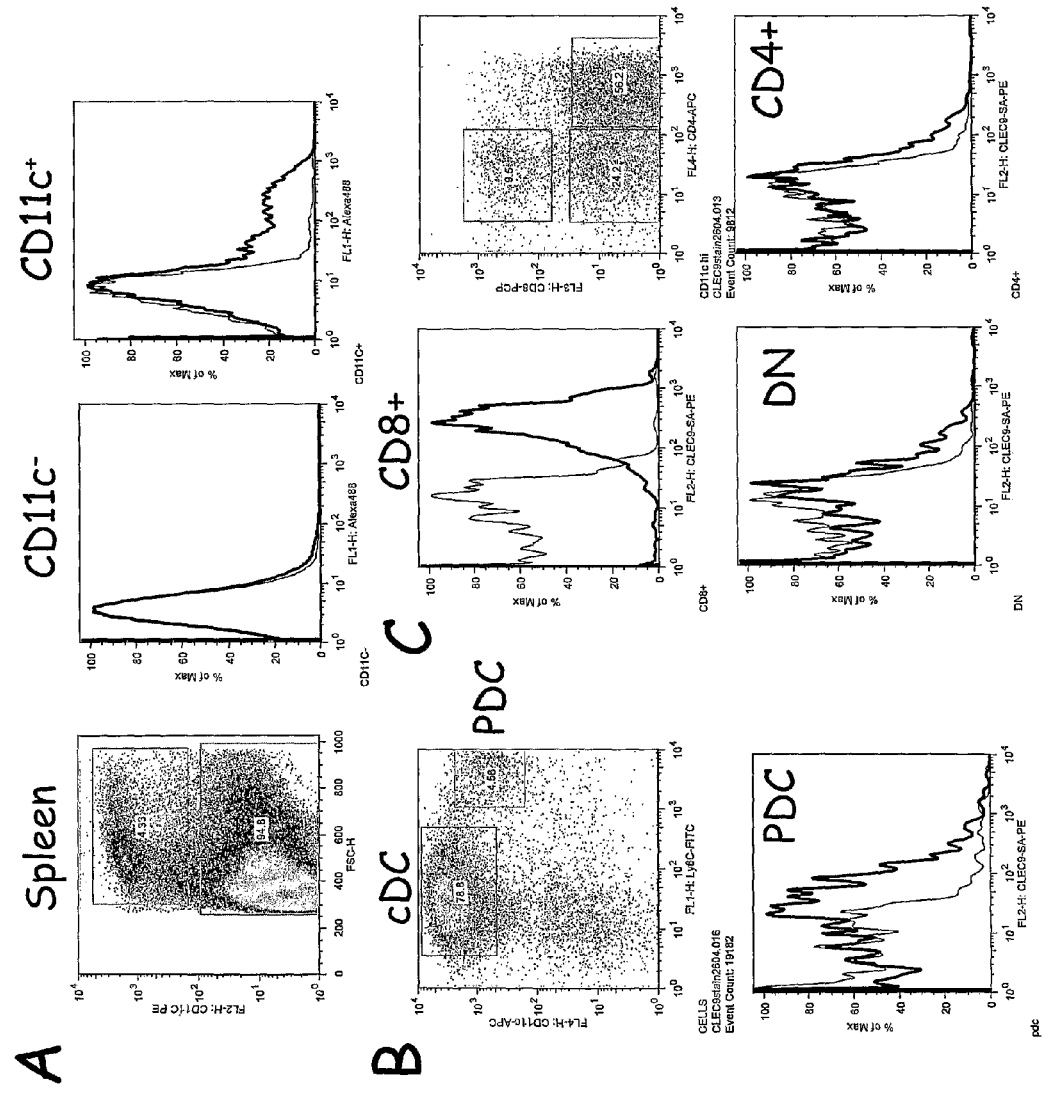
FIG. 6 shows expression of CLEC9a in primary cells. Splenocytes were stained with biotin anti-CLEC9a (thick line, 10 mg/ml) or biotin-rat IgG1 (thin line, isotype control) followed by streptavidin-PE (1:1000) and counterstained with CD11c, CD4, CD8 or Ly6C. Histograms show the staining for CD11c negative cells vs CD11c positive cells, which are then further analyzed in the CD4/CD8 subsets of conventional DCs or in the Ly6C+ subset corresponding to pDC.

Since the RT-PCR is a sensitive technique that can detect very low level of transcript, it is limited by the quality of purification of the sample. To unequivocally determine the pattern of expression of CLEC9a, we generated rat monoclonal antibodies (mAb) against mouse CLEC9a, using a CD3ζ-NKRP1-CLEC9a chimera expressed in B3Z cells with a β-Gal reporter (FIG. 5) as indicated under Methods. We selected three mAbs named 1F6, 397, and 7H11. Using these mAb, we have studied the pattern of expression of the molecule in mouse spleen and bone marrow. CLEC9a was highly expressed in CD8α+ conventional DCs (MFI~350-400) and showed moderate expression (MFI~65-70) in pDCs (FIG. 6). The molecule was not detected in other cell types explored including B cells, T cells, NK cells, NKT cells, monocytes, macrophages and granulocytes.

As a model for analysis of CLEC9a function in vitro, we analyzed expression in mouse GMCSF- and Flt3L-derived BMDC. We did not detect expression of the molecule in GMCSF-derived BMDC, whereas CLEC9a was selectively expressed in the CD11b$^{lo}$, CD24$^{hi}$, B220-subset of Flt3L BMDC, functionally homologous to CD8+ splenic DC[19], and also in a subset of the CD11b$^{lo}$ B220+, equivalent to pDC (Data not shown).

CLEC9a Signals Through Syk Kinase and Promotes DC Activation.

Figure 7:
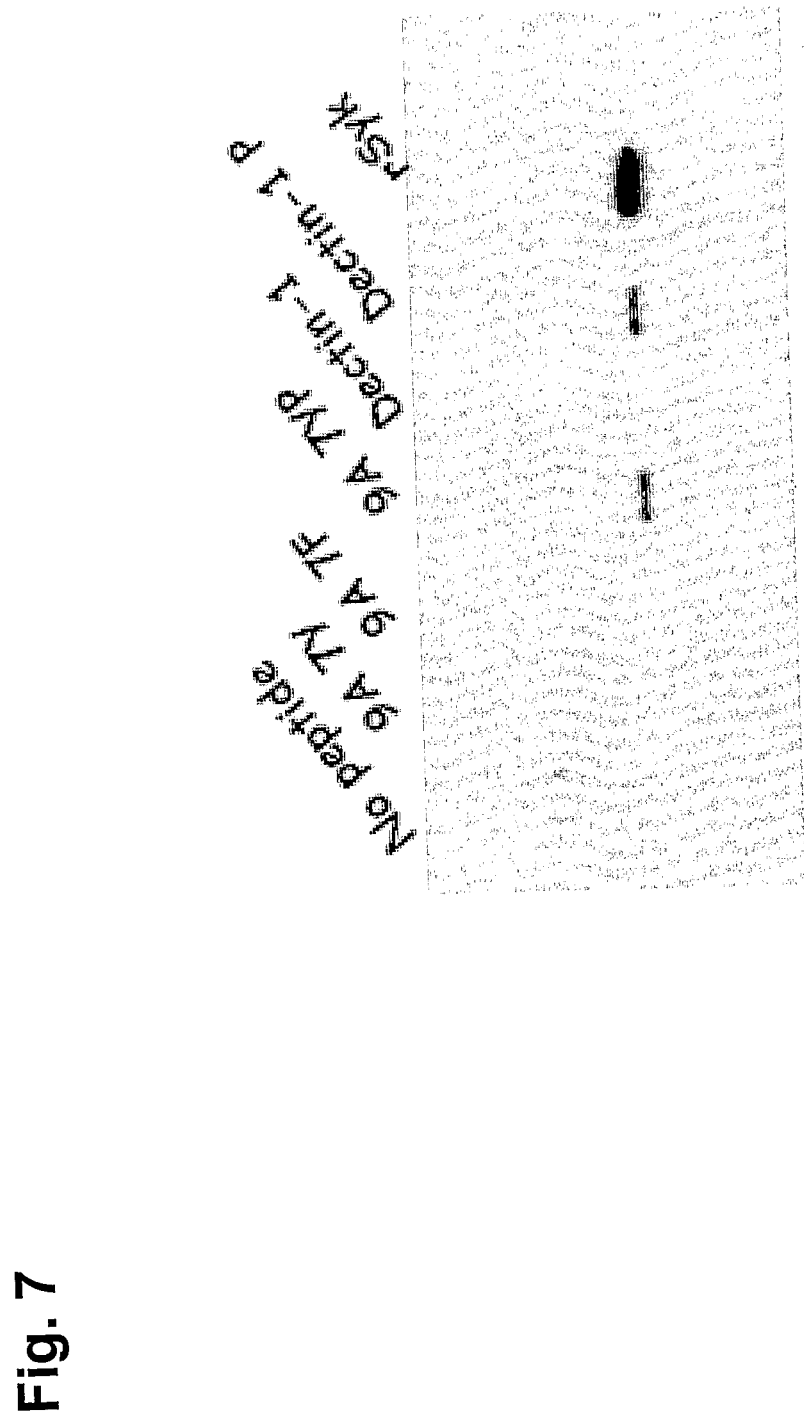
FIG. 7 is a Western blot showing Syk pull-down with CLEC9a cytoplasmic peptide. A biotinylated peptide corresponding to CLEC9a cytoplasmic domain or a Dectin-1 control was used to pull down recombinant Syk as indicated in Methods.

Sequence analysis reveals Tyr7 from mouse that is conserved in all the species with the same structure EXXYXXL, which could serve as a putative SH2 binding domain and/or a tyrosine-based sorting signal. This sequence allows/mediates Syk binding in mouse Dectin-1 and is termed "HemITAM"[22]. However, this putative sequence is necessary but not sufficient for predicting Syk binding. In consequence, we designed biotinylated peptides with the cytoplasmic tail of mouse CLEC9a expressing the phosphorylated Tyr7, or with that Tyr7 without phosphorylation or even mutated to Phe. The Tyr7 phosphorylated peptide was able to pull down recombinant Syk (FIG. 7) to a similar extent than the cytoplasmic tail from mouse Dectin-1 expressing both Tyr phosphorylated as a positive control[23].

Figure 8:
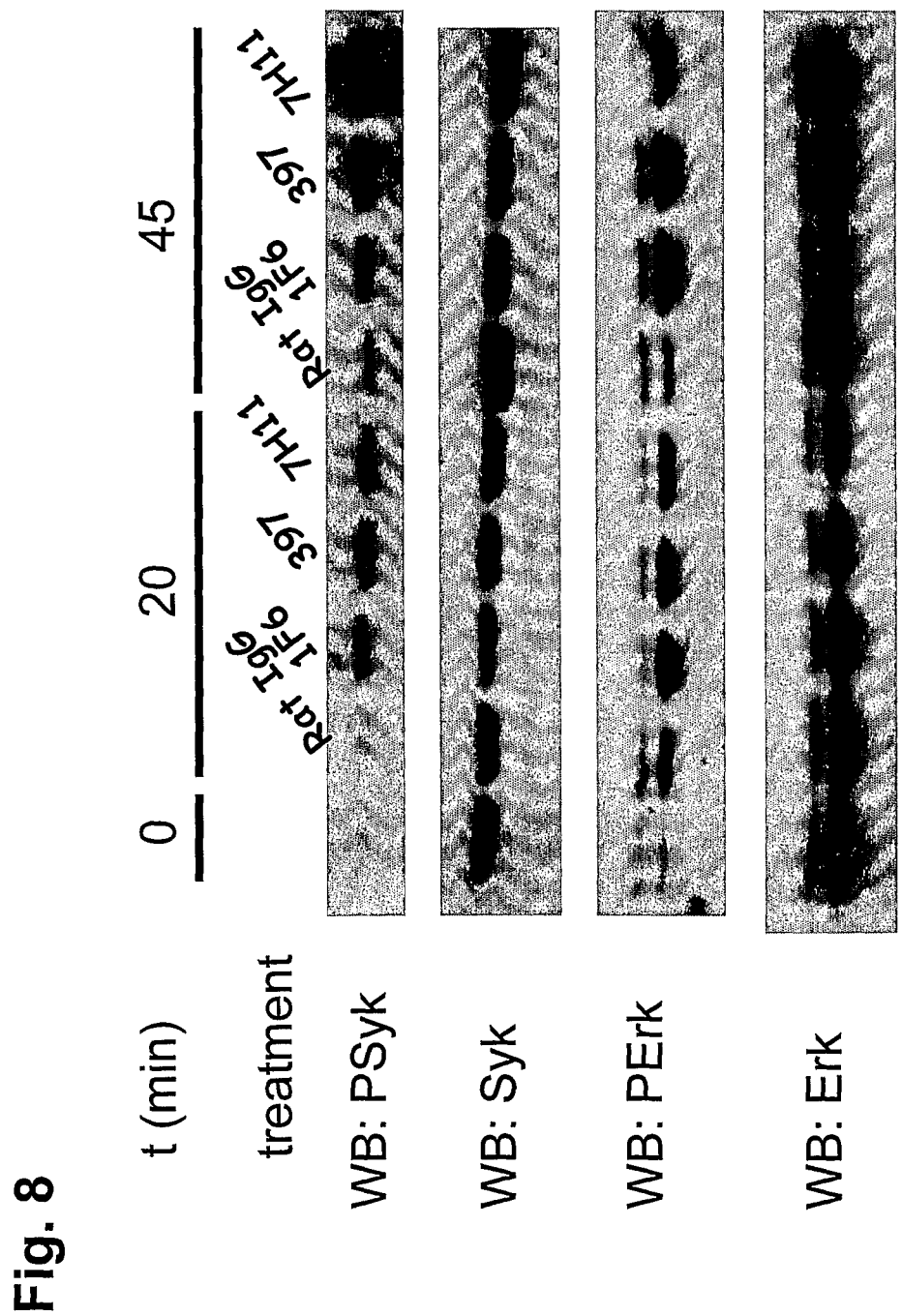
FIG. 8 shows kinase activation with anti-CLEC9a. LK cells expressing CLEC9a were activated for the indicated times with plated antibodies and then were lysed and subjected to SDS-PAGE and WB with anti-P-Syk or anti-P-Erk antibodies to detect activation of these pathways. Protein controls with anti-Syk or anti-Erk indicate the total kinase.

To determine if CLEC9a truly acts as a signalling receptor, we used the rat anti-mouse CLEC9a mAb above described. We generated transfectants expressing CLEC9a in LK cells, a mouse B cell line negative for CLEC9a expression but containing endogenous levels of Syk[23]. The triggering of CLEC9a with all three plated anti-CLEC9a antibodies tested resulted in phosphorylation of Syk and Erk in LK cells (FIG. 8).

To determine whether Syk is necessary for CLEC9a signalling, we used stable transfectants of the reporter T cell line B3Z, which does not express Syk. The contribution of the Tyr7 to CLEC9a signalling was analyzed using a mutant version of CLEC9a with the Tyr7 mutated to Phe (CLEC9a Y7F). We transduced B3Z cells with CLEC9a wt or Y7F and co-transduced or not with Syk kinase. Plated anti-CLEC9a mAbs induced NFAT activation in B3Z-C9 wt-Syk through the wt cytoplasmic tail of C9, but not in the absence of either Syk or the Y7 (not shown).

Regulation of Immuno-Regulatory Cytokines/Co-Stimulatory Molecules Through CLEC9a.

Figure 9:
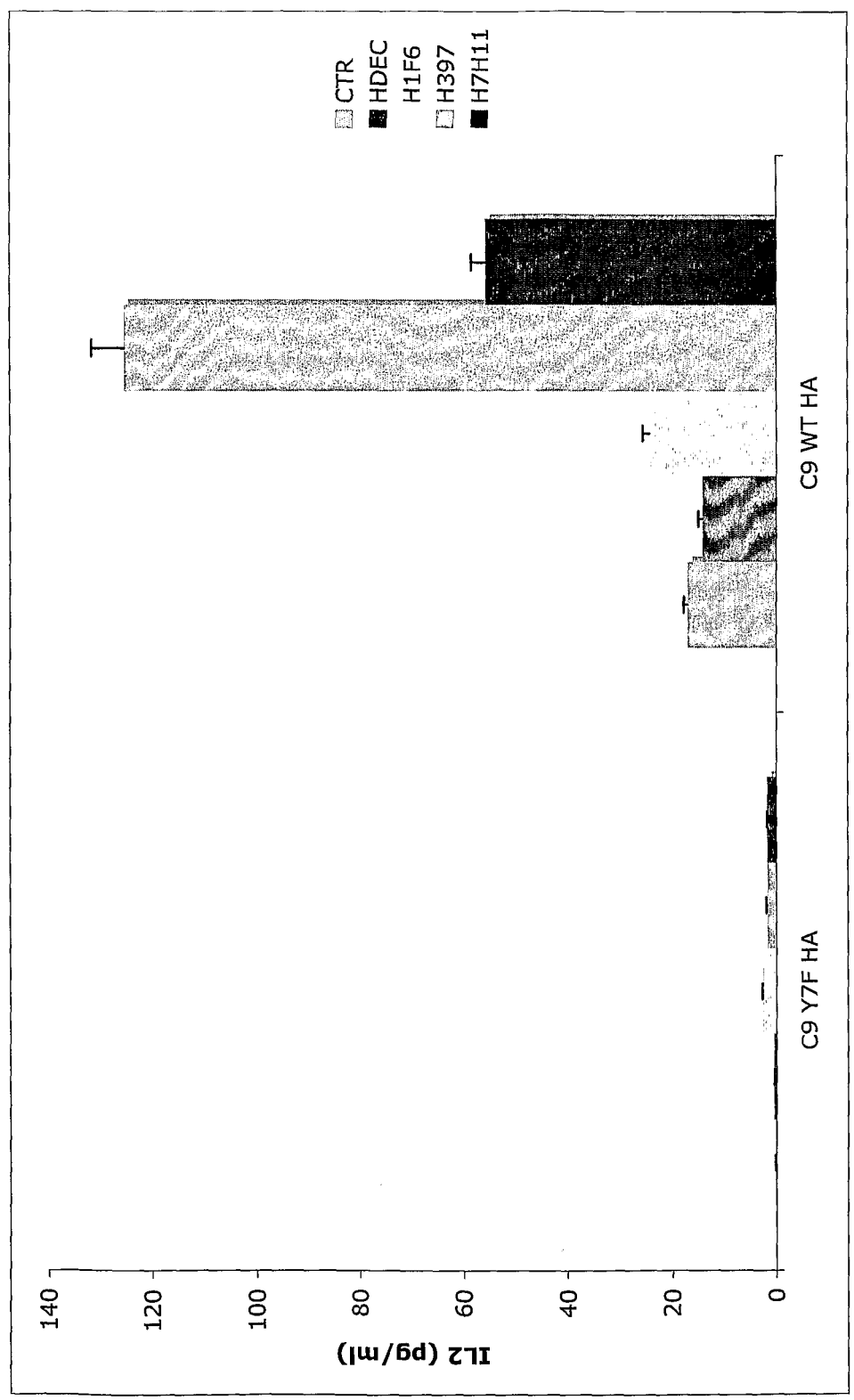
FIG. 9 shows the induction of cytokines by anti-CLEC9a hybridomas. LK cells expressing CLEC9a ($10^5$ cells/well) were cultured with the indicated hybridomas before collecting the supernatants and test for IL-2.

To determine whether signalling through CLEC9a can contribute to the production of regulatory cytokines or expression of co-stimulatory molecules in the cells where is expressed, we have analyzed LK transfectants with wt CLEC9 or the Y7F mutant. Hybridoma cells expressing 397 anti-CLEC9a and, to a lesser extent, 7H11 triggered specific IL-2 production through the CLEC9a molecule that was abolished in the Y7F mutant (FIG. 9). DEC-205 control hybridoma did not trigger any response and 1F6 anti-CLEC9a triggered a reduced response that opens the possibility that these antibodies can behave differentially for cytokine production, which would be very attractive from the prospective of CLEC9a targeting (agonist antibody, 397, versus blocking antibody, 1F6).

Figure 10:
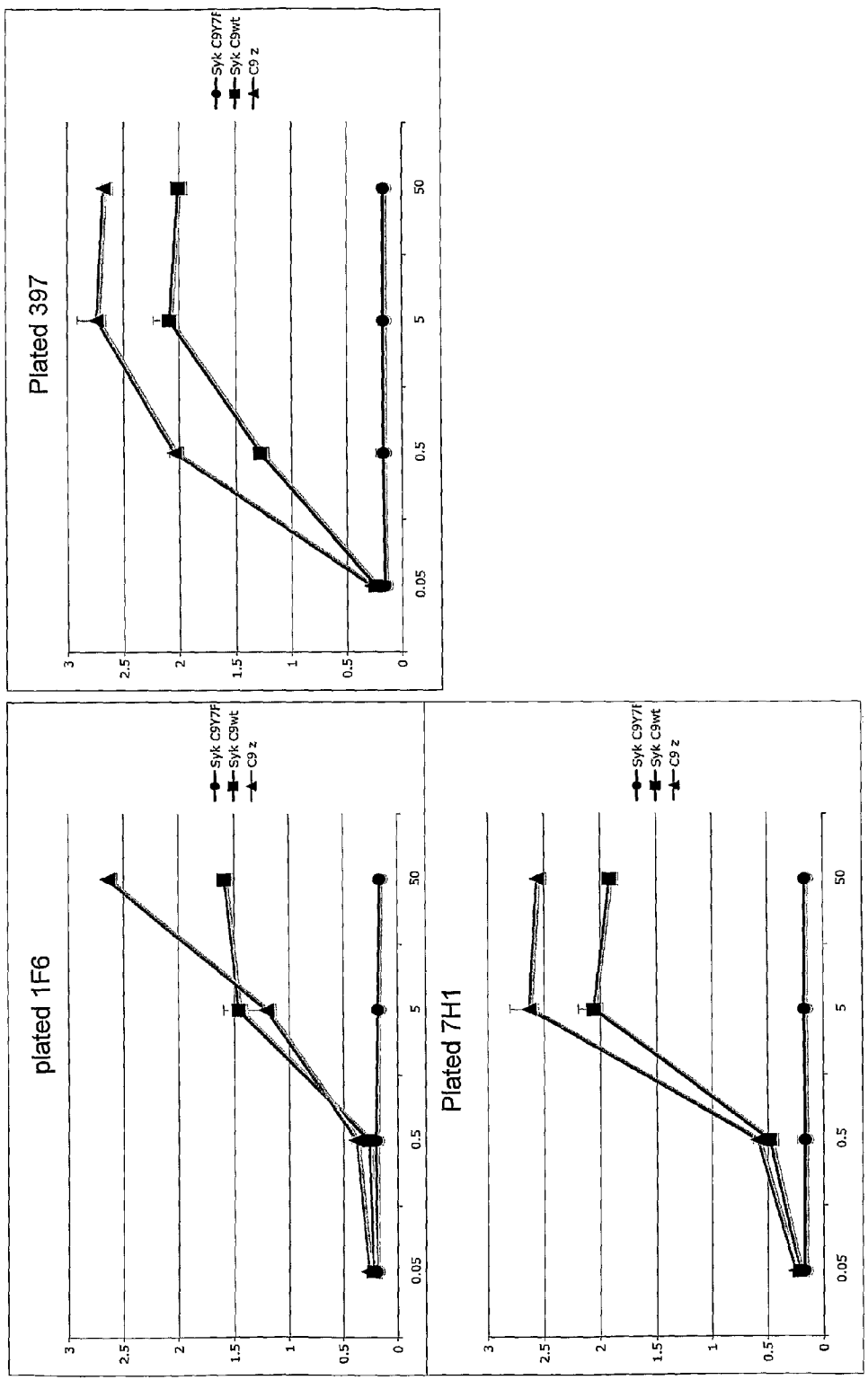
FIG. 10 shows that plated anti-CLEC9a induces NFAT activity through the WT tail of CLEC9a in the presence of Syk and dependent on the presence of Y7. B3Z expressing CLEC9a-CD3ζ (σ), or B3Z-Syk expressing CLEC9a-WT (v) or CLEC9a-Y7F (λ). NFAT activity is measured as indicated under Methods. The X axis shows the concentration of anti-CLEC9a antibodies (μg/ml) used to coat the plates.

To determine the requirements for CLEC9a WT tail activation we analyzed stable transfectants of the reporter T cell line B3Z, which does not express Syk. The contribution of the Tyr7 to CLEC9a signalling was analyzed using a mutant version of CLEC9a with the Tyr7 mutated to Phe (CLEC9a Y7F). We transduced B3Z cells with CLEC9a wt or Y7F and co-transduced or not with Syk kinase. Plated anti-CLEC9a mAbs induced NFAT activation in B3Z-C9 wt-Syk through the wt cytoplasmic tail of C9, but not in the absence of either Syk or when the Y7F mutant was used (FIG. 10).

Figure 11:
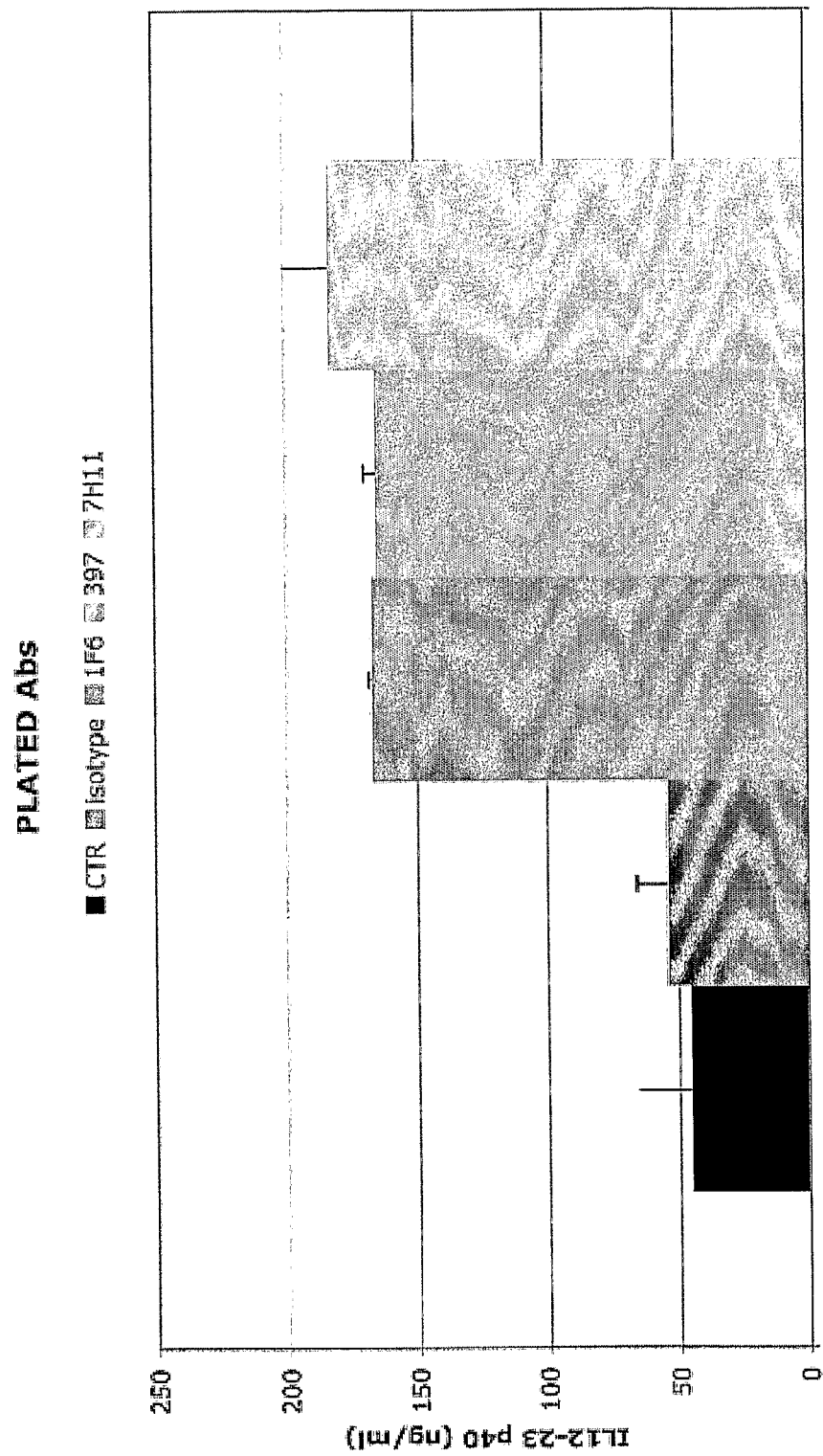
FIG. 11 shows that anti-Clec9a antibodies immobilised on plastic induce production of IL12-23 p40 protein in Flt3L BMDC. Flt3L BMDC were incubated on plates coated with anti-CLEC9a mAb and supernatants after overnight culture were analyzed for IL12-23 p40.

Flt3L BMDC respond to plated anti-CLEC9a mAbs by production of IL12-23 p40 protein (FIG. 11).

These results demonstrate that CLEC9a is a signalling molecule capable of activating DCs.

CLEC9a is an Endocytic Receptor that Selectively Targets CD11c+CD8+DC In Vivo

The potential of anti-CLEC9a mAb to be internalised by endogenous CLEC9a expressed in Flt3L BMDC was analyzed by FACS and revealed that CLEC9a is an endocytic molecule. Confocal analyses showed targeting of the antibody to intracellular compartments (data not shown). These results suggest that CLEC9a is an endocytic receptor that can be targeted by antibodies coupled to antigens (tumor/viral vaccination) to specifically deliver the cargo to cell subsets selectively expressing the molecule. To determine whether CLEC9a mAb serve as a targeting tool in vivo, we injected i.v. 7H11-Alexa-488 or isotype control. After 16 h, we analyzed total splenocytes and the antibody selectively targeted cD8α+ DC (MFI~350-400), and, with lower affinity, PDC (MFI~65-70). Labelling of splenocytes with anti-rat Cy5 suggested that most of the rat anti-mouse CLEC9a mAb was endocytosed, since it did not co-stained with the anti-rat secondary reagent (not shown).

To explore whether the targeting through CLEC9a leads to the processing and presentation of antigen by a specific subset in vivo, we coupled a biotinylated derivative of an immunodominant peptide for the CTL response to OVA protein (SIINFEKLC-biot (SEQ ID NO: 6), named S1) to isotype control or anti-CLEC9a mAb as indicated under Methods. The biotinylation of the peptide allowed us to determine that there was between 1-1.2 peptides per antibody in all cases. Mice were injected i.v. either with 5 μg of the S1-coupled anti-CLEC9a or with the S1-isotype control. The following day, splenocytes were enriched in CD11c+ or CD11c− subsets and tested for their ability to induce OT-I T cell proliferation and cytokine production (FIGS. 12a and b). Only the anti-CLEC9a targeted CD11c+ cells resulted in proliferation and IFN-γ production by OT-I cells, showing that CLEC9a targets specifically CD11c+ DC resulting in presentation to antigen-specific T cells.

To further determine which subset of dendritic cells is targeted by anti-C9, mice injected with S1-coupled anti-C9 were sorted in the three major subsets of conventional DCs and tested with OT-I T cells as above. Only the CD8+ subset of DCs mediated proliferation and IFN-γ production by T cells, confirming that CLEC9 targets specifically the CD11c+ CD8+ DC resulting in priming of antigen-specific T cells (FIGS. 12c and d).

Targeting In Vivo Using Anti-CLEC9a mAb Plus Anti-CD40 Results in Priming of CTLs and Tumor Rejection We explored whether CLEC9a targeting in vivo could induce specific T cell activation. Injection of 2 µg of anti-C9-S1, but not the isotype control, results in the induction of specific CTL activity from the endogenous repertoire in vivo when co-administered with anti-CD40 (FIG. 13). This behaviour is similar to that observed with anti-DEC205-S1, previously described[24] as evidenced by in vivo killing assays (FIG. 13A).

Mice given S1 coupled to control mAb did not eliminate target cells irrespective of anti-CD40 co-administration. In contrast, target cells were completely eliminated from mice given S1 coupled to anti-CLEC9a together with anti-CD40. No response was seen when the anti-CD40 mAb was omitted. Consistent with target cell elimination, significant numbers of tetramer positive OVA/H-2 Kb-specific CD8+ T cells were found only in the spleens and blood of mice that had received anti-CLEC9a-S1 together with anti-CD40. Re-stimulation of the same cells with SIINFEKL (SEQ ID NO: 7) peptide in vitro resulted in secondary expansion, with IFN-γ production and specific killing activity. Identical results were obtained using anti-CLEC9a conjugated to a longer peptide of OVA containing the SIINFEKL epitope ((SEQ ID NO: 7); "S2"; SIINFEKLTEWTSSNVMEERC (SEQ ID NO: 8); FIG. 13E).

Notably, free S1 peptide was unable to induce in vivo killing responses or elicit a significant number of tetramer positive cells even when given at 100 times excess over the amount present in anti-CLEC9a-S1 conjugates (not shown). We conclude that targeting of exogenous antigen to CLEC-9a together with an appropriate adjuvant allows efficient crosspriming of CD8+ T cells.

To determine whether CLEC9a priming of CTL activity can result in tumor therapy, we used the model of B16 melanoma lung metastasis. We inoculated i.v. $2\times10^5$ B16-OVA-GFP melanoma cells and 6 days later different antibodies conjugated to S1 SIINFEKL (SEQ ID NO: 7) derivative (10 µg) together with anti-CD40 (25 µg) were injected s.c. in the paw (FIG. 14). After 18 days following injection of the tumor, the number of lung tumors was analyzed. The results revealed that anti-CLEC9a plus anti-CD40 is effective for tumor therapy (p<0.001, one way ANOVA) (FIG. 14).

We extended the experiments to determine whether anti-CLEC9a targeting can also be used to induce immune responses to endogenous melanocyte differentiation proteins that can serve as B16 tumor-associated antigens (25-27). We synthesised biotinylated peptides encompassing H-2Kb and H-2Db-restricted antigenic epitopes from gp100, TRP-1 and TRP-2 (25-27), coupled these covalently to anti-CLEC-9a and immunized mice with the antibody conjugates together with poly I:C and anti-CD40 as adjuvants. As shown in FIG. 16, a single dose of vaccine given therapeutically three days post transfer of B16 melanoma cells induced nearly complete eradication of lung pseudo-metastases. This was accompanied by the induction of potent IFN-γ responses against the melanoma antigens (FIG. 16). In contrast, the same antigens in untargeted form (conjugated to a control isotype-matched mAb) failed to induce protection or IFN-γ responses (FIG. 16A, B). Similar results were obtained in a prophylactic model in which the vaccine was given prior to B16 challenge (FIG. 16C). We conclude that priming of specific CTL via CLEC-9a targeting can be used for prophylactic or therapeutic vaccination against mouse tumors.

Human Clec9a Expression is Restricted to a Small Subset of Blood DC

To extend these findings to humans, we cloned hClec9a and generated mouse mAbs against it (see Materials and Methods). One of these mAbs was selected to analyze the pattern of Clec9a expression among human peripheral blood mononuclear cells. Human Clec9a expression was absent from lymphocytes, monocytes, NK cells and lineage-negative HLADR-cells (FIG. 15A). It was also not detected in monocyte-derived DC generated by culture in GM-CSF and IL-4 (data not shown). However, Clec9a expression was apparent in a discrete subpopulation of blood DC, defined as lineage-negative HLA-DR+ cells (FIG. 15A).

Five distinct subsets of blood DC have been reported, including a population of CD123+ pDC and different subsets of putatively myeloid CD123– DC distinguishable on the basis of expression of CD16, CD1b/c, BDCA-3, and CD34 (22). The Clec9a+ subpopulation of DC was negative for CD123, suggesting that human pDC do not express Clec9a, unlike pDC in the mouse (FIG. 15B). Clec9a+ blood DC were also negative for CD34, CD16 and CD1b/c. However, Clec9a+ DC were uniformly positive for BDCA-3 (FIG. 15B). Human Clec9a therefore selectively marks a distinct population of BDCA-3+ DC.

Finally, we assessed whether human CLEC-9a, like its mouse orthologue/can function as an endocytic receptor in DC. BDCA-3+DC were stained at 4° C. with Alexa 488-labelled anti-CLEC-9a. After 1 h at 37° C. but not at 4° C., fluorescence was found in intracellular compartments (not shown). Therefore, human CLEC-9a mediates endocytosis of bound antibody in BDCA3+ DC, thereby suggesting that it could be used for antigen targeting to these cells in humans.

Dying/Dead Cells Express a Ligand for CLEC9A.

BWZ cells containing the CLEC9A-CD3ζ chimera have a short generation time and can easily overgrow, generating a significant proportion of dead cells in the culture. We observed a basal activation in the BWZ transfectants expressing CLEC9A without any further stimulation, correlating with the number of dead cells in the BWZ culture (FIG. 17a).

To confirm these results we used a cell line that does not induce a response when added to the BWZ-CLEC9Aζ transfectants. LK cells do not induce a response when exposed to the reporter cells. However, when LK cells were UV-irradiated to induce cell death, they turned into potent inducers of the reporter (FIG. 17b), suggesting that altered cells following UV treatment express ligand/s for CLEC9A. Since bivalent antibodies trigger cross-linking of the molecule expressed in the B3Z cell line and reporter activation, blocking antibodies cannot be tested in this system to demonstrate the specificity of the interaction. However, monovalent Fab fragments of anti-CLEC9A antibodies did not trigger the reporter activity and blocked induction by UV-treated cells in a species-specific fashion (FIG. 17b), demonstrating that the antibody acts blocking specifically the CLEC9A receptor to avoid interaction with the ligand.

This result was confirmed in other independent UV-irradiated cell types (murine 3T3, LK cells, MEFs, EL-4), rat RBL cells, and human HEK-293. When cells are pre-incubated with caffeine (which prevents UV-induced DNA damage and apoptosis) and then exposed to UV radiation, exposure of the ligand is not induced.

We exposed LK cells to different doses of UV and we found that expression of ligand in LK cells correlates with the number of dead LK cells (FIG. 17c), showing that the ligand is selectively expressed in this population.

To confirm this in an independent fashion, we generated recombinant soluble extracellular domain (rsCTLD) for mouse CLEC9A, and mouse Dectin-1 as a control, each coupled to a BirA sequence for monobiotinylation. Monobiotinylated rsCTLD was used to generate PE-tetramers. We stained cells treated with UV 24 h earlier and we detected specific binding of CLEC9A rsCTLD tetramers to TO-PRO 3 positive cells (FIG. 17d, dot plots). As a control, Dectin-1 rsCTLD tetramers did not bind dead cells, yet they bound to their specific ligand zymosan (FIG. 17d, histogram).

As UV treatment induces DNA damage and a series of related stress markers, we tested whether the induction of ligands was caused by DNA damage or mostly by processes involved in cell death. Not only DNA damage-causing reagents, but also serum deprivation or even freeze-thaw, which has been shown to promote primary necrosis resulting in immunogenic cell death, led to exposure of the ligand (FIG. 17e). However, osmotic shock, which induces instant cell death that has been shown to behave as tolerogenic, did not expose CLEC9A ligand (FIGS. 17e and f). In conclusion, CLEC9A ligand is exposed in cells following certain types of primary and secondary necrosis. Moreover, we have found that fixation (or fixation and permeabilization) of the cells instantly promotes changes that make cells permeable to TO-PRO3 and "expose" the ligands for CLEC9A (FIG. 20) further demonstrating that synthesis of the ligand is not induced as a result of damage response to UV, but is exposed as a result of the process of dying in response to certain stimuli.

CLEC9A Mediates an Adjuvant Signal Delivered by Dying Cells to Dendritic Cells.

UV-dead cells signal through the cytoplasmic domain of CLEC9A in a Syk and Y7-dependent fashion (FIG. 21). This system allowed us to explore whether anti-CLEC9A antibodies could act as specific blocking reagents for this interaction and we found that both Fab and full antibodies in soluble form were powerful blocking reagents (FIG. 22). To test the effects of dying cells in dendritic cells and their effector function in vitro, we designed a cross-presentation assay in which UV-treated bm-1 cells loaded with OVA protein were allowed to interact with Flt3L BMDC in the presence or absence of blocking anti-CLEC9A. Bm-1 cells are from a B6 haplotype but express a mutated H2Kb that does not bind the immunodominant class I peptide for OVA (SIINFEKL; SEQ ID NO: 7). As a readout for DC capacity for cross-priming, specific OT-I cells were added to the assay. Proliferation of OT-I cells, as readout for the amount of antigen that was cross-presented, was not greatly affected (FIG. 18a). However, cytokine production by OT-I cells, which is dependent in the help promoted by DC activated by an adjuvant effect, was severely inhibited when blocking CLEC9A antibodies were used (FIGS. 18a and b).

To confirm these results we generated mice deficient in CLEC9A, expressing EGFP under the control of Clec9a promoter (Clec9a$^{egfp/-}$). We generated Flt3L BMDC deficient or not in CLEC9A and we analyzed whether the uptake of dying cells was affected. FIG. 18c shows no difference between in the capacity for uptake of dying cells between CLEC9A+ and CLEC9A− Flt3L BMDC. Then, we assayed the effect of CLEC9A deficiency in Flt3L BMDC in cross-presentation to OVA protein either loaded in UV-treated bm-1 cells or expressed intracellularly in a non-secreted OVA-GFP fusion protein in bm-1 MEFs that were UV treated (FIG. 18d). OT-I proliferation was affected, suggesting a more profound effect in blockade of cross-presentation than the antibody blockade. However, at higher doses of OVA, including OVA expressed by bm1MEFs, proliferation was not affected and IFNγ production was severely inhibited (FIGS. 18d and e). These results suggest that there is a blockade in the adjuvant effect associated to dying cells during cross-priming in vitro in the absence of CLEC9A in DCs.

CLEC9A Senses Immunogenic Cell Death to Promote Crosspriming In Vivo

As CD8α+ DC expressing CLEC9A are the main cell type characterized to promote cross-priming to dead cell associated antigen in vivo, we tested the effect of CLEC9A blockade in this function. Mice that received UV-treated bm1 MEFs expressing OVA showed expanded CD8+ T cells against OVA from the endogenous repertoire 6 days later (FIG. 19a, left panel). These CD8+ T cells were able to produce IFN-γ in response to SIINFEKL, showing that they are effector cells and that dead cells behaved as an immunogenic carrier of antigen associated to adjuvant activity of dead cells (FIG. 19a, right panel). Pre-treatment with anti-CLEC9A blocking antibody, but not with isotype control, blocked both the generation of specific CD8 response and its effector activity (FIG. 19a).

To determine the precise role of CLEC9A in the process of immunogenicity of dead cells related to crosspriming to dead cell-associated antigen, we exploited the assay in CLEC9a$^{egfp/-}$ mice. The results showed a very significant and partial inhibition of crosspriming to dead cell associated antigen in vivo in the absence of CLEC9A (FIG. 19b, left panel). As knock-out mice were generated in a mixed C57BL/6-129 background and are being back-crossed with C57BL/6 (N3), we grouped the 12 female litters whose individuals were pooled in FIG. 19b, left panel, and we compared the average between CLEC9A+ and CLEC9A− mice, showing that 12 out of 12 litters showed reduction, with an average 30.05% inhibition (p<0.0001, Student's t test) (FIG. 19b, right panel). As shown in FIG. 19b, right panel, differences in background penetrance among different litters could explain significant variability in cross-priming ability among litters and dampen the real difference between CLEC9A+ and CLEC9A− mice, which is still very significant albeit only partial. Moreover, IFN-γ production in response to SIINFEKL (SEQ ID NO: 7) ex vivo was severely affected, showing the deficiency in effector response generated via cross-priming to dead-cell associated antigen in the absence of CLEC9A (FIG. 19c). In conclusion, CLEC9A deficiency results in a reduced adjuvancy of the dead-cells with associated antigen that leads to a blockade in specific T cell effector response to dead cell associated antigen.

Methods

Mice

C57BL/6 mice, OT-I mice on a Rag−/− C57BL/6 background and B6.SJL background mice (congenic CD45.1+) were bred at Cancer Research UK in specific pathogen-free conditions. K$^{bm-1}$ mice were purchased from The Jackson laboratory (Bar Harbor, Me.; stock number 001060), and, together with C57BL/6 mice, OT-I mice on a Rag−/− C57BL/6 background, MyD88-TRIF double knock out, Clec9a$^+$, and Clec9a$^{-/-}$ mice were bred at Cancer Research UK in specific pathogen-free conditions. Bone marrow chimeras were made from Syk-deficient fetal liver cells as previously described (Turner et al. Nature 378, 298 (1995)) All animal experiments were performed in accordance with national and institutional guidelines for animal care.

Reagents

Culture medium was RPMI 1640 (Invitrogen) supplemented with glutamine, penicillin, streptomycin, 2-mercaptoethanol (all from Invitrogen) and 10% heat-inactivated foetal calf serum (Bioclear). Antibodies used for flow cytometry analysis experiments were from BD Pharmingen and included those specific for CD11c (clone HL3, hamster IgG1), CD24, CD11b, B220, Ly6C, CD4 (RM4-5, rat IgG2a), CD8. Antibodies used for ELISA were capture IFN-γ (XMG1.2, rat IgG1) detection/IL12-23 p40. Purified 2.4G2 (anti-FcgRIII/II, rat IgG2b, used to block unspecific Ab binding) was from Cancer Research UK antibody production service. For flow cytometry, cell suspensions were stained in ice-cold PBS supplemented with 2 mM EDTA, 1% FCS and 0.02% sodium azide. Data were acquired on a FACSCalibur (BD Biosciences) and analyzed using FlowJo software (Treestar, San Carlos, Calif.).

Cells

Mouse bone marrow-derived DCs (BMDCs) were generated using GM-CSF and purified from bulk cultures by magnetic selection with anti-CD1c microbeads (GM-CSF BMDCs). Alternatively, BMDCs were generated by culturing bone marrow cells in the presence of 100 ng/ml of Flt3L (R&D) for 10 days, by which time all living cells were positive for CD11c (Flt3L BMDCs). Spleen cells were prepared by liberase/DNAse digestion and enriched for DC by positive selection with anti-CD11c microbeads. OT-I T cells (from lymph nodes and spleen) were purified by negative selection using a cocktail of biotinylated antibodies (anti-CD11c, CD11b, B220, FcγR, Gr-1, and CD4) followed by streptavidin microbeads. Human peripheral blood mononuclear cells (PBMCs) were prepared from single donor leukocyte buffy coats (National Blood Transfusion Service) by sedimentation over Ficoll-Hypaque (GE-Healthcare).

PCR/RT-PCR

Total RNA was extracted using Trizol (Invitrogen) from subsets of splenic DC enriched in CD11c with anti-CD11c microbeads (Miltenyi) and sorted for CD4 and CD8 expression in a FacsAria sort (BD). In addition, RNA was extracted from sorted subsets of GMCSF and Flt3L in vitro derived BMDC. RNA was prepared by DNAse digestion (DNA-free, Ambion) and reverse transcribed using Superscript II reverse transcriptase (Gibco), 1 µM dNTPs and 10 µM random hexanucleotides (Gibco). cDNA was amplified using 35 PCR-cycles, consisting of 30 s 94° C., 30 s 55° C., 1 m 72° C. Sequences of primers were: mCLEC9a Fw 5' AGACTGCT-TCACCACTCCAA (SEQ ID NO: 9); mCLEC9a Rv: 5' CTTGGCACAATGGACAAGGT (SEQ ID NO: 10; b-actin Fw: 5' GTTTGAGACCTTCAACACCCC (SEQ ID NO: 11), b-actin Rv: 5' GTGGCCATCTCCTGCTCGAAGTC (SEQ ID NO: 12); hClec9a Fw: 5' CCCAAGTCTCATTTG-GAGGA (SEQ ID NO: 13; hClec9a-1 Rv: 5' AAATCTG-GACGGTGTGGAAG (SEQ ID NO: 14).

Generation of Anti-CLEC9a mAb mAbs Against Murine Clec9a

Wistar rats were immunized with RBL-2H3 cells transfected with CLEC9a fused to an HA epitope and fusion of splenocytes from hyper-immunized rats with the rat myeloma cell line Y3 was performed following standard procedures. For the detection of positives, we used the B3Z cell line[25] expressing a chimera with the extracellular domain of CLEC9a, the transmembrane region from NKRP1B and the intracellular tail of CD3ζ and followed by an IRES-GFP, a strategy that has been described[21]. The cDNA sequence of the fusion chimera for mCLEC9a is shown in FIG. 3. The B3Z cell line contains a reporter for NFAT coupled to β-Gal activity and any engagement of the chimerical molecule results in the activation of NFAT and the reporter, that can be then revealed following standard assays for b-Gal activity. The screening for antibodies was by functional activation of the B3Z expressing the chimera compared with the parental cell line. Those antibodies that were selected as positives were confirmed by FACS analysis in the parental cell line (EGFP−) compared to the CLEC9a chimera expressing cells (EGFP+). This method allowed the selection of three mAbs named 1F6, 397, and 7H11 as shown in FIG. 4. mAb were then conjugated to biotin or to Alexa488 for staining (Invitrogen), or used for conjugation with S1 peptide.

mAbs Against Human Clec9a

BALB/c mice were immunized 3-4 times with RBL-2H3 cells expressing human Clec9a fused to an HA epitope. Fusion of splenocytes with the mouse myeloma line SP2/0 was carried out using standard procedures. For hybridoma screening, we used the B3Z cell line, which expresses a β-gal reporter for NFAT (23). This cell line was transduced with a retrovirus encoding a chimera of the extracellular domain of human Clec9a fused to the transmembrane region from NKRP1B and the intracellular tail of CD3 followed by an IRES sequence and the GFP gene (24). Hybridoma supernatants were screened for the ability to bind to the Clec9a chimera, resulting in the activation of the NFAT reporter and induction of β-gal activity (24). Supernatants that tested positive in this assay were further screened by flow cytometry using a mixture of B3Z cells expressing the chimera Clec9a (GFP+) and parental B3Z cells (GFP−). This method allowed the selection of one mouse mAb specific for hClec9a (8F9 (IgG2a)).

Flow Cytometry

Fluorochrome- or biotin-labeled antibodies specific for mouse CD11c, CD24, CD11b, B220, Ly6C, CD4 and CD8α were from BD Pharmingen. Purified 2.4G2 (anti-FcγRIII/II) was from Cancer Research UK antibody production service. Mouse cell suspensions were incubated with 10 µg/ml of 2.4G2 mAb to block Fcγ receptors and were then stained in icecold PBS supplemented with 2 mM EDTA, 1% FCS and 0.02% sodium azide. For endocytosis studies, FcγR-blocked cells were labeled with 5 µg/ml of biotinylated anti-Clec9a mAb for 30 min at 4° C. Cells were then washed twice and incubated for different times at 4° C. or 37° C. before transferring to ice and adding streptavidin PE. For in vivo labeling studies, Alexa-488 conjugated anti-Clec9a or isotype-matched control mAbs were injected i.v. at the indicated dose and tissues were prepared and analyzed after 16 h. Antibodies specific for human CD3, CD14, CD19, CD56, HLA-DR, CD34, CD123 and CD16 were purchased from BD, and CD1b/c, and BDCA-3 were from AbCam (Cambridge, UK). Human mononuclear cells were blocked with 100 µg/ml human IgG (Sigma-Aldrich) and stained as above. Data were acquired on a FACSCalibur (BD Biosciences) and analyzed using FlowJo software (Treestar, San Carlos, Calif.).

BM-DC Culture and Stimulation

GM-CSF BM-DC were generated as described[26] and DC were purified from bulk cultures with anti-CD11c microbeads before use (Miltenyi Biotec). BM-DC purity was checked by FACS and was routinely >98% (data not shown). Flt3L BMDC were generated from bone marrow cultured in the presence of 75 ng/ml or 50 ng/ml of Flt3L (R&D) for 10 days. For cytokine production and surface marker expression analyses, $5-10 \times 10^4$ Flt3L BM-DC per well were cultured for 18-24 hours in 200 ml culture medium containing Flt3L in 96-well flat-bottomed plates previously coated with isotype control or anti-CLEC9a mAb. Cytokine levels in the supernatants were measured by sandwich ELISA using capture anti-IL-12 p40-p70 (C15.6) and detection biotin anti- IL12p40-p70 (C17.8), both from BD. For endocytosis in Flt3L BMDC, FcγR were blocked with 10 μg/ml of 2.4G2 mAb and cells were then cultured with 5 μg/ml of biotinylated mAb for 30 min at 4° C. or 37° C., washed and allowed for 1.5 h or 0.5 h at the assay temperature before washing and adding simultaneously the secondary reagent (streptavidin PE) at 4° C. For confocal analysis, Alexa 488 conjugated mAb were added to FcγR-blocked Flt3L-BMDC at 5 mg/ml for 30 min at 4° C. or 37° C. and then washed and allowed for a further 1.5 h at the assay temperature before allowing to adhere to poly-L-lysine-coated coverslips and fixation in 2% PFA for 20 min RT. Samples were mounted in slides with Fluoromount (Southern Biotech, Birmingham, Ala.). A confocal series of differential interference contrast and fluorescence images was obtained simultaneously with a laser scanning confocal microscope (Axioplan 2, Zeiss, Germany) with a 63°—Plan-Apochromat NA 1.4 oil objective. Image analysis was performed with LSM 510 software (Zeiss, Germany).

Peptide Pull-Downs and Western Blotting

For peptide pull-downs, biotin-conjugated peptides were dissolved in 40% DMSO before dilution in lysis buffer. Recombinant human Syk (Upstate) diluted in lysis buffer was incubated with the indicated biotinylated peptides corresponding to the CLEC9a and Dectin-1 intracellular tail (Cancer ResearchUK Peptide Synthesis Laboratory) and streptavidin-sepharose (Sigma Biosciences AB, Uppsala, Sweden). After affinity purification, Sepharose beads were washed once in lysis buffer and boiled in SDS gel-loading buffer containing 10% β-mercaptoethanol. Proteins were separated by sodium-dodecyl-sulfate-polyacrylamide gel electrophoresis (SDS-PAGE), transferred onto Immobilon PVDF membranes (Millipore Corporation, Bedford, Mass.), and probed with rabbit anti-Syk (a combination of 2131 serum raised against a synthetic peptide corresponding to amino acids 318-330 of murine Syk[20] and anti-Syk from Cell Signaling Technology, Inc., catalog number 2712, raised against a synthetic peptide corresponding to the C terminus of human Syk) followed by chemiluminescent detection.

In the LK cell activation assay, LK cells were plated in 6-well plates coated with anti-C9 or isotype control for the indicated times. Cell extracts were prepared in lysis buffer (50 mM HEPES [pH 7.4], 150 mM sodium chloride, 100 mM sodium fluoride, 10 mM tetrasodium pyrophosphate, 1 mM sodium orthovanadate [pH 10.0], 1 mM EDTA [pH 8.0], 1.5 mM magnesium chloride, 10% glycerol, 1% Triton X-100, 1 mM PMSF, and "Complete" protease inhibitor cocktail tablets [Roche]); insoluble material was discarded and a fixed amount of lysate was run by SDS-PAGE as described above. For WB rabbit anti-Syk as above and anti-P-Syk, anti-Erk, anti-P-Erk were from Cell Signaling.

NFAT Reporter Assay in B3Z and BWZ Cells

B3Z cells containing a reporter plasmid for NFAT coupled to LacZ activity have been previously described[25]. CLEC9a WT or a mutant version Y7F (Stratagene) were transduced in wt or Syk-transduced B3Z cells. Cells were plated in 96 well plates coated with isotype control or anti-CLEC9a mAb and after overnight culture, were washed in PBS and lysed in CPRG-containing buffer as described[21]. Four hours later A595 was measured, using OD 655 as a reference.

For detection of CLEC9A ligands, BWZ cell line was transduced with a retrovirus encoding a chimera of the extracellular domain of mouse or human CLEC9A fused to the transmembrane region from NKRP1B and the intracellular tail of CD3 followed by an IRES sequence and the GFP gene (24). Ligand binding to the CLEC9A chimera would result in the activation of the NFAT reporter and induction of β-gal activity. To assay basal activation of BWZ cells expressing mouse and human CLEC9A-CD3 chimeric receptors, 4, 2, 1, or $0.5 \times 10^5$ cells/ml were cultured in 3 ml in a 6 well plate and allowed to (over)grow for two days. Frequency of dead cells was determined using TO-PRO3 dye (Invitrogen) and live cells were plated in fresh medium at $2 \times 10^5$/well in 96-well flat bottom plates. After overnight culture, LacZ activity was measured as above.

To determine exposure of ligand in different cell types, LK (B cell line), SV-40 immortalized mouse embryonic fibroblasts (MEFs) derived from bm-1 mice {Ref} using standard protocols, RBL rat leukemia, 3T3 fibroblasts, and HEK-293 human embryonic kidney cells were UV irradiated (240 mJ/cm$^2$) and left 24 h to induce cell death before adding to $2 \times 10^5$ BWZ transfectants in a 96-well flat bottom plate at a 1:1 ratio in the presence or absence of control Fab or anti-mouse CLEC9A (1F6) and anti-human CLEC9A (8F9) Fab (Sancho et al, J Clin Invest. 2008; 118(6):2098-110). After overnight culture, LacZ activity was measured as above. In some assays, BWZ cells transfected with CLEC9A wt were used to determine if the ligand signals through the cytoplasmic tail and evaluate full antibodies as blocking reagents comparable to the Fab.

UV dose response was performed irradiating LK cells with the following doses of UV (mJ/cm$^2$): 0, 0.5, 1.5, 5, 15, 50, 240. Frequency of dead cells was determined 24 h later using to-pro3 dye and cells were plated 1:1 with BWZ transfectants ($2 \times 10^5$ cells/well) in fresh medium. After overnight culture, LacZ activity was measured as above.

Different treatments for LK cells and bm-1 immortalized MEFs were evaluated in exposure of the ligand. Cells were cultured for 24 h with Mitoxantrone (1 μM) or in the absence of serum (serum deprivation). Osmotic shock was performed as previously described (Liu et al. 2002. J. Exp. Med. 196: 1091-1097). Three cycles of freeze-thaw were performed in the pellet of cells, freezing in liquid N$_2$ and thawing at 37° C. After these treatments, Frequency of dead cells was determined using to-pro3 dye and cells were stained for rsCTLD as indicated below. Cells were plated 1:1 with BWZ transfectants ($2 \times 10^5$ cells/well) in fresh medium. After overnight culture, LacZ activity was measured as above.

Coupling of SIINFEKLC (SEQ ID NO: 6)-Biot (S1) to mAb.

To conjugate the immunodominant OVA peptide SIINFEKL (SEQ ID NO: 7) to the bivalent antibody, a derivative of the SIINFEKL (SEQ ID NO: 7) peptide, named S1, containing an added Cysteine (C) to generate a free sulfhydril group and biotin to track the labelling was synthesized and purified by high-performance liquid chromatography at Cancer Research UK. The mAb were treated with sulfo-SMCC 30 min at RT, generating sulfo-reactive groups in the tertiary amines, followed by purification of the activated antibody in a molecular size exclusion chromatography column (Pierce). Then, the S1 peptide was freshly prepared and allowed to react in equimolecular amounts with the activated antibody 1 h at 37° C., and purified in a chromatography column. The extent of biotinylation of the mAb allowed us to quantify in 1-1.2 peptides coupled per mAb molecule in all antibody conjugates generated, using the Fluoreporter kit (Invitrogen) and following manufacturer's instructions.

Coupling of S2 Peptide and Melanocyte Differentiation Antigen Peptides to mAb

S2 peptide (SIINFEKLTEWTSSNVMEERC-biotin) was synthesized and purified by HPLC at Cancer Research UK. mAbs in PBS were treated with sulfo-SMCC for 30 min at room temperature to generate sulfo-reactive groups in tertiary amines. The activated antibody was purified by molecular size exclusion chromatography (Pierce), S2 peptide was added (2:1 molar ratio) and the reaction was allowed to proceed for 1 h at 37° C. Conjugates were purified using an Immunobind sepharose column. The extent of biotinylation of the mAb was assessed using the Fluoreporter kit (Invitrogen) as per manufacturer's instructions.

The same strategy was used to synthesize peptides from the melanocyte differentiation antigens, gp100 (EGSRNQDWL (SEQ ID NO: 15) and KVPRNQDWL (SEQ ID NO: 16); H-2Db-restricted (25)), TRP-1 (TWHRYHLL (SEQ ID NO: 17) and TAYRYHLL (SEQ ID N018); H-2Kb-restricted (26)) and TRP-2 (SVYDFFVWL SEQ ID NO: 19); H-2 Kb-restricted (27)), each modified by addition of cysteine-eahx-biotin at the C-terminus.

Targeting In Vivo with Anti-CLEC9a mAb.

Anti-CLEC9a, isotype control, or anti-DEC-205 were coupled to Alexa488 (Invitrogen) or to S1 peptide. For the experiment of targeting using Alexa488 Abs, mAb-Alexa488 were injected i.v. (20 μg) and splenocytes were extracted and analyzed after 16 h.

In the experiment of targeting of antigen to specific subsets in vivo, S1-Abs were injected i.v. (5 μg) and splenocytes were extracted and purified in the CD11c positive and negative fraction with anti-CD11c microbeads (Miltenyi Biotec). OT-I cells were obtained from lymph nodes and splenocytes of OT-I Rag−/− mice and purified by negative selection using a cocktail of biotinylated antibodies (anti-CD11c, CD11b, B220, FcgR, Gr-1, and CD4) followed by streptavidin microbeads (Miltenyi Biotec). Different amounts of in vivo targeted DC, as indicated in the Figure legend, were cultured with $10^5$ OT-I cells labelled with 2 μM CFSE (Invitrogen) in U-bottomed plates. Three days later, proliferation was determined by CFSE dilution in cells positive for Vβ5.1 and CD8 and negative for TO-PRO 3. Cells were acquired with true count beads ( . . . ) to quantify the absolute number of cells. IFN-γ in the supernatants was determined by sandwich ELISA.

In the experiment of targeting in vivo to evaluate specific CTL response, mAb-S1 were injected s.c. in the hind paws (2 μg) together or not with 25 μg of anti-CD40 (3/23, BD Pharmingen) and five days later in vivo killing assays were performed as described[27]. Briefly, target splenocytes from B6.SJL background (congenic CD45.1+) were loaded with 20 nM, 200 nM or no SIINFEKL (SEQ ID NO: 7) peptide and respectively labelled with 0.03 μM, 0.3 μM or 3 μM of CFSE for 20 min at 37° C. Labelled splenocytes ($10^7$) were i.v. injected. The following day splenocytes were extracted and the CD45.1 positive population was analyzed for CFSE. In addition, 5×$10^5$ splenocytes were cultured in the presence or absence of 1 μM SIINFEKL (SEQ ID NO: 7) for 24 h and supenatants were quantified for IFNγ by ELISA. Blood and spleen cells were also labeled with SIINFEKL (SEQ ID NO: 7)-H2Kb tetramer (Beckman Coulter), anti-CD8 and anti-Thy 1.2 and analyzed for the % tetramer+ cells among the CD8+ T cell population.

B16 Melanoma Tumor Therapy Model.

B16 melanoma cells were transduced with OVA-GFP fusion protein and sorted for GFP expression. Tumor cells (2×$10^5$) were injected i.v. in the tail of congenic B6 mice and 6 days later the therapeutic treatment consisting of Ab-S1+ anti-CD40 was injected s.c. in the paw. At day 18 post-tumor injection, lung tumors were counted. Tumor therapy experiments were done in an analogous fashion except that mice received B16-OVA 3 days prior to antibody treatment.

Tumor therapy and prophylaxis experiments were also carried out with non-transduced parental B16 cells. These were given i.v. (5×105/mouse) either 3 days before (therapy) or 1 day after (prophylaxis) immunization with anti-CLEC-9a or control antibody covalently coupled to a mixture of 5 peptides derived from gp100, TRP-1 and TRP-2 (1 μg/paw) together with anti-CD40 (12.5 μg/paw) and poly 1:0 (5 μg/paw). Tumor burden was assessed by counting lung foci. When these were too numerous to count (>250 per mouse), they are shown as 250. CTL responses were monitored as described above.

Generation of Clec9a−/− Mice.

Mice were generated using Red/ET recombineering (Gene Bridges, Heidelberg, Germany) to capture directly the region of the gene to modify from the BAC clone RP-23 248-K14 (C57BL/6 BAC clone from Invitrogen). A conventional gene-targeting replacement vector: pFloxRI+tk, which uses the strategy of both positive (neomycin resistance gene) and negative (herpes simplex virus thymidine kinase gene) selection for the isolation of homologous recombinant ES cells clones was amplified by PCR using the primers indicated with 20 nucleotides pairing with the vector and 70 nucleotides pairing with regions of Clec9a to capture. The primers used were Fw 3arm 24330 pFlox 5' ATAATATCAT ATTTC-TATAA TATCATTGTA ATGACAAAAC CACTGAACTA GTGCCTGTAA AGGCAGGAGG GGTACCGAGC TCGAATTCTA CCG 3' SEQ ID NO: 20); Rv pFlox 5arm 5'TGCTATATTA CAGATTTTCA AGTGGGGTAG CCTG-GAGTAA CAAGATGGCA GGGCATAATC ACTAGT-GCGG CCGCCACCGC GGTGGAGCTC CAGCTTT (SEQ ID NO: 21) 3'.

Once the region to modify was included in the Amp-resistant vector, a cassette including farnesylated EGFP, and the PGK-gb2 promoter followed by Kan/Neo allowed to repeat the recombineering homologous recombination step with selection for Kan. The primers used for amplification of the EGFP-F Kan-Neo resistant cassette were: Rv NeoKan 3arm 5' TGCTTTTGTA CTTACACTTG ATGCCCAAGA AAATGGACGT TGCTAACAAG CCCATACAGA CCA-CACCTCG AGATAACTTC GTATAATGTA T3'; (SEQ ID NO 22) and Fw 5arm EGFP-F 5' TTTGTGCCAG GCTC-CTATGT AGACTGCTTC ACCACTCCAA GCGCCT-TCAG CATGCATGTC GACATGGTGA GCAAGGGCGA GGAG 3'(SEQ ID NO: 11).

The targeting vector was prepared to express EGFP-F with a strong polyA immediately downstream the first two amino acids from CLEC9A and disrupted exons 1 and 2, terminating transcription with the strong polyA The targeting vector was linearized prior to transfection using Not I. Transfection of S6B6 hybrid 129S6/C57BL/6 F1 derived embryonic stem (ES) cells was achieved by electroporation and recombinant clones were isolated after culture in G418 and gancyclovir. ES cells surviving selection were screened by PCR using two independent primer pairs with one of the primers external to the short arm. The primer pairs used were: Scr Fwl 5' GATCT-GTGTG TTGGTTTTTG TGTGC 3'(SEQ ID NO: 24); Scr Rvl, 5' TAGCATGGCA CTTCTCCATT ACCTT 3' (SEQ ID NO: 25) Amplicon Fwl Rvl: 2138 bp. Scr Fw2, 5' GCGAAT-TCGG TACCAATAAA AGAGC 3' (SEQ ID NO: 26); Scr Rv2, 5' CAGAAGCTTC CTGGTTTTGG TTTTT 3' (SEQ ID NO: 27) Amplicon Fw2Rv2: 2352.

Correctly targeted, karyotypically euploid ES clones were micro-injected into 3.5 day post coitum C57BL/6 blastocysts and resulting offspring with coat-color chimerism were bred with C57BL/6 females to identify germ-line transmission. Germ-line transmitting chimeras were subsequently bred with C57BL/6 females to secure the gene-targeted allele in the pure C57BL/6 background. Heterozygous animals were interbred to generate homozygous deficient animal and matched littermate controls. The expression of NK1.1 C57BL/6 gene, ligated to Clec9a, in the knock out mice shows that the homologous recombination of the targeted C57BL/6 BAC clone was integrated in the C57BL/6 copy of the F1 in S6B6 ES cells.

Clec9a−/− mice used in this work were on a mixed 129/SvxC57BL/6 genetic background in the third generation of backcrossing to C57BL/6.

Recombinant Soluble CTLD Generation.

The CTLDs for mouse CLEC9A and Dectin-1 were independently cloned in frame in the p3xFlag-CMV-9 expression vector from Sigma with an added BirA monobiotinilation sequence. Primers used for CTLD amplification were mCLEC9A Fw 5'GGATCC mCLEC9A Rv 5'GGATCC mDectin Fw 5'GGATCC3' mDectin Rv 5'GGATCC3' CHO cells were transfected and selected with G418 (1 mg/ml). Stable transfectants were cloned twice by limiting dilution, selecting clones secreting rsCTLD from Dectin-1 or CLEC9A to the supernatant, detected by a sandwich ELISA using as capture anti-flag M2 (Sigma) and for detection biotin-2A11 anti-Dectin-1 or biotin-1F6 anti-CLEC9A. Concentrated supernatants from CHO clones were generated in CELLine bioreactors (Integra Biosciences, Chur, Switzerland) and were purified using anti-flag M2 agarose (Sigma). Monobiotinylation was then performed using standard procedures {Ref} and tetramers were generated using PE-Streptavidin (Sigma). PE-tetramers of rsCTLD were then used for staining of dead cells or zymosan for 30 min at 4° C. in normal FACS buffer. Samples were counter-stained with to-pro3 and acquired by flow cytometry.

Cross-Presentation In Vitro.

In the cross-presentation assay in vitro we co-cultured three cell types: dead cells loaded with OVA or expressing OVA, Flt3L BMDC from different origins in the presence or absence of antibodies blocking CLEC9A and the readout, OT-I OVA-specific transgenic T cells. We tested Flt3L BMDC from CLEC9a−/− or CLEC9a+ littermates. In addition, Flt3L BMDC from C57BL/6 were cultured in the absence or presence of control Fab, or anti-CLEC9A (1F6) Fab (10 μg/ml), as well as with full antibodies against CLEC9A or isotype control (20 μg/ml). Where indicated, CD8α-like Flt3L BMDC with CD11b$^{lo}$ and CD24$^{hi}$, as described (19), were sorted. As a source of dead cells associated to OVA antigen for cross-presentation, we used bm-1 splenocytes, a C57BL/6 congenic mouse that express a mutation in the H2K$^b$ molecule that prevents the binding of SIINFEKL (SEQ ID NO: 7) and the immunodominant class I OVA peptide for H2K$^b$. In that way, cells loaded with OVA will not be able to present directly the OVA peptide and should be processed and cross-presented to generate a response. To load the OVA by adsorption, we incubated the indicated doses of soluble OVA (Calbiochem) with low levels of endotoxin with bm-1 splenocytes in PBS for 20 min before washing five times in PBS. Alternatively, we generated bm-1 mouse embryonic fibroblasts (MEFs) and we immortalized them with SV-40 T large antigen. Then, we transduced then with a truncated non-secreted OVA-GFP fusion protein and sorted for homogeneous expression of OVA-GFP. Both, OVA-loaded splenocytes and OVA-expressing MEFs were then UV-irradiated (240 mJ/cm$^2$) and cultured overnight in complete medium. The following day, splenocytes were co-cultured 5:1 ratio to Flt3L BMDC (10$^5$ cells/well, 96 U-bottom) and OVA-MEFs were cultured with Flt3L BMDC in a 1:1 ratio. OT-I cells negatively selected (purity >80%) using MACS beads (Miltenyi) and labelled with CFSE (2 μM) were added to the assay (10$^5$ cells/well). Three days later supernatants were harvested to detect IL-2 and IFN-γ by sandwich ELISA and cells were stimulated with PMA (10 ng/ml) and Ionomycin (500 ng/ml) for 4 h, adding Brefeldin A (10 μg/ml, Sigma) during the last 3 h of culture. Cells were then stained for Vβ5, CD8 and IFN-γ by intracellular staining and acquired by flow cytometry to determine absolute counts, loading samples with a fixed number of calibration beads (BD) and IFN-γ production by intracellular staining.

Uptake of Dead Cells

WT or CLEC9a$^{−/−}$ CD8α-like Flt3L BMDC were incubated for 2 h with different ratios of splenocytes that were treated 24 h before with UVC (240 mJ/cm$^2$) and labelled with PKH26 (Sigma). As Flt3L BMDC were labelled for CD24, double positive for PKH26 and CD24 could be due to binding (4° C.) or binding+uptake (37° C.) of dying cells and the frequencies were quantified by flow cytometry for each type of DC.

Cross-Presentation In Vivo

OVA-expressing immortalized bm-1 MEFs generated as indicated above were UVC-treated (240 mJ/cm$^2$) and cultured overnight before being injected i.v. (0.75×10$^6$ cells/mouse). Mice (C57BL/6) were pre-treated with an i.p. injection of PBS or 400 μg isotype control (AFRO-MAC 49, rat IgG1) or 1F6 anti-CLEC9A 30 min before the i.v. injection. Alternatively, Clec9a$^{−/−}$ or littermates Clec9a$^+$ were used. Six days later, induction of CD8+ T cell effector response arising from the endogenous repertoire was tracked by the number of H2K$^b$-OVA peptide tetramer positive cells and IFNγ production in response to SIINFEKL (SEQ ID NO: 7) ex vivo in the CD8 subset. In FIGS. 19c and 19d in which data were pooled from several litters in independent experiments, we performed a normalization of the data before pooling. Each litter (females) was considered an independent experiment and raw data in each litter were normalized to the mean of Clec9a$^+$ mice in that litter and multiplied by the arithmetic mean obtained for the total population of Clec9a$^+$ mice in all the litters in independent experiments. For the analysis of fold change in litters, arithmetic mean for Clec9a$^+$ mice or Clec9a$^{−/−}$ mice was calculated in each litter. All 12 litters out of 12 analyzed showed fold reduction in the arithmetic mean of % tetramer positive cells in CD8 T cell subset of Clec9a$^{−/−}$ mice compared to Clec9a$^+$.

Statistics

Statistical analysis was performed with a two-tailed Student's t test for differences among groups or U Mann-Whitney when normality of data could not be inferred. p<0.05 was considered statistically significant. Quantitative data are expressed as means±SEM unless otherwise stated.

While the invention has been described in conjunction with the exemplary embodiments described above, many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

REFERENCES

1. Reis e Sousa, C. Activation of dendritic cells: translating innate into adaptive immunity. *Curr Opin Immunol* 16, 21-5 (2004).
2. Engering, A. et al. The dendritic cell-specific adhesion receptor DC-SIGN internalizes antigen for presentation to T cells. *J Immunol* 168, 2118-26 (2002).
3. Sallusto, F., Cella, M., Danieli, C. & Lanzavecchia, A. Dendritic cells use macropinocytosis and the mannose receptor to concentrate macromolecules in the major histocompatibility complex class II compartment: downregulation by cytokines and bacterial products. *J Exp Med* 182, 389-400 (1995).
4. Mahnke, K. et al. The dendritic cell receptor for endocytosis, DEC-205, can recycle and enhance antigen presentation via major histocompatibility complex class II-positive lysosomal compartments. *J Cell Biol* 151, 673-84 (2000).
5. Ariizumi, K. et al. Identification of a novel, dendritic cell-associated molecule, dectin-1, by subtractive cDNA cloning. *J Biol Chem* 275, 20157-67 (2000).
6. Ariizumi, K. et al. Cloning of a second dendritic cell-associated C-type lectin (dectin-2) and its alternatively spliced isoforms. *J Biol Chem* 275, 11957-63 (2000).
7. Bates, E. E. et al. APCs express DCIR, a novel C-type lectin surface receptor containing an immunoreceptor tyrosine-based inhibitory motif. *J Immunol* 163, 1973-83 (1999).
8. Dzionek, A. et al. BDCA-2, a novel plasmacytoid dendritic cell-specific type II C-type lectin, mediates antigen capture and is a potent inhibitor of interferon alpha/beta induction. *J Exp Med* 194, 1823-34 (2001).
9. Brown, G. D. & Gordon, S. Immune recognition. A new receptor for beta-glucans. *Nature* 413, 36-7 (2001).
10. Ardavin, C. Origin, precursors and differentiation of mouse dendritic cells. *Nat Rev Immunol* 3, 582-90 (2003).
11. Huang, Q. et al. The plasticity of dendritic cell responses to pathogens and their components. *Science* 294, 870-5 (2001).
12. Reis e Sousa, C. et al. In vivo microbial stimulation induces rapid CD40 ligand-independent production of interleukin 12 by dendritic cells and their redistribution to T cell areas. *J Exp Med* 186, 1819-29 (1997).
13. Schulz, O. et al. CD40 triggering of heterodimeric IL-12 p70 production by dendritic cells in vivo requires a microbial priming signal. *Immunity* 13, 453-62 (2000).
14. Edwards, A. D. et al. Microbial recognition via Toll-like receptor-dependent and -independent pathways determines the cytokine response of murine dendritic cell subsets to CD40 triggering. *J Immunol* 169, 3652-60 (2002).
15. Maldonado-Lopez, R. et al. CD8alpha+ and CD8alpha– subclasses of dendritic cells direct the development of distinct T helper cells in vivo. *J Exp Med* 189, 587-92 (1999).
16. Maldonado-Lopez, R., Maliszewski, C., Urbain, J. & Moser, M. Cytokines regulate the capacity of CD8alpha(+) and CD8alpha(−) dendritic cells to prime Th1/Th2 cells in vivo. *J Immunol* 167, 4345-50 (2001).
17. Boonstra, A. et al. Flexibility of mouse classical and plasmacytoid-derived dendritic cells in directing T helper type 1 and 2 cell development: dependency on antigen dose and differential toll-like receptor ligation. *J Exp Med* 197, 101-9 (2003).
18. Bonifaz, L. C. et al. In vivo targeting of antigens to maturing dendritic cells via the DEC-205 receptor improves T cell vaccination. *J Exp Med* 199, 815-24 (2004).
19. Naik, S. H. et al. Cutting edge: generation of splenic CD8+ and CD8− dendritic cell equivalents in Fms-like tyrosine kinase 3 ligand bone marrow cultures. *J Immunol* 174, 6592-7 (2005).
20. Turner, M. et al. Perinatal lethality and blocked B-cell development in mice lacking the tyrosine kinase *Syk*. *Nature* 378, 298-302 (1995).
21. Bijker, M. S. et al. CD8+ priming by exact peptide epitopes in incomplete Freund's adjuvant induces a vanishing CTL response, whereas long peptides induce sustained CTL reactivity. *J. Immunol.* 179(8), 5033-5040 (2007).
22. MacDonald K P, et al. Characterization of human blood dendritic cell subsets. Blood 100(13):4512-20 (2002).
23. Karttunen, J., S. Sanderson, and N. Shastri. 1992. Detection of rare antigen-presenting cells by the lacZ T-cell activation assay suggests an expression cloning strategy for T-cell antigens. *Proc. Natl. Acad. Sci. U.S.A.* 89:6020-6024.
24. Mesci, A., and J. Carlyle. 2007. A rapid and efficient method for the generation and screening of monoclonal antibodies specific for cell surface antigens. *J. Immunol. Methods* 323:78-87.
25. Overwijk, W. W., Tsung, A., Irvine, K. R., Parkhurst, M. R., Goletz, T. J., Tsung, K., Carroll, M. W., Liu, C., Moss, B., Rosenberg, S. A., et al. 1998. gp100/pmel 17 is a murine tumor rejection antigen: induction of "self"-reactive, tumoricidal T cells using high-affinity, altered peptide ligand. *J Exp Med* 188:277-286.
26. Dyall, R., Bowne, W. B., Weber, L. W., LeMaoult, J., Szabo, P., Moroi, Y., Piskun, G., Lewis, J. J., Houghton, A. N., and Nikolic-Zugic, J. 1998. Heteroclitic immunization induces tumor immunity. *J Exp Med* 188:1553-1561.
27. Bloom, M. B., Perry-Lalley, D., Robbins, P. F., Li, Y., el-Gamil, M., Rosenberg, S. A., and Yang, J. C. 1997. Identification of tyrosinase-related protein 2 as a tumor rejection antigen for the B16 melanoma. *J Exp Med* 185: 453-459.

The invention claimed is:

1. A composition comprising a peptide antigen, wherein the antigen is associated with a binding agent which comprises an antibody or functional fragment thereof having specific affinity for a CLEC9a protein of SEQ ID NO: 2 or SEQ ID NO:4, and wherein said antigen is a tumor-specific antigen or a human self antigen against which an immune response occurs in an auto-immune disease.

2. A composition according to claim 1 wherein said antibody or functional fragment has specific affinity for an extracellular domain of CLEC9a and said composition comprises a pharmaceutically acceptable carrier.

3. A composition according to claim 1 formulated for intravenous, intramuscular, intraperitoneal, nasal, subcutaneous or intradermal administration.

4. A composition according to claim 1 wherein the composition further comprises an adjuvant.

5. A composition according to claim 4 wherein the adjuvant is selected from the group consisting of retinoic acid, a CD40 agonist, a TLR agonist, and other immunostimulatory agents.

6. A composition according to claim 1 wherein the antigen is covalently coupled to the binding agent.

7. A composition according to claim 1 wherein the antigen and binding agent are part of the same peptide chain.

8. A composition according to claim 1 wherein the binding agent is an agonist of CLEC9a.

9. A composition according to claim 1 wherein the antigen is a tumour-specific antigen.

* * * * *

SEQUENCE LISTING

<160> NUMBER OF SEQ ID NOS: 27

<210> SEQ ID NO 1
<211> LENGTH: 726
<212> TYPE: DNA
<213> ORGANISM: Homo sapiens

<400> SEQUENCE: 1

```
atgcacgagg aagaaatata cacctctctt cagtgggata gcccagcacc agacacttac      60
cagaaatgtc tgtcttccaa caaatgttca ggagcatgct gtcttgtgat ggtgatttca     120
tgtgttttct gcatgggatt attaacagca tccattttct gggcgtcaa gttgttgcag     180 gtgtccacca ttgcgatgca gcagcaagaa aaactcatcc aacaagagag ggcactgcta     240
aactttacag aatggaagag aagctgtgcc cttcagatga aatattgcca agccttcatg     300
```

```
caaaactcat taagttcagc ccataacagc agtccttgtc caaacaattg gattcagaac    360
agagaaagtt gttactatgt ctctgaaatt tggagcattt ggcacaccag tcaagagaat    420
tgtttaaagg aaggttccac gctgctacaa atagagagca aagaagaaat ggattttatc    480
actggcagct tgaggaagat taaaggaagc tatgattact gggtgggggtt gtctcaggat    540 ggacacagcg gacgctggct ttggcaagat ggctcctctc cttctcctgg cctgttgcca    600
gcagagagat cccagtcagc taaccaagtc tgtggatacg tgaaaagcaa ttcccttctt    660
tcgtctaact gcagcacgtg gaagtatttt atctgtgaga agtatgcgtt gagatcctct    720
gtctga                                                               726
```

<210> SEQ ID NO 2
<211> LENGTH: 241
<212> TYPE: PRT
<213> ORGANISM: Homo sapiens

<400> SEQUENCE: 2

```
Met His Glu Glu Glu Ile Tyr Thr Ser Leu Gln Trp Asp Ser Pro Ala
1               5                   10                  15

Pro Asp Thr Tyr Gln Lys Cys Leu Ser Ser Asn Lys Cys Ser Gly Ala
            20                  25                  30

Cys Cys Leu Val Met Val Ile Ser Cys Val Phe Cys Met Gly Leu Leu
        35                  40                  45

Thr Ala Ser Ile Phe Leu Gly Val Lys Leu Leu Gln Val Ser Thr Ile
    50                  55                  60

Ala Met Gln Gln Gln Glu Lys Leu Ile Gln Gln Glu Arg Ala Leu Leu
65                  70                  75                  80

Asn Phe Thr Glu Trp Lys Arg Ser Cys Ala Leu Gln Met Lys Tyr Cys
                85                  90                  95

Gln Ala Phe Met Gln Asn Ser Leu Ser Ser Ala His Asn Ser Ser Pro
            100                 105                 110

Cys Pro Asn Asn Trp Ile Gln Asn Arg Glu Ser Cys Tyr Tyr Val Ser
        115                 120                 125

Glu Ile Trp Ser Ile Trp His Thr Ser Gln Glu Asn Cys Leu Lys Glu
    130                 135                 140

Gly Ser Thr Leu Leu Gln Ile Glu Ser Lys Glu Glu Met Asp Phe Ile
145                 150                 155                 160

Thr Gly Ser Leu Arg Lys Ile Lys Gly Ser Tyr Asp Tyr Trp Val Gly
                165                 170                 175

Leu Ser Gln Asp Gly His Ser Gly Arg Trp Leu Trp Gln Asp Gly Ser
            180                 185                 190

Ser Pro Ser Pro Gly Leu Leu Pro Ala Glu Arg Ser Gln Ser Ala Asn
        195                 200                 205

Gln Val Cys Gly Tyr Val Lys Ser Asn Ser Leu Leu Ser Ser Asn Cys
    210                 215                 220

Ser Thr Trp Lys Tyr Phe Ile Cys Glu Lys Tyr Ala Leu Arg Ser Ser
225                 230                 235                 240

Val
```

<210> SEQ ID NO 3
<211> LENGTH: 796
<212> TYPE: DNA
<213> ORGANISM: Mus musculus

<400> SEQUENCE: 3

```
atgcatgcgg aagaaatata tacctctctt cagtgggaca ttcctacctc agaggcctct    60
cagaagtgcc aatcccctag caaatgttca ggagcatggt gtgttgtgac gatgatttcc   120
tgtgtggtct gtatgggctt gttagcaacg tccattttct gggcatcaa gttcttccag   180
gtatcctctc ttgtcttgga gcagcaggaa agactcatcc aacaggacac agcattggtg   240
aaccttacac agtggcagag gaaatacaca ctggaatact gccaagcctt actgcagaga   300
tctctccatt caggcacaga tgcttctact ggaccagttc ttctgacctc tccacagatg   360
gttccacaga ccctggacag caaggaaaca ggtagtgact gcagcccttg ccacacaac    420
tggattcaga atggaaaaag ttgttactat gtctttgaac gctgggaaat gtggaacatc   480
agtaagaaga gctgttttaaa agagggcgct agtctctttc aaatagacag caaagaagaa   540
atggagttca tcagcagtat agggaaactc aaaggaggaa ataaatattg ggtgggagtg   600
tttcaagatg gaatcagtgg atcttggttc tgggaagatg gctcttctcc tctctctgac   660
ttgttgcctg cagaaagaca gcgatcagcc ggccagatct gtggatacct caaagattct   720
actctcatct cagataagtg cgatagctgg aaatattta tctgtgagaa gaaggcagtt   780
tggatcctgc atctga                                                   796
```

<210> SEQ ID NO 4
<211> LENGTH: 264
<212> TYPE: PRT
<213> ORGANISM: Mus musculus

<400> SEQUENCE: 4

```
Met His Ala Glu Glu Ile Tyr Thr Ser Leu Gln Trp Asp Ile Pro Thr
1               5                   10                  15

Ser Glu Ala Ser Gln Lys Cys Gln Ser Pro Ser Lys Cys Ser Gly Ala
            20                  25                  30

Trp Cys Val Val Thr Met Ile Ser Cys Val Val Cys Met Gly Leu Leu
        35                  40                  45

Ala Thr Ser Ile Phe Leu Gly Ile Lys Phe Phe Gln Val Ser Ser Leu
    50                  55                  60

Val Leu Glu Gln Gln Glu Arg Leu Ile Gln Gln Asp Thr Ala Leu Val
65                  70                  75                  80

Asn Leu Thr Gln Trp Gln Arg Lys Tyr Thr Leu Glu Tyr Cys Gln Ala
                85                  90                  95

Leu Leu Gln Arg Ser Leu His Ser Gly Thr Asp Ala Ser Thr Gly Pro
            100                 105                 110

Val Leu Leu Thr Ser Pro Gln Met Val Pro Gln Thr Leu Asp Ser Lys
        115                 120                 125

Glu Thr Gly Ser Asp Cys Ser Pro Cys Pro His Asn Trp Ile Gln Asn
    130                 135                 140

Gly Lys Ser Cys Tyr Tyr Val Phe Glu Arg Trp Glu Met Trp Asn Ile
145                 150                 155                 160

Ser Lys Lys Ser Cys Leu Lys Glu Gly Ala Ser Leu Phe Gln Ile Asp
                165                 170                 175

Ser Lys Glu Glu Met Glu Phe Ile Ser Ser Ile Gly Lys Leu Lys Gly
            180                 185                 190

Gly Asn Lys Tyr Trp Val Gly Val Phe Gln Asp Gly Ile Ser Gly Ser
        195                 200                 205

Trp Phe Trp Glu Asp Gly Ser Ser Pro Leu Ser Asp Leu Leu Pro Ala
    210                 215                 220

Glu Arg Gln Arg Ser Ala Gly Gln Ile Cys Gly Tyr Leu Lys Asp Ser
```

225                 230                 235                 240
    Thr Leu Ile Ser Asp Lys Cys Asp Ser Trp Lys Tyr Phe Ile Cys Glu
                      245                 250                 255
    Lys Lys Ala Phe Gly Ser Cys Ile
                260

<210> SEQ ID NO 5
<211> LENGTH: 870
<212> TYPE: DNA
<213> ORGANISM: Artificial sequence
<220> FEATURE:
<223> OTHER INFORMATION: Synthetic sequence: CD3zeta - NKRP1 - CLEC9a
      chimera

<400> SEQUENCE: 5
atgagagcaa aattcagcag gagtgcagag actgctgcca acctgcagga ccccaaccag     60
ctctacaatg agctcaatct agggcgaaga gaggaatatg acgtcttgga gaagaagcgg    120
gctcgggatc cagagatggg aggcaaacag cagaggagga ggaaccccca ggaaggcgta    180
tacaatgcac tgcagaaaga caagattgca gaagcctaca gtgagatcgg cacaaaaggc    240
gagaggcgga gaggcaaggg gcacgatggc ctttaccagg gtctcagcac tgccaccaag    300
gacacctatg atgccctgca tatgcagacc ctggcccctc gctgtcggtg ccctcgctgg    360
catcggttgg ctctgaaatt tggctgtgct ggcctcatcc ttcttgtgct ggtcgtgatt    420
ggactctgtg tcttggtgct atcagtacaa aaatcatcac tcgagggtag tgactgcagc    480
ccttgtccac acaactggat tcagaatgga aaaagttgtt actatgtctt gaacgctgg     540 gaaatgtgga acatcagtaa agagagctgt ttaaagagg gcgctagtct ctttcaaata    600
gacagcaaag aagaaatgga gttcatcagc agtataggga aactcaaagg aggaaataaa    660
tattgggtgg gagtgtttca agatggaatc agtggatctt ggttctggga agatggctct    720
tctcctctct ctgacttgtt gcctgcagaa agacagcgat cagccggcca gatctgtgga    780
tacctcaaag attctactct catctcagat aagtgcgata gctggaaata tttatctgt    840 gagaagaagg catttggatc ctgcatctga                                      870

<210> SEQ ID NO 6
<211> LENGTH: 9
<212> TYPE: PRT
<213> ORGANISM: Artificial sequence
<220> FEATURE:
<223> OTHER INFORMATION: Synthetic sequence: S1

<400> SEQUENCE: 6

Ser Ile Ile Asn Phe Glu Lys Leu Cys
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic sequence: OVA peptide

<400> SEQUENCE: 7

Ser Ile Ile Asn Phe Glu Lys Leu
1               5

<210> SEQ ID NO 8
<211> LENGTH: 21
<212> TYPE: PRT

<213> ORGANISM: Artificial sequence
<220> FEATURE:
<223> OTHER INFORMATION: Synthetic sequence: S2

<400> SEQUENCE: 8

Ser Ile Ile Asn Phe Glu Lys Leu Thr Glu Trp Thr Ser Ser Asn Val
1               5                   10                  15

Met Glu Glu Arg Cys
            20

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Primer mCLEC9a Fw

<400> SEQUENCE: 9
agactgcttc accactccaa                                           20

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Primer mCLEC9a Rv

<400> SEQUENCE: 10
cttggcacaa tggacaaggt                                           20

<210> SEQ ID NO 11
<211> LENGTH: 21
<212> TYPE: DNA
<213> ORGANISM: Artificial sequence
<220> FEATURE:
<223> OTHER INFORMATION: Synthetic sequence: Primer b-actin Fw

<400> SEQUENCE: 11
gtttgagacc ttcaacaccc c                                         21

<210> SEQ ID NO 12
<211> LENGTH: 23
<212> TYPE: DNA
<213> ORGANISM: Artificial sequence
<220> FEATURE:
<223> OTHER INFORMATION: Synthetic sequence: Primer b-actin Rv

<400> SEQUENCE: 12
gtggccatct cctgctcgaa gtc                                       23

<210> SEQ ID NO 13
<211> LENGTH: 20
<212> TYPE: DNA
<213> ORGANISM: Artificial sequence
<220> FEATURE:
<223> OTHER INFORMATION: Synthetic sequence: Primer hClec9a Fw

<400> SEQUENCE: 13
cccaagtctc atttggagga                                           20

<210> SEQ ID NO 14
<211> LENGTH: 20
<212> TYPE: DNA
<213> ORGANISM: Artificial sequence
<220> FEATURE:
<223> OTHER INFORMATION: Synthetic sequence: Primer hClec9a-1 Rv -continued

<400> SEQUENCE: 14
aaatctggac ggtgtggaag                                              20

<210> SEQ ID NO 15
<211> LENGTH: 9
<212> TYPE: PRT
<213> ORGANISM: Artificial sequence
<220> FEATURE:
<223> OTHER INFORMATION: Synthetic sequence: Peptide from the melanocyte
      differentiation antigen gp100

<400> SEQUENCE: 15

Glu Gly Ser Arg Asn Gln Asp Trp Leu
1               5

<210> SEQ ID NO 16
<211> LENGTH: 9
<212> TYPE: PRT
<213> ORGANISM: Artificial sequence
<220> FEATURE:
<223> OTHER INFORMATION: Synthetic sequence: Peptide from the melanocyte
      differentiation antigen gp100

<400> SEQUENCE: 16

Lys Val Pro Arg Asn Gln Asp Trp Leu
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic sequence: Peptide from the melanocyte
      differentiation antigen TRP-1

<400> SEQUENCE: 17

Thr Trp His Arg Tyr His Leu Leu
1               5

<210> SEQ ID NO 18
<211> LENGTH: 8
<212> TYPE: PRT
<213> ORGANISM: Artificial sequence
<220> FEATURE:
<223> OTHER INFORMATION: Synthetic sequence: Peptide from the melanocyte
      differentiation antigen TRP-1

<400> SEQUENCE: 18

Thr Ala Tyr Arg Tyr His Leu Leu
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic sequence: Peptide from the melanocyte
      differentiation antigen TRP-2

<400> SEQUENCE: 19

Ser Val Tyr Asp Phe Phe Val Trp Leu
1               5

<210> SEQ ID NO 20
<211> LENGTH: 93
<212> TYPE: DNA

```
<213> ORGANISM: Artificial sequence
<220> FEATURE:
<223> OTHER INFORMATION: Synthetic sequence: Primer Fw 3arm 24330 pFlox

<400> SEQUENCE: 20
ataatatcat atttctataa tatcattgta atgacaaaac cactgaacta gtgcctgtaa    60
aggcaggagg ggtaccgagc tcgaattcta ccg                                 93

<210> SEQ ID NO 21
<211> LENGTH: 97
<212> TYPE: DNA
<213> ORGANISM: Artificial sequence
<220> FEATURE:
<223> OTHER INFORMATION: Synthetic sequence: Primer Rv pFlox 5arm

<400> SEQUENCE: 21
tgctatatta cagattttca gtggggtag cctggagtaa caagatggca gggcataatc     60
actagtgcgg ccgccaccgc ggtggagctc cagcttt                             97

<210> SEQ ID NO 22
<211> LENGTH: 91
<212> TYPE: DNA
<213> ORGANISM: Artificial sequence
<220> FEATURE:
<223> OTHER INFORMATION: Synthetic sequence: Primer Rv NeoKan 3arm

<400> SEQUENCE: 22
tgcttttgta cttacacttg atgcccaaga aaatggacgt tgctaacaag cccatacaga    60
ccacacctcg agataacttc gtataatgta t                                   91

<210> SEQ ID NO 23
<211> LENGTH: 84
<212> TYPE: DNA
<213> ORGANISM: Artificial sequence
<220> FEATURE:
<223> OTHER INFORMATION: Synthetic sequence: Primer Fw 5arm EGFP-F

<400> SEQUENCE: 23
tttgtgccag ctcctatgt agactgcttc accactccaa gcgccttcag catgcatgtc     60
gacatggtga gcaagggcga ggag                                           84

<210> SEQ ID NO 24
<211> LENGTH: 25
<212> TYPE: DNA
<213> ORGANISM: Artificial sequence
<220> FEATURE:
<223> OTHER INFORMATION: Synthetic sequence: Primer Scr Fw1

<400> SEQUENCE: 24
gatctgtgtg ttggttttg tgtgc                                           25

<210> SEQ ID NO 25
<211> LENGTH: 25
<212> TYPE: DNA
<213> ORGANISM: Artificial sequence
<220> FEATURE:
<223> OTHER INFORMATION: Synthetic sequence: Primer Scr Rv1

<400> SEQUENCE: 25
tagcatggca cttctccatt acctt                                          25

<210> SEQ ID NO 26
<211> LENGTH: 25
```

```
<212> TYPE: DNA
<213> ORGANISM: Artificial sequence
<220> FEATURE:
<223> OTHER INFORMATION: Synthetic sequence: Primer Scr Fw2

<400> SEQUENCE: 26
gcgaattcgg taccaataaa agagc                                          25

<210> SEQ ID NO 27
<211> LENGTH: 25
<212> TYPE: DNA
<213> ORGANISM: Artificial sequence
<220> FEATURE:
<223> OTHER INFORMATION: Synthetic sequence: Primer Scr Rv2

<400> SEQUENCE: 27
cagaagcttc ctggttttgg ttttt                                          25
```